United States Patent
Larkins et al.

(10) Patent No.: US 10,006,875 B2
(45) Date of Patent: Jun. 26, 2018

(54) NANOTIP SENSOR

(71) Applicants: Grover Larkins, Miami, FL (US);
Yuriy A. Vlasov, Weston, FL (US)

(72) Inventors: Grover Larkins, Miami, FL (US);
Yuriy A. Vlasov, Weston, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 135 days.

(21) Appl. No.: 14/990,557

(22) Filed: Jan. 7, 2016

(65) Prior Publication Data
US 2016/0116426 A1   Apr. 28, 2016

Related U.S. Application Data

(63) Continuation of application No. 13/101,324, filed on May 5, 2011, now Pat. No. 9,267,919.

(51) Int. Cl.
*G01R 25/00* (2006.01)
*G01N 33/48* (2006.01)
(Continued)

(52) U.S. Cl.
CPC ........ *G01N 27/045* (2013.01); *B81C 1/00111* (2013.01); *G01N 15/1031* (2013.01);
(Continued)

(58) Field of Classification Search
CPC ............ C12Q 1/6825; C12Q 2563/155; G01N 27/3278
(Continued)

(56) References Cited

U.S. PATENT DOCUMENTS 6,123,819 A * 9/2000 Peeters .............. G01N 33/5438
                                                    204/403.01
6,914,279 B2 * 7/2005 Lu ....................... C12Q 1/6825
                                                    257/252
(Continued)

OTHER PUBLICATIONS

Walt D.R., Franz D.R. "Biological Warfare Detection " *Analytical Chemistry*, 2000, v. 72, n. 23, pp. 738A-746A.
(Continued)

*Primary Examiner* — Stephanie Bloss
(74) *Attorney, Agent, or Firm* — Marshall, Gerstein & Borun LLP

(57) ABSTRACT

Embodiments of a nanotip sensor for detecting and identifying chemical or biological particulates in a sample are disclosed. The nanotip sensor may include a plurality of nanotips, each with a cathode, an anode, and a gap between the cathode and the anode. An adsorbed particulate from the sample may bridge the gap between the cathode and the anode, forming an electrical circuit. A conductive spectrum of the particulates in the sample that are adsorbed onto the nanotips of the sensor may be determined, and by comparing the conductive spectrum of the sample with conductive spectrums of known particulates, one or more specific particulates contained in the sample may be detected and identified. Techniques to augment the specificity of the sensor and to clean the sensor for re-use are disclosed. Embodiments of systems and methods that use the nanotip sensor to detect chemical and biological particulates are disclosed.

10 Claims, 34 Drawing Sheets

(51) Int. Cl.
  G01N 27/04    (2006.01)
  G01N 27/49    (2006.01)
  G01N 15/10    (2006.01)
  G01N 15/14    (2006.01)
  G01N 33/487   (2006.01)
  B81C 1/00     (2006.01)

(52) U.S. Cl.
  CPC .............. *G01N 15/14* (2013.01); *G01N 27/49* (2013.01); *G01N 33/48707* (2013.01); *B81B 2201/0214* (2013.01); *B81B 2203/0361* (2013.01); *G01N 15/1484* (2013.01); *G01N 2015/1006* (2013.01); *G01N 2015/1087* (2013.01)

(58) Field of Classification Search
  USPC .................................................... 702/19, 65
  See application file for complete search history.

(56) References Cited

U.S. PATENT DOCUMENTS

2007/0210349 A1   9/2007   Lu et al.
2010/0101956 A1   4/2010   Choi et al.
2011/0151439 A1   6/2011   Stratis-Cullum

OTHER PUBLICATIONS

"An Introduction to Biological Agent Detection Equipment for Emergency First Responders" National Institute of Justice Guide 101-00, 2001.
Laxminarayan S., Kun L.G. "Combating Bioterrorism with Bioengineering" *IEEE Engineering in Medicine and Biology*, Sep./Oct. 2002, pp. 21-27.
John D. Rockefeller IV, United States Senator. In "Combating Bioterrorism with Bioengineering" by Swamy Laxminarayan and Luis G. Kun, IEEE Engineering in Medicine and Biology, Sep./Oct. 2002, p. 21-27.
State of the Union Address by President George W. Bush, Jan. 28, 2003. (http://www.whitehouse.gov/news/releases/2003/01/20030128-19.html).
Matsumoto G. "Anthrax Powder: State of the Art?" *Science*, 2003, v. 302, pp. 1492-1497.
Velsko S.P. "Physical and Chemical Analytical Analysis: A key component of Bioforensics" Lawrence Livermore National Laboratory, AAAS Annual Conference, Washington, DC, USA, Feb. 2005.
Cannons A ., Amuso P., Anderson B. "Biotechnology and the Public Health Response to Bioterrorism" in "Microorganisms and Bioterrorism" Springer, 2006, pp. 1-13.
Meselson M., Guillemin J., Hugh-Jones M., Langmuir A., Popova I., Shelokov A., O.Yampolskaya "The Sverdlovsk Anthrax Outbreak of 1979" *Science*, 1994, v. 266. n. 5188, pp. 1202-1208.
Friedlander A.M. "Anthrax". In: "Medical Aspects of Chemical and Biological Warfare". Specialty editors: F.R. Sidell, E.T. Takafuji, D,R. Franz. Publisher: Office of The Surgeon General at TMM Publications, Borden Institute, Walter Reed Army Medical Center, Washington, DC 20307-5001. 1997, pp. 467-478.
Little K. "A brief guide to anthrax." *Nursing Times*, Nov. 19-25, 2002, v. 98, n. 47, pp. 28-29.
Dixon T.C., Meselson M., Guillemin J., Hanna P.C. "Anthrax" *The New England Journal of Medicine*, 1999, v. 341, n. 11, pp. 815-826.
Inglesby T .V., Henderson D.A., Bartlett J. G., Ascher M.S., Eitzen E., Friedlander A.M., Hauer J., McDade J., Osterholm M .T., O'Toole T., Parker G., Perl T.M., Russell P.K., Tonat K. "Anthrax as a Biological Weapon" *JAMA*, 1999, v. 281, n. 18, pp. 1735-1745.
Lee M.A., Brightwell G., Leslie D., Bird H., Hamilton A. "Fluorescent detection techniques for real-time multiplex strand specific detection of *Bacillus anthracis* using rapid PCR." *J. Appl. Microbiology*, 1999, v. 87, n. 2, pp. 218-223.
Liddington R., Pannifer A., Hanna P., Leppla S., Collier R.J. "Crystallographic studies of the anthrax lethal toxin." *J. Appl. Microbiology*, 1999, v. 87, n. 2, p. 282.
Cheun H.I., Makino S.-I., Watarai M., Shirahata T., Uchida I., Takeshi K. "A simple and sensitive detection system for Bacillus anthracis in meat and tissue." *J. Appl. Microbiology*, 2001, v. 91, n. 3, pp. 421-426.
Makino S.-I., Cheun H.I., Watarai M., Uchida I., Takeshi K. "Detection of anthrax spores from the air by real-time PCR." *Lett. Appl. Microbiology*, 2001, v. 33, pp. 237-240.
Pannifer A.D., Wong T.Y., Schwarzenbacher R., Renatus M., Petosa C., Bienkowska J., Lacyk D.B., Collierk R.J., Park S., Leppla S.H., Hanna P., Liddington R.C. "Crystal structure of the anthrax lethal factor." *Nature*, 2001, v. 414, pp. 229-233.
Yamey G. "Do we need another anthrax test?" *British Medical Journal*, 2001, v. 323, p. 1193.
Cunha B.A. "Anthrax, tularemia, plague, ebola or smallpox as agents of bioterrorism: recognition in the emergency room." *Clin. Microbiol. Infect.*, 2002, v. 8, n. 8, pp. 489-503.
Cummings R.T., Salowe S.P., Cunningham B.R., Wiltsie J., Park Y.W., Sonatore L.M., Wisniewski D., Douglas C.M., Hermes J.D., Scolnick E.M. "A peptide-based fluorescence resonance energy transfer assay for Bacillus anthracis lethal factor protease." *Proceedings of the National Academy of Sciences of the United States of America (PNAS)*, 2002, vol. 99, No. 10, pp. 6603-6606.
Dawson J. "National Labs Focus on Tools against Terrorism in Wake of Airliner and Anthrax Attacks." *Physics Today*, 2002, v. 55. No. 1, pp. 19-22.
De B.K., Bragg S.L., Sanden G.N., Wilson K.E., Diem L.A., Marston C.K., Hoffmaster A.R., Barnett G.A., Weyant R.S., Abshire T.G., Ezzell J.W., Popovic T. "Two-component direct fluorescent-antibody assay for rapid identification of Bacillus anthracis." *Emerging Infectious Diseases*, 2002, v. 8, No. 10, pp. 1060-1065.
Hoffmaster A.R., Meyer R.F., Bowen M.P., Marston C.K., Weyant R.S., Barnett G.A., Sejvar J.J., Jernigan J.A., Perkins B.A., Popovic T. "Evaluation and validation of a real-time polymerase chain reaction assay for rapid identification of Bacillus anthracis." *Emerging Infectious Diseases*, 2002, v. 8, No. 10, pp. 1178-1182.
Hughes J.M., Gerberding J.L. "Anthrax bioterrorism: lessons learned and future directions." *Emerging Infectious Diseases*, 2002, v. 8, No. 10, pp. 1013-1014.
Mock M., Roques B.P. "Progress in rapid screening of *Bacillus anthracis* lethal factor activity" *Proceedings of the National Academy of Sciences of the United States of America (PNAS)*, 2002, v. 99, n. 10, pp. 6527-6529.
Sacchi C.T., Whitney A.M., Mayer L.W., Morey R., Steigerwalt A., Boras A., Weyant R.S., Popovic T. "Sequencing of 16S rRNA Gene: a rapid tool for identification of Bacillus anthracis." *Emerging Infectious Diseases*, 2002, v. 8, No. 10, pp. 1117-1123.
Tonello F., Seveso M., Marin O., Mock M., Montecucco C. "Screening inhibitors of anthrax lethal factor." *Nature*, 2002, v. 418, p. 386.
Zhou B., Wirsching P., Janda K.D. "Human antibodies against spores of the genus *Bacillus*: a model study for detection of and protection against anthrax and the bioterrorist threat." *Proceedings of the National Academy of Sciences of the United States of America (PNAS)*, 2002, vol. 99, No. 8, pp. 5241-5246.
Sanderson W.T., Hein M.J., Taylor L., Curwin B.D., Kinnes G.M., Seitz T.A., Popovic T., Holmes H.T., Kellum M.E., McAllister S.K., Whaley D.N., Tupin E.A., Walker T., Freed J.A., Small D.S., Klusaritz B., Bridges J.H. "Surface sampling methods for bacillus anthracis spore contamination." *Emerging Infectious Diseases*, 2002, v. 8, No. 10, pp. 1145-1151.
Fowler R.H., Nordheim L. "Electron Emission in Intense Electric Fields" *Proc. R. Soc. Lond. A*, 1928, v. 119, pp. 173-181.
Spindt C.A. "A Thin-Film Field-Emission Cathode" *J. Appl. Phys.*, 1968, v. 39, n. 7, pp. 3504-3505.
Spindt C.A., Brodie I., Humphrey L., Westerberg E.R. "Physical properties of thin-film field emission cathodes with molybdenum cones." *J. Appl. Phys.*, 1976, v. 47, No. 12, pp. 5248-5263.
Spindt C.A., Holland C.E., Rosengreen A., Brodie I. "Field-Emitter Arrays for Vacuum Microelectronics" *IEEE Trans. Electron. Dev.*, 1991, v. 38, v. 10, pp. 2355-2363.

(56) References Cited

OTHER PUBLICATIONS

Spindt C.A. "Microfabricated field-emission and field-ionization sources" *Surf. Sci.*, 1992, v. 266, n. 1-3, pp. 145-154.
Brodie I., Schwoebel P.R. "Vac uum Microelectronic Devices" *Proc. IEEE*, 1994, v. 82. n. 7, pp. 1006-1034.
Okano K., Hoshina K., Iida M., Koizumi S., Inuzuka T. "Fabrication of a diamond field emitter array." *Appl. Phys. Lett.*, 1994, v. 64, No. 20, pp. 2742-2744.
Spindt C.A., Holland C.E., Schwoebel P.R., Brodie I. "Field-Emitter-Array Development for Microwave Applications" *Proc. Int. Electron Device Meeting (IEDM)*, 1995, pp. 389-392.
Ding M., Kim H., Akinwande A.I. "Observation of valence band electron emission from n-type silicon field emitter arrays." *Appl. Phys. Lett.*, 1999, v. 75, No. 6, pp. 823-825.
Hsu D.S.Y., Gray H.F. "A low-voltage, low-capacitance, vertical ruthenium-lithium-ruthenium sandwich layer thin-film-edge dispenser field emitter electron source." *Appl. Phys. Lett.*, 1999, v. 75, No. 16, pp. 2497-2499.
Jensen K.L. "Field emitter arrays for plasma and microwave source applications." *Physics of Plasmas*, 1999, v. 6, No. 5, pp. 2241-2253.
Nagao M., Utsumi K., Gotoh Y., Tsuji H., Ishikawa J., Nakatani T., Sakashita T., Betsui K. "Dependence of emission characteristics of Spindt-type field emitters on cathode material." *Appl. Surf. Sci.*, 1999, v. 146, pp. 182-186.
Temple D. "Recent progress in field emitter array development for high performance applications" *Materials Sci. and Eng.: R*, 1999, v. 24, n. 5, pp. 185-239.
Chalamala B.R., Wei Y., Rossi G., Smith B.G., Reuss R.H. "Fabrication of iridium field emitter arrays." *App. Phys. Lett.*, 2000, v. 77, No. 20, pp. 3284-3286.
Burden A.P. "Materials for field emission displays" *International Materials Reviews*, 2001, v. 46, n. 5, pp. 213-231.
Chubun N.N., Chakhovskoi A.G., Hunt C.E., Hajra M. "Fabrication and characterization of singly addressable arrays of polysilicon field-emission cathodes." *Solid-State Electron.*, 2001, v. 45, No. 6, pp. 1003-1007.
Morris D., Gilchrist B., Gallimore A. "Integration of Field Emitter Arrays into Spacecraft Systems." *Space Technology and Applications International Forum-STAIF.* 2002, pp. 393-400.
Takai M., Jarupoonphol W., Ochiai C., Yavas O., Park Y.K. "Processing of vacuum microelectronic devices by focused ion and electron beams" Appl. Phys. A, 2003, v. 76, pp. 1007-1012.
Holland K.J. "Design and fabrication of a nanotip array for a biological pathogen sensor" Thesis (M.S.), Florida International University, 2009.
Ivnitski D., Abdel-Hamid I., Atanasov P. , Wilkins E. "Biosensors for detection of pathogenic bacteria" *Biosensors and Bioelectronics*, 1999, v. 14, pp. 599-624.
Edelstein R.L., Tamanaha C.R., Sheehan P.E., Miller M.M., Baselt D.R., Whitman L.J., Colton R.J. "The BARC biosensor applied to the detection of biological warfare agents" *Biosensors and Bioelectronics* , 2000, v. 14, pp. 805-813.
Iqbal S .S., Mayo M.W., Bruno J.G., Bronk B.V., Batt C.A., Chambers J .P. "A review of molecular recognition technologies for detection of biological threat agents" *Biosensors and Bioelectronics*, 2000, v. 15, pp. 549-578.
Ivnitski D ., Abdel-Hamid I., Atanasov P., Wilkins E., Stricker S. "Application of Electrochemical Biosensors for Detection of Food Pathogenic Bacteria" *Electroanalysis*, 2000, v. 12, n. 5, pp. 317-325.
Koubova V., Brynda E., Karasova L., Skvor J., Homola J., Dostalek J., Tobiska P., Rosicky J. "Detection of foodborne pathogens using surface plasmon resonance biosensors" *Sensors and Actuators B*, 2001, v. 74, pp. 100-105.
Lester E.D., Ponce A. "An Anthrax "Smoke" Detector", *IEEE Engineering in Medicine and Biology*, 2002, v. 21, n. 5, pp. 38-42.
Ivnitski D ., O'Neil D.J., Gattuso A., Schlicht R., Calidonna M., Fisher R. "Nucleic acid approaches for detection and identification of biological warfare and infectious disease agents" *BioTechniques*, 2003, v. 35, n.4, pp. 862-869.

Leonard P ., Hearty S., Brennan J., Dunnea L., Quinn J., Chakraborty T ., O'Kennedy R. "Advances in biosensors for detection of pathogens in food and water" *Enzyme and Microbial Technology*, 2003, v. 32, pp. 3-13.
Ligler F.S., Taitt C.R., Shriver-Lake•L.C., Sapsford K.E., Shubin Y., Golden J.P. "Array biosensor for detection of toxins" *Anal. Bioanal. Chem.*, 2003, v. 377, pp. 469-477.
Lim D.V. "Detection of Microorganisms and Toxins with Evanescent Wave Fiber-Optic Biosensors" *Proc. IEEE*, 2003, v. 91, n. 6, pp. 902-907.
Shah J., Wilkins E. "Electrochemical Biosensors for Detection of Biological Warfare Agents" *Electroanalysis*, 2003, v. 15, n. 3, pp. 157-167.
Sotiropoulou S., Chaniotakis N.A. "Carbon nanotube array-based biosensor" *Anal. Bioanal. Chem.*, 2003, v. 375, pp. 103-105.
Lester E.D., Bearman G., Ponce A. "A second-generation anthrax "smoke detector"" *IEEE Engineering in Medicine and Biology Magazine*, 2004, v. 23, n. 1, pp. 130-135.
Committee on Materials and Manufacturing Processes for Advanced Sensors "Sensor Systems for Biological Agent Attacks: Protecting Buildings and Military Bases" The National Academies Press, Washington, D.C., 2005.
Floriano P .N., Christodoulides N., Romanovicz D., Bernard B., Simmons G.W., Cavella M., McDevitt J.T. "Membrane-based on-line optical analysis system for rapid detection of bacteria and spores" *Biosensors and Bioelectronics*, 2005, v. 20, pp. 2079-2088.
Lim D.V., Simpson J.M., Kearns E.A., Kramer M.F. "Current and Developing Technologies for Monitoring Agents of Bioterrorism and Biowarfare" *Clinical Microbiology Reviews*, 2005, v. 18, n. 4, pp. 583-607.
Mathew F .P., Alocilja E.C. "Porous silicon-based biosensor for pathogen detection" *Biosensors and Bioelectronics*, 2005, v. 20, pp. 1656-1661.
Radke S .M., Alocilja E.C. "A high density microelectrode array biosensor for detection of *E. coli* O157:H7" *Biosensors and Bioelectronics*, 2005, v. 20, pp. 1662-1667.
Song L., Ahn S., Walt D.R. "Detecting Biological Warfare Agents" *Emerging Infectious Diseases*, 2005, v. 11, n. 10, pp. 1629-1632.
Wang J. "Carbon-Nanotube Based Electrochemical Biosensors: A Review" Electroanalysis, 2005, v. 17, n. 1, pp. 7-14.
Murphy L. "Biosensors and bioelectrochemistry" *Current Opinion in Chemical Biology*, 2006, v. 10, pp. 77-184.
Subramanian A., Irudayaraj J., Ryan T. "Mono and dithiol surfaces on surface plasmon resonance biosensors for detection of *Staphylococcus aureus*" *Sensors and Actuators B*, 2006, v. 114, pp. 192-198.
Arumugam P .U., Chen H., Cassell A.M., Li J. "Dielectrophoretic Trapping of Single Bacteria at Carbon Nanofiber Nanoelectrode Arrays" *J. Phys. Chem. A*, 2007, v. 111, n. 49, pp. 12772-12777.
Cousins D., Campbell S.D. "Protecting Buildings against Airborne Contamination" *Lincoln Laboratory Journal*, 2007, v. 17, n. 1, pp. 131-151.
Lazcka O ., Del Campo F.J, Munoz F.X. "Pathogen detection: A perspective of traditional methods and biosensors" Biosensors and Bioelectronics, 2007, v. 22, pp. 1205-1217.
Petrovick M.S., Harper J.D., Nargi F.E., Schwoebel E.D., Hennessy M.C., Rider T.H., Hollis M.A. "Rapid Sensors for Biological-Agent Identification" *Lincoln Laboratory Journal*, 2007, v. 17, n. 1, pp. 63-84.
Yung P.T., Lester E.D., Bearman G., Ponce A. "An Automated Front-End Monitor for Anthrax Surveillance Systems Based on the Rapid Detection of Airborne Endospores" *Biotechnology and Bioengineering*, 2007, v . 98, n. 4, pp. 864-871.
Drevinek M . "Mass spectrometry—a powerful tool in rapid identification of biological warfare agents" *Timisoara Medical J.*, 2008, v. 58, n. 1-2, pp. 26-30.
Sapsford K .E., Bradburne C., Delehanty J.B., Medintz I.L. "Sensors for detecting biological agents" *Materials Today*, 2008, v. 11, n. 3, pp. 38-49.
Koh J., Yi M., Lee B.Y., Kim T.H., Lee J., Jhon Y.M., Hong S. "Directed assembly of carbon nanotubes on soft substrates for use as a flexible biosensor array" *Nanotechnology*, 2008, v. 19, p. 505502.

(56) References Cited

OTHER PUBLICATIONS

Zoua Y., Xiang C., Suna L., Xua F. "Amperometric glucose biosensor prepared with biocompatible material and carbon nanotube by layer-by-layer self-assembly technique" *Electrochimica Acta*, 2008, v. 53, pp. 4089-4095.

Regan J.F, Makarewicz A.J., Hindson B.J., Metz T.R., Gutierrez D.M., Corzett T.H., Hadley D.R., Mahnke R.C., Henderer B.D., Breneman IV J.W., Weisgraber T.H., Dzenitis J.M."Environmental Monitoring for Biological Threat Agents Using the Autonomous Pathogen Detection System with Multiplexed Polymerase Chain ReactionY.V." *Anal. Chem.*, 2008, v. 80, n. 19, pp. 7422-7429.

Webster, M.S., Timoshkin, I.V., MacGregor S.J., Mattey M. "Computer aided modelling of an interdigitated microelectrode array impedance biosensor for the detection of bacteria" *IEEE Trans. on Dielectrics and Electrical Insulation*, 2009, v. 16, n. 5, pp. 1356-1363.

Theegala C.S., Small D.D., Monroe W.T. "Oxygen electrode-based single antibody amperometric biosensor for qualitative detection of *E. coli* and bacteria in water." *J. of Environmental Science and Health*, Part A, 2008, v. 43, n. 5, pp. 478-487.

Tecon R., van der Meer J.R. "Bacterial Biosensors for Measuring Availability of Environmental Pollutants" *Sensors*, 2008, v. 8, n. 7, pp. 4062-4080.

Rowe C.A., Tender L.M., Feldstein M.J., Golden J.P., Scruggs S.B., MacCraith B.D., Cras J.J., and Ligler F.S. "Array Biosensor for Simultaneous Identification of Bacterial, Viral, and Protein Analytes" *Anal. Chem.*, 1999, v. 71, pp. 3846-3852.

Kradtap S., Wijayawardhana C.A., Schlueter K.T., Halsall H.B., Heineman W.R. " "Bugbead": an artificial microorganism model used as a harmless simulant for pathogenic microorganisms" *Analytica Chimica Acta*, 2001, v. 444, n. 1, pp. 13-26.

Arakawa E.T., Lavrik N.V., Datskos P.G. "Detection of anthrax simulants with microcalorimetric spectroscopy: *Bacillus subtilis* and *Bacillus cereus* spores" *Appl. Optics*, 2003, v. 42, n. 10, pp. 1757-1762.

Farrell S., Halsall H.B., Heineman W.R. "Immunoassay for *B. globigii* spores as a model for detecting B. anthracis spores in finished water" *Analyst*, 2005, v. 130, pp. 489-497.

Farrell S., Halsall H.B., Heineman W.R. "*Bacillus globigii* Bugbeads: A Model Simulant of a Bacterial Spore" *Anal. Chem.*, 2005, v. 77, n. 2, pp. 549-555.

Chichester K.D., Silcott D.B., Colyer C.L. "Analysis of *Bacillus globigii* spores by CE" *Electrophoresis*, 2008, v. 29, pp. 641-651.

Uskokovic V. "Isn't self-assembly a misnomer? Multi-disciplinary arguments in favor of co-assembly" *Adv. Colloid Interface Sci.*, 2008, v. 141, n. 1, pp. 37-47.

Rehse, S.J., Diedrich, J., Palchaudhuri, S. "Identification and discrimination of *Pseudomonas aeruginosa* bacteria grown in blood and bile by laser-induced breakdown spectroscopy" *Spectrochim. Acta Part B At. Spectrosc.*, 2007, v. 62, n. 10, pp. 1169-1176.

Miao J., Hodgson K. O., Ishikawa T., Larabell C. A., LeGros M. A., Nishino Y. "Imaging whole *Escherichia coli* bacteria by using single-particle x-ray diffraction" *Proc. Natl. Acad. Sci. USA*, 2003, v. 100, n. 1, pp. 110-112.

Rajeshwari H., Nagveni S., Oli A., Parashar D., Chandrakanth K. R. "Morphological changes of *Klebsiella pneumoniae* in response to Cefotaxime: a scanning electron microscope study." *World J. Microbiol. Biotechnol.*, 2009, v. 25 , pp. 2263-2266.

Touhami A., Jericho M. H., Beveridge T. J. "Atomic Force Microscopy of Cell Growth and Division in *Staphylococcus aureus.*" *J. of Bacteriology*, 2004, v. 186, No. 11, pp. 3286-3295.

Bradley D.E. "The Length of the Filamentous *Pseudomonas aeruginosa* Bacteriophage Pf" *J. gen. Virol.*, 1973, v. 20, pp. 249-252.

Bossolan, N.R.S., Godinho, M.J.L.2, Volpon, A.G.T. "Growth and starvation of a strain of *Klebsiella pneumoniae* isolated from a Brazilian oil formation" World J. Microbiol. Biotechnol., 2005, v. 21, n. 8-9, pp. 1471-1475.

\* cited by examiner

NANOTIP SENSOR

This application claims the benefit of priority under 35 U.S.C. § 120 to U.S. patent application Ser. No. 13/101,324, filed May 5, 2011, entitled "Nanotip Sensor," which claims the benefit of priority under 35 U.S.C. § 119 to U.S. Provisional Patent Application No. 61/332,130, entitled "Nanotip Array Based Biological Pathogen Sensor Using Antigens" filed on May 6, 2010, and to U.S. Provisional Patent Application No. 61/332,131, entitled "Electric Field Driven Self Adsorbing Biosensor" filed on May 6, 2010. The teachings and disclosures of each are hereby incorporated by reference herein in their entireties and for all purposes.

TECHNOLOGICAL FIELD

This disclosure is directed to a sensor for detecting chemical or biological particulates, and in particular, for detecting pathogens.

BACKGROUND

Currently known techniques to detect and/or identify pathogens and other particulates suffer from several limitations and drawbacks. For example, size or mass spectrometry techniques generate an undesirable number of false positives, and require frequent cleaning and replacement of filtration elements. Furthermore, depending on the binder or host media used as a carrier, a positive reading may indicate one of several possible pathogens. In practice, the set of possible matches may be large enough to require foreknowledge of the type of carrier in use, which generally cannot be guaranteed, especially in small-scale scenarios.

Microbiological culturing techniques generally require a significant amount of time for culturing (e.g., 24 to 72 hours), and additionally, may incur significant costs due to required media and inspections conducted by trained professionals. Polymerase chain reaction (PCR) assays reduce the time of detection to few hours, and generally lead to fewer false positives and missed positives (false negatives). On the other hand, the requirement of PCR assay techniques for reagents and culture media, patented chemistries, and the still-significant detection time leads to requirements for support of highly skilled personnel and specialized transport, thus incurring significant costs.

All of the above mentioned techniques share the common challenge of safely, rapidly, and cost-effectively disposing of hazardous outputs generated by the detection techniques. Typically, concentrated germ/virus cultures are produced as an end product to these techniques, and disposal of these concentrated cultures is both costly and dangerous.

SUMMARY OF THE DISCLOSURE

In an embodiment, a sensor for detecting particulates in a sample may include a first electrical contact for connecting to a variable voltage source, a second electrical contact for connecting to a current measuring device, and a plurality of nanotips. Each nanotip of the plurality of nanotips may be electrically connected to the first electrical contact and to the second electrical contact, and each nanotip may include a cathode, an anode, and a gap between the cathode and the anode. The gap of at least one nanotip in the plurality of nanotips may be configured to be bridged by one or more particulates to form an electrical circuit. The one or more particulates may include chemical particulates and/or biological particulates. The formed electrical circuit may have a corresponding current versus voltage (I-V) characteristic that identifies the type or species of bridging particulate.

In an embodiment, a system for detecting particulates in a sample may include a variable voltage source, a current measuring device, and a sensor electrically coupled to the variable voltage source and electrically coupled to the current measuring device. The sensor may include a plurality of nanotips, with each nanotip including a cathode, an anode, and a gap between the cathode and the anode. The gap of at least one nanotip in the plurality of nanotips may be configured to be bridged by one or more particulates to form an electrical circuit. The one more particulates may be chemical particulates and/or biological particulates. The formed electrical circuit may have a corresponding current versus voltage (I-V) characteristic that identifies the specific bridging particulate(s). The system may include, in some embodiments, a chamber enclosing the sensor. In some embodiments, the system may include a vacuum system in fluid connection with the chamber, and/or a variable light source aimed to irradiate photonic radiation on the sensor.

In an embodiment, a method of using a sensor to detect particulates in a sample may include exposing the sensor to the sample. The sensor may include a plurality of nanotips that may be electrically connected to a variable voltage source and to a current measuring device. The method may include determining a conductive spectrum of the sample based on a set of particulates included in the sample, where each particulate of the set of particulates is in physical connection with a respective nanotip of the plurality of nanotips to form a respective electrical circuit. The method may also include comparing the conductive spectrum of the sample with one or more particulate profiles that are stored in a database of particulate profiles, where each particulate profile in the database corresponds to a conductive spectrum of a respective identified particulate. The method may include detecting a presence of a specific particulate in the sample based on the comparison of the conductive spectrum of the sample and the conductive spectrums of the one or more stored particulate profiles. In some embodiments, the sample may be physically filtered prior to exposing the sensor to the sample. In some embodiments, the sensor may be electronically cleaned after detecting the presence of the specific particulate.

DETAILED DESCRIPTION

Nanotip Sensor System

Figure 1:
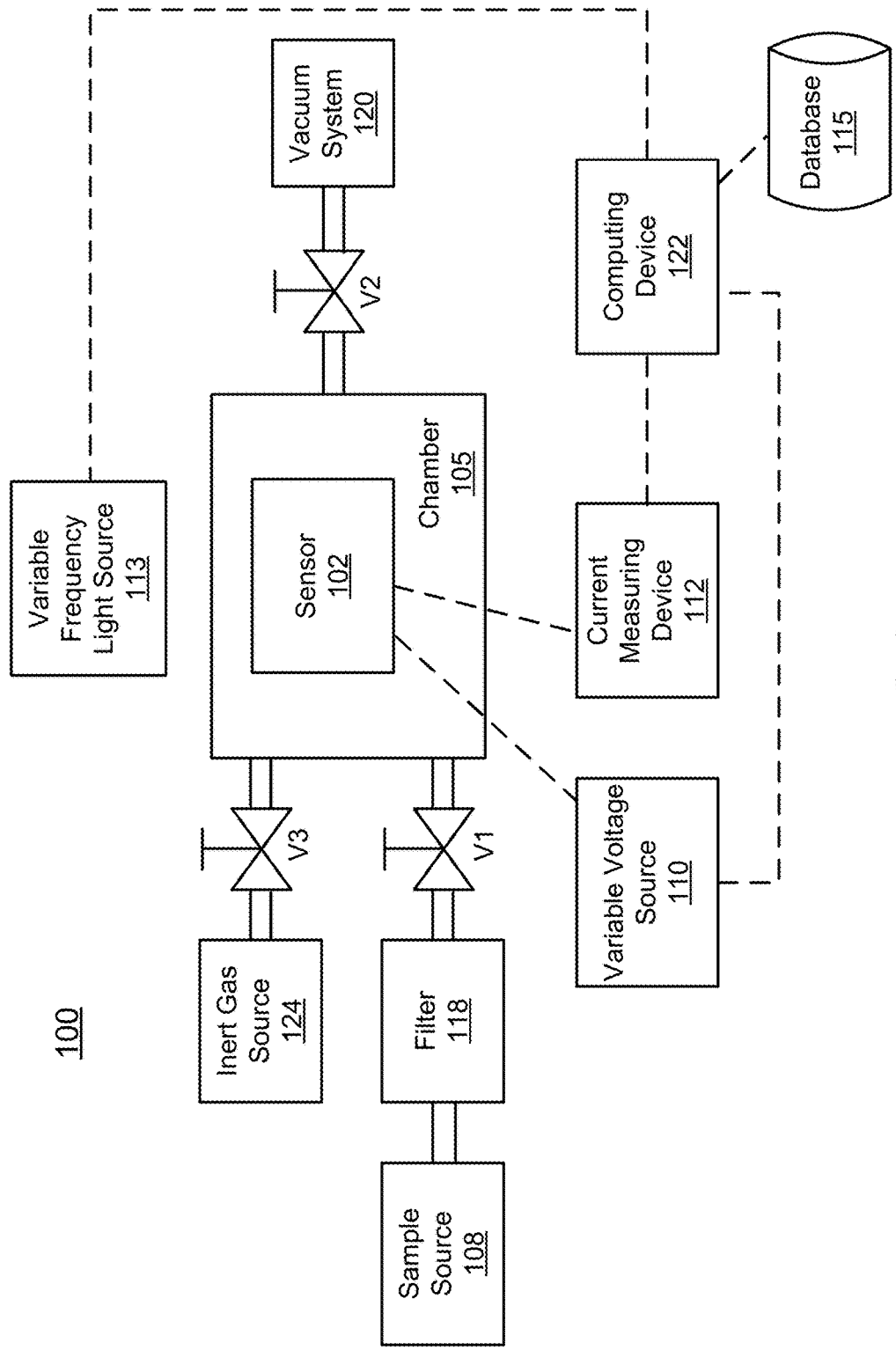
FIG. 1 is an embodiment of a system for detecting or sensing biological or chemical particulates in a sample.

FIG. 1 is block diagram of an embodiment of a system 100 including a sensor 102 for sensing or detecting biological and/or chemical particulates in a sample. The sample may be of liquid form or gas form, and may contain any number, types or species of biological and/or chemical particulates. As used herein, the term "particulate" refers generally to a compound, molecule, ion, salt, enzyme, nanoparticle, environmental contaminant, toxin, fatty acid, steroid, hormone, carbohydrate, amino acid, peptide, polypeptide, protein or other amino acid polymer, microbe, virus or any other agent. The term "particulate" broadly encompasses both "biological particulate" and "chemical particulate" as these terms are defined herein.

The term "biological particulate," as used herein, refers to any material (e.g., cell, nucleic acid (RNA, DNA), protein, enzyme, etc.) derived from a living organism, such as bacteria, a virus, a parasite or a fungus. In some embodiments, the biological particulate comprises one or more bacteria. Exemplary bacteria contemplated for detection using the system 100 and/or the sensor 102 described herein include Gram positive bacteria and Gram negative bacteria and mixtures thereof.

As used herein, the term "Gram-positive bacteria" refer to those bacteria that are stained dark blue or violet by Gram staining, in contrast to Gram-negative bacteria, which cannot retain the stain, instead taking up the counterstain and appearing red or pink. The stain is caused by a high amount of peptidoglycan in the cell wall, which typically, but not always, lacks the secondary membrane and lipopolysaccharide layer found in Gram-negative bacteria. Gram-positive bacteria include many well-known genera such as *Bacillus, Listeria, Staphylococcus, Streptococcus, Enterococcus,* and *Clostridium*. Gram-positive bacteria may also include the Mollicutes, and bacteria such as *Mycoplasma*, which lack cell walls and so cannot be stained by Gram, but are derived from such forms.

As used herein, the term "Gram-negative bacteria" refer to the phylum of proteobacteria, which have an outer membrane composed largely of lipopolysaccharides. All proteobacteria are gram negative, and include, but are not limited to *Escherichia coli, Salmonella,* other Enterobacteriaceae, *Pseudomonas, Burkholderi, Moraxella, Helicobacter, Stenotrophomonas, Bdellovibrio,* acetic acid bacteria, and *Legionella*. Other notable groups of gram negative bacteria include *Haemophilus influenzae,* the cyanobacteria, spirochaetes, green sulfur and green non-sulfur bacteria. The pathogenic capability of gram negative bacteria is usually associated with components of the bacterial cell wall, in particular the lipopolysaccharide (also known as LPS or endotoxin) layer.

In some embodiments, the Gram positive bacteria is a Gram positive cocci (spherical shaped) bacteria. Non-limiting examples of Gram-positive cocci bacteria include, but are not limited to, members of the *Staphylococcus* genus (e.g., *Staphylococcus aureus, Staphylococcus epidermidis, S. haemolyticus, S. hominis, S. exotoxin* and *S. saprophyticus*); the *Streptococcus* genus (e.g., *Streptococcus pyogenes, Streptococcus pneumoniae, Streptococcus agalactia, Streptococcus mutans*); the *Entenococcus* genus (e.g., *E. faecium, E. faecalis, E. avium, E. casseliflavus, E. durans, E. gallinarum, E. dispar, E. hirae, E. flavescens, E. mundtii, E. solitanius, E. raffinosus); Peptostreptococcus* sp. (e.g. *Peptostreptococcus magnus, Peptostreptococcus asaccharolyticus, Peptostreptococcus anaerobius, Peptostreptococcus prevotii,* and *Peptostreptococcus micros.); Veillonella;* catalase-negative gram-positive cocci including viridans streptococcal species such as *S. mutans* and *S. sobrinus, S. salivanius* and *S. vestibularis, S. bovis, S. pneumoniae, S. sanguis* and *S. gordonii, S. mitis* and *S. oralis, S. anginosus, S. constellatus,* and *S. intermedius, S. milleni, S. MG-intermedius, S. anginosus-constellatus; Abiotrophia* and *Granulicatella;* the *Gemella* genus (e.g., *Gemella haemolysans, Gemella morbillorum, Gemella bergeniae, Gemella sanguinis); Rothia mucilaginosa; Aerococcus* (e.g., *Aerococcus vinidans, A. uninae); Lactococcus* (e.g., *L. lactis, L.s garviae); Helcococcus*(e.g., *Helcococcus kunzii);* the genus *Globicatella* (e.g., *Globicatella sanguis); Facklamia; lgnavigranum; Dolosicoccus; Dolosigranulum* (e.g., *Dolosigranulum pigrum); Alloiococcus* (e.g., *A. otitidis); Vagococcus* (e.g., *V. fluvialis* and *V. salmoninarum); Leuconostoc* (e.g., *L. citreum, L. lactis, L. mesenteroides, L. pseudomesenteroides, L. argentinum* and *L. paramesenteroides); Pediococcus* (e.g., *P. acidilactici* and *P. pentosaceus), Tetragenococcus* (e.g., *Tetragenococcus halophilus),* as well as other clinically-relevant Gram-positive cocci well known in the art.

In some embodiments, the Gram positive bacteria is a Gram positive bacilli (rod shaped) bacteria including, but not limited to, *Lactobacillus* sp., *Clostridium* sp. (e.g., *Clostridium botulinum, Clostridium botulinum, Clostnidium perfringens, Clostnidium tetani); Actinomyces* sp. (e.g., *A. Israeli), Bifidobacterium* (e.g., *B. dentium), Nocardia* sp, *Listeria monocytogenes, Corynebacterium diptheniae, Propionibactenium acnes; Bacillus anthracis,* and *Erysipelothnix rhusiopathiae,* as well as other clinically-relevant Gram-positive bacilli well known in the art.

Non-limiting examples of Gram-Negative bacteria include, but are not limited to: *Klebsiella* (e.g., *K. pneumoniae); Citrobacter; Serratia* (e.g., *S. marascens); Enterobacter; Proteus* (*P. mirabilis, P. vulgaris,* and *P. myxofa-*

*ciens*); *Morganella* (e.g., *M. morganii*); *Providencia* (*P. rettgeri*, *P. alcalifaciens*, and *P. stuartii*); *Salmonella* sp. (e.g., *S. typhi*, *S. paratyphi* A, B *S. schottmuelleri*, *S. hirschfeldii*, *S. enteritidis*, *S. typhimurium*, *S. heidelberg*, *S. newport*, *S. infantis*, *S. agona*, *S. montevideo*, and *S. saintpaul*); the *Shigella* genus (e.g., *S. fiexneri*, *S. sonnei*, *S. boydii*, *S. dysenteriae*); the *Haemophilus* genus (e.g., *H. influenzae*); *Brucella* sp. (e.g., *Brucella abortus*, *B. melitensis*, *B. suis*, *B. canis*); *Francisella tularensis*; *Vibrio* sp. (e.g., *V. cholerae*, *V. parahaemolyticus*, *V. mimicus*, *V. alginolyticus*, *V. hollisae*, *V. vulnificus*); *Yersinia* sp. (e.g., *Y. pestis*, *Y. enterocolitica*); *Burkholderia* sp. (e.g., *B. pseudomallei*, *B. cepacia*); *Campylobacter* sp. (e.g., *C. fetus*, *C. jejuni*, *C. coli*); *Helicobacter pylori*; *Acinetobacter baumannii*, *Actinobacillus actinomycetemcomitans*, *Bordetella pertussis*; *Capnocytophaga*; *Cardiobacterium hominis*; *Eikenella corrodens*; *Kingella kingii*; *Legionella pneumophila*; *Pasteurella multicida*; *Acinetobacter* sp.; *Xanthomonas maltophilia*; *Aeromonas*; *Plesiomonas shigelloides*, *Neisseria* sp. (e.g., *N. gonorrhoeae* and *N. meningitidis*), *Moraxella* (*Branhamella*) *catarrhalis*, and *Veillonella* sp. (e.g., *Veillonella parvula*).

In some embodiments, the biological particulate is a virus. Exemplary viruses contemplated for detection using the system 100 and/or the sensor 102 described herein include, but are not limited to, Ebola virus, Niphah virus, Hantavirus, Marburg virus, Variola vera (small pox), Machupo virus, Lassa virus, Herpes simplex type 1 (HSV-1), HSV-2, Varicella zoster virus (HSV-3), Cytomegalovirus virus (HSV-5), Human herpes virus type 6, 7, Epstein Barr virus (HSV-4), Human herpes virus type 8, Variola virus, Molluscum contagiousum virus, Human adenovirus, Papillomavirus, BK virus, JC virus, Human parvovirus (B19), Rhinovirus, Hepatitis A, Rubella virus, Eastern equine encephalitis virus, Human herpes virus type 8, Yellow fever virus, Dengue virus, West Nile virus, Hepatitis C virus, Human coronavirus, Norwalk virus, Paramoxyviruses, Respiratory syncitial virus (RSV), Human parainfluenza virus 1, Rabies virus, Influenza A, Influenza B, Influenza C, Sin Nombre virus and other clinically relevant viruses.

In still other embodiments, the biological particulate is a fungus. Exemplary fungi contemplated for detection using the system 100 and/or the sensor 102 described herein include, but are not limited to, *Cryptococcus* species (*C. neoformans*, *C. gattii*, *C. laurentii* and *C. albidus*), *Candida* species, *Aspergillus* species (e.g., *A. fumigatus*, *A. clavatus* and *A. flavus*), *Histoplasma capsulatum*, *Pneumocystis jirovecii* and *Stachbotrys chartarum* any other clinically relevant fungi.

In some embodiments, the biological particulate is a nucleic acid or nucleic acid fragment derived from a bacteria, a virus, a parasite or a fungus. The term "nucleic acid" as used herein refers to DNA, RNA and fragments thereof. In most cases, naturally occurring DNA molecules are double-stranded and RNA molecules are single-stranded. Double-stranded nucleic acids are made up of complementary sequences, in which extensive Watson-Crick base pairing results in the formation of a highly repeated and quite uniform double-helical three-dimensional structure. In contrast, single-stranded RNA and DNA molecules are not constrained to a regular double helix, and can adopt highly complex three-dimensional structures that are based on short stretches of intramolecular base-paired sequences that include both Watson-Crick and noncanonical base pairs, as well as a wide range of complex tertiary interactions. Nucleic acid molecules are usually unbranched, and may occur as linear and circular molecules. For example, bacterial chromosomes, plasmids, mitochondrial DNA and chloroplast DNA are usually circular double-stranded DNA molecules, while chromosomes of the eukaryotic nucleus are usually linear double-stranded DNA molecules. Most RNA molecules are linear, single-stranded molecules, but both circular and branched molecules can result from RNA splicing reactions.

The term "chemical particulate," as used herein, broadly refers to any organic or inorganic substance or compound. Exemplary chemical substances contemplated for detection using the system 100 and/or the sensor 102 described herein include, but are not limited to, ricin, abrin, botulinum toxin, saxitoxin, arsines, cyanogens chloride, hydrogen cyanide, lewisite, phosgene oxime, sulfur mustard gas, nitrogen mustard gas, tabun, sarin, soman, cyclosarin, chloropicrin, chlorine, diphosgene, dimethyl methylphosphorate agent 15, KOLOKOL-1, 2-chlorobenzalmalononitrile (tear gas), phenacyl chloride (mace), dibenzoxazepine, novichok gas, dioxins, agent orange and napalm, fly ash, radioisotopic fallout, and soot, although other chemical substances may also be contemplated for detection.

The term "pathogen," as used herein, refers to cell(s) derived from a bacteria, a virus, or a fungus that is (are) capable of infecting and causing disease in a mammalian host, as well as producing infection-related symptoms in the infected host, such as fever or other signs of inflammation, intestinal symptoms, respiratory symptoms, dehydration, and the like.

In FIG. 1, the dashed lines represent electrical connections and the double lines represent fluid, gas or vapor connections. Valves controlling the fluid, gas or vapor connections are designated by V1, V2 and V3.

The system 100 shown in FIG. 1 does not require chemical reactions and/or biological cultures in order to sense or detect various particulates. That is, detection and/or identification of specific particulates by the system 100 is performed independently of both chemical reactions and biological cultures. Instead, the system 100 may include one or more electrical sensors 102 for detecting one or more specific particulates. The one or more sensors 102 may be enclosed in a chamber 105 that is configured to contain a liquid sample or a gas sample so that the sensor 102 is exposed to the sample. FIG. 1 includes a single block representing the sensor 102, however, it is understood that the block 102 may represent more than one electrical sensor 102.

The sensor 102 may include a set of electrical nanotips to effect detection and identification of particulates. Each nanotip may be electrically biased so that its cathode acts as an electrostatic precipitator and its anode acts as a second contact. In an embodiment, the cathode and the anode may be positioned in a tip and ring configuration, so that the tip may serve as the cathode and the ring surrounding the tip may serve as the anode. In other embodiments, the tip may serve as the anode and the ring surrounding the tip may serve as the cathode. For ease of discussion, the present disclosure describes the embodiment in which the tip of the nanotip serves as the cathode and the ring serves as the anode, although it is understood that the concepts presented herein apply equally to other cathode/anode configurations.

A source 108 of the sample may be in fluid, gas or vapor communication with the chamber 105. The communication between the sample source 108 and the chamber 105 may be controlled by a valve V1. Using the valve V1, a flow or stream of particulates from the source 108 may be released into the chamber 105, or otherwise diverted over the nanotips of the sensor 102 while the nanotips are biased. Due to the bias, one or more particulates in the flow or stream may be adsorbed to the cathode (in this example, to the tip) of at least some of the nanotips of the sensor. The term "adsorption" as used herein is given its ordinary meaning in referring to the physical adherence, connection, or association of one substance (e.g., a particulate in the sample stream or flow) to the surface of another substance (e.g., the cathode of the nanotip). "Adsorption" may encompass any physical adherence, connection, or association between a particulate and a nanotip, including ionic complexing, electrostatic complexing, chelation, hydrogen bonding, ion-dipole, dipole/dipole, Van Der Waals forces, surface potential bonding, and combinations thereof. The term "desorption" as used herein refers to the converse process in which an adsorbed substance (e.g., a particulate) is released from the cathode or tip.

The diversion of the sample may result in a statistically complete loading of the nanotips with adsorbed, dissociated particulates within seconds depending on flow rates, bias, and the physical design (e.g., shape and/or size) of the chamber 105. Some of the adsorbed particulates may each form a respective electrical circuit by spanning or bridging the gap between the cathode and an anode of a respective nanotip. Similar particulates may be likely to attach in similar directions, thus leading to a statistical probability of an oriented adsorption, e.g., self-assembly.

Particulates that are adsorbed or that are electrostatically precipitated to the nanotips may be identified based on their respective conductive spectrums (e.g., a current versus applied voltage characteristic). In an embodiment, a range of voltages generated by a variable voltage source 110 may be applied to the sensor 102, and thus may be applied to any formed electrical circuits and their respective, adsorbed particulates. The voltage produced by the variable voltage source 110 may be sweepable or otherwise adjustable or selectable across a range or plurality of voltages. Based on the resulting flow of current through the electrical circuits as measured by a current measuring device 112, the conductive spectrum of the sample may be determined and may be compared with a database 115 of known conductive spectrums to detect and identify particulates that are present in the sample.

In some embodiments, in addition to sweeping through a range of voltages, a range of photonic wavelengths may also be irradiated onto the sensor 102, its nanotips, and any adsorbed particulates. The range or plurality of photonic wavelengths may be generated, for example, by a variable frequency light source 113 that is configured or positioned to irradiate light across the nanotips of the sensor 102. The light may include wavelengths ranging from the far-infrared (far-IR) spectrum to the far-ultraviolet (far-UV) spectrum, or some subset of wavelengths thereof. The light source 113 may produce a light whose wavelength may be sweepable or otherwise adjustable or selectable across a range or plurality of wavelengths. In some embodiments, the light source 113 may produce a monochromatic light. A conductive-photonic current response of the electrical circuits resulting from the combination of the swept voltages and swept photonic wavelengths may be measured by the current measuring device 112 to determine a conductive-photonic spectrum of the sample. The conductive-photonic spectrum of the sample may be compared with a database 115 of known conductive-photonic spectrums to identify particulates that are present in the sample.

In some embodiments, the plurality of nanotips on the sensor 100 may be arranged in an array. In some embodiments, a specificity of particulate detection or identification by the system 100 may be increased by increasing the number of nanotips. As the number of nanotips increases, the concentration of potential target particulates may increase, thus increasing the probability of an increase in the numbers of adsorbed particulates. The increase in the numbers of adsorbed particulates may result in a stronger generated signal for detection. A single sensor may include a plurality of sub-arrays, each of which may be designed to adsorb and detect/identify particulates of differing types, sizes, and/or species.

In some embodiments, specificity of the system 100 may be alternatively or additionally raised by priming the plurality of nanotips with target particulate-specific antibodies or nucleic acid fragments, hence increasing a binding probability of target particulates. Furthermore, in some embodiments, a filter 118 may separate a carrier of the sample (pollen, yeast, oil, emulsifier etc.) or other undesired particulates from target particulates, thus increasing the concentration of potential target particulates in the sample stream or flow to which the sensor 102 is exposed.

Figure 2:
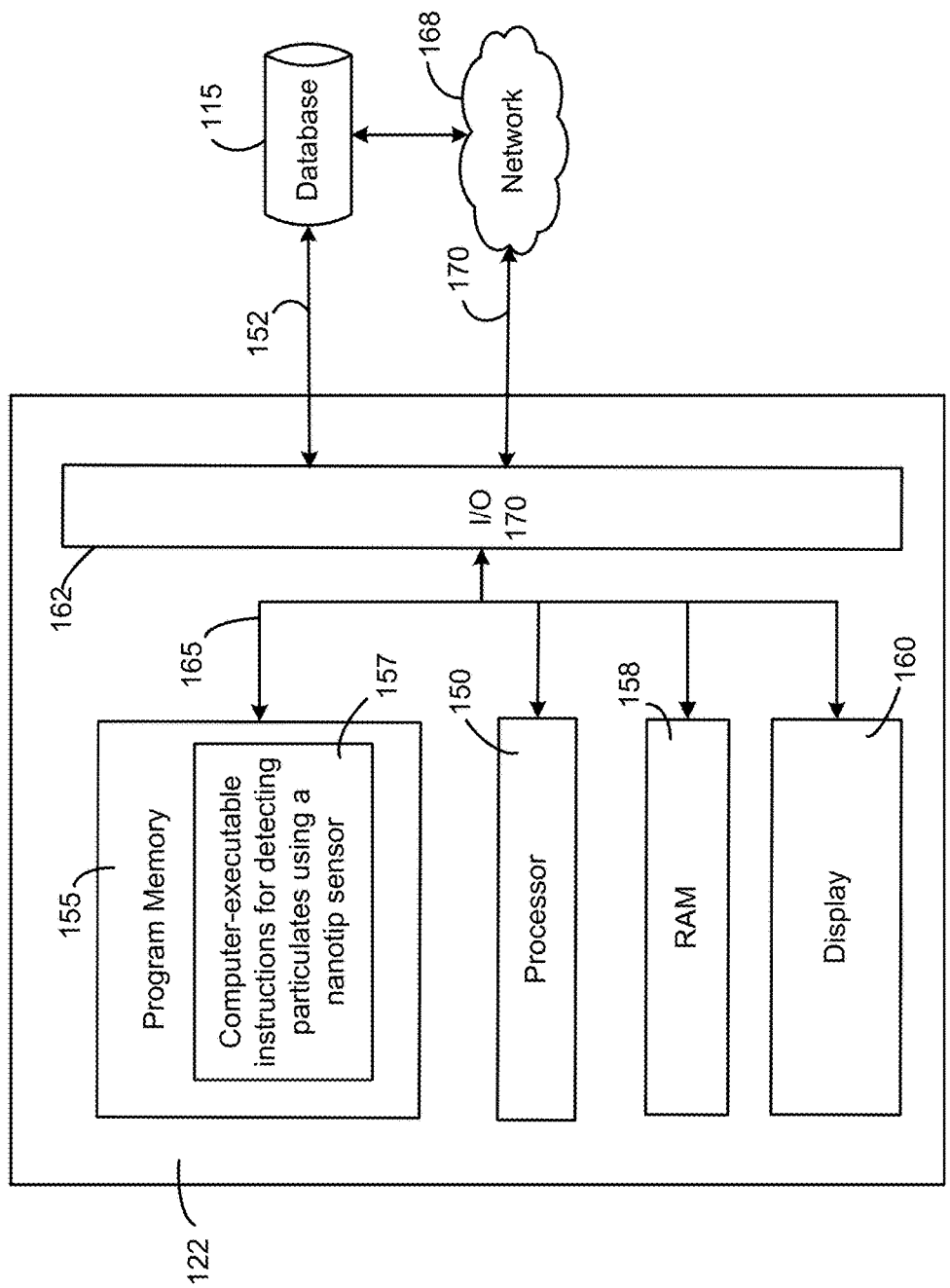
FIG. 2 is a block diagram of an example computing device that may be used in the system of FIG. 1.

In some embodiments, the variable voltage source 110 and/or the variable frequency light source 112 may be controlled by a computing device 122 (e.g., a workstation, a laptop, a tablet, etc.). FIG. 2 illustrates an exemplary embodiment of a computing device 122 that may be used in the system 100 of FIG. 1. For the sake of illustration, a simplified block diagram of a computer is used to illustrate the principles of the instant disclosure. However, such principles apply equally to other electronic devices, including, but not limited to, cellular telephones, personal digital assistants, smart phones or smart devices, client and/or server computing systems, and cloud computing systems, to name a few. The computing device 122 may have a processor 150 that may be operatively connected to the database or storage entity 115 via a link 152. Link 152 may be as simple as a memory access function, or it may be a wired, wireless, or multi-stage connection through a network. Many types of links are known in the art of networking and are possible.

The database or storage entity 115 may be contained in the same physical entity as the computing device 122, or it may be a separate, distinct, physical local or remote entity that is accessible by the computing device 122. Database or storage entity 115 may be a database on a computer, a server, a network, a computing cloud or other computing device(s), or the database or storage entity 115 may be a storage device such as a hard drive, disk, mass storage device, or the like. Many types of storage entities are known in the art of data storage and may operate with the disclosure of this application. It should be noted that, while not shown, additional, multiple databases/storage entities may be linked to the computing device 122 in a known manner. The database or storage entity 115 may include known conductive spectrums respectively corresponding to known, identified chemical or biological particulates. In some embodiments, the database or storage entity 115 may include known conductive-photonic spectrums respectively corresponding to known, identified chemical or biological particulates. These and other types of relevant data may be stored on a single database or storage entity 115 or across multiple storage entities.

The computing device 122 may include the processor 150 (may be called a microcontroller or a microprocessor) for executing computer executable instructions 157 for detecting or identifying particulates using a nanotip sensor, a program memory 155 for permanently storing the computer-executable instructions 157 and data related to the computer executable instructions 157, a random-access memory (RAM) 158 for temporarily storing data related to the computer executable instructions 157, a display 160 and an input/output (I/O) circuit 162, all of which may be interconnected via an address/data bus 165. In particular, the computer-executable instructions 157 may be executable to control the variable voltage source 110 to sweep a range of voltages, to (optionally) control the variable frequency light source 112 to sweep a range of wavelengths, and to collect and store current response data measured by the current measuring device 112. The computer-executable instructions 157 may be executable to determine conductive spectrums and/or to determine conductive-photonic spectrums based on the sweeping and the collected data by comparing the determined spectrums against spectrums of known particulates stored in the database 115. In some embodiments, the computer-executable instructions 157 may include instructions for algorithms to identify conductive spectrums that are "new" or not found in the database 115, e.g., "learning algorithms." For instance, a learning algorithm included in the computer-executable instructions 157 may detect an unrecognized profile, and may characterize the unrecognized profile into a new profile for addition to the database 115. As such, the system 100 may more effectively detect and/or identify mixed adsorbates that are present in a sample.

It should be appreciated that although only one microprocessor 150 is shown, the computing device 122 may include multiple microprocessors 150. Similarly, although FIG. 2 illustrates only one RAM 158 and one program memory 155, the memory of the computing device 122 may include multiple RAMs 158 and/or multiple program memories 155. Also, although the I/O circuit 162 is shown as a single block, it should be appreciated that the I/O circuit 162 may include a number of different types of I/O circuits. The RAM(s) 158 and program memory (memories) 155 may be implemented as semiconductor memories, magnetically readable memories, and/or optically readable memories, for example.

The computing device 122 may also be operatively connected to a network 168 via a link 170. The network 168 may be a private network, such as a LAN or virtual private network, the network 168 may be a public network such as the Internet, or the network 168 may be a combination of any number of private and/or public networks. Similar to link 152, the form of link 170 may take any form known in the art of networking. In some embodiments, information from the database or storage entity 115 may be accessed by computing device 122 via link 170 and the network 168.

In some embodiments, the computing device 122 may control more than one more than one voltage source 110, more than one current measuring device 112, and/or more than one light source 113. In some embodiments, the computing device 122 may service more than one nanotip sensor 200, so that the computing device 122 may control sample testing at each of the more than one sensors 200, and may collect and process testing data that is produced at each of the more than one sensors 200.

Turning back to FIG. 1, by using the system 100, samples may be able to be measured nearly as rapidly as they can be collected. Indeed, the sensing system 100 may have a very rapid response time as compared with currently known techniques (e.g., on the order of a few tens of seconds to a few seconds) with the limiting time constant being that of the physical sampling (e.g., adsorption to the sensor nanotips). Furthermore, the specificity of the sensing or detection may also increase over currently known techniques.

Moreover, after the sensor 102 has been used to analyze a sample, the sensor 102 may easily be cleaned of the adsorbed particulates. For example, the incoming sample flow may be stopped, and the bias or the voltage applied to the nanotips by the voltage source 110 may be increased to an ionizing voltage that may cause plasma to be struck and any adsorbed particulates to be ionized and desorbed from the cathode or tip. The desorbed particulates may be extracted from the sensing chamber 105 by a vacuum system 120 or by some other flushing mechanism. In some embodiments, the system 100 may include an inert gas source 124 in fluid connection with the chamber 105. A desired amount of the inert gas (e.g., argon, neon, or the like) may be released into the chamber 105 prior to increasing the voltage to the ionizing voltage to physically bombard the nanotips for cleaning. As such, a single sensor 102 may be easily cleaned and re-used numerous times.

Additional details of the various portions of the sensing or detection system 100 are discussed below in conjunction with FIG. 1.

Nanotip Architecture

Figure 3A:
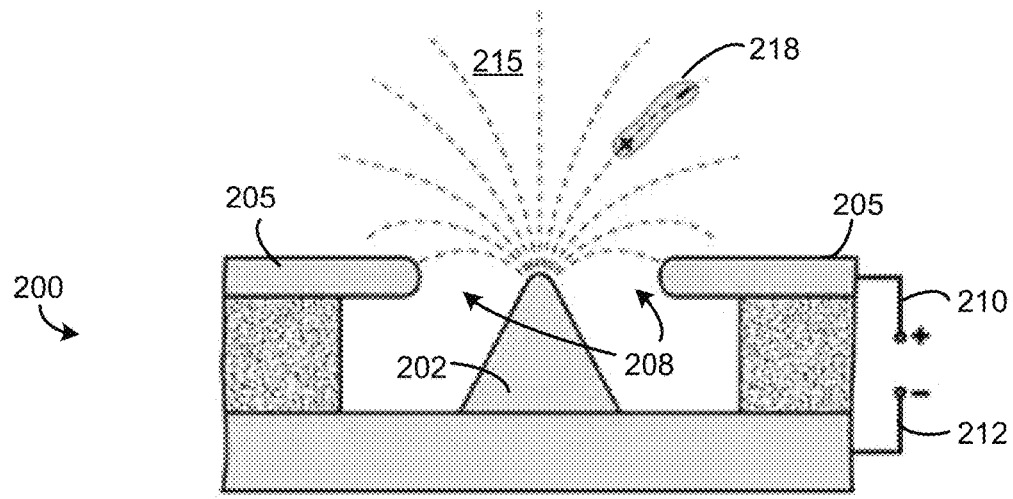
FIG. 3A is a block diagram of an embodiment of a nanotip that may included on the sensor of FIG. 1.

FIG. 3A is an architectural side perspective of one of the plurality of nanotips that may be included on the sensor 102 of FIG. 1. The nanotip sensor 200 may include a cathode 202 that may serve as an electrostatic precipitator, and an anode 205 that may serve as a second electrical contact. In the embodiments illustrated in FIG. 3A, the cathode 202 and the anode 205 are shown in a tip and ring configuration, where the anode 205 surrounds the cathode 202, thus creating a gap 208 between the anode 205 and the tip of the cathode 202. The gap 208 may have a substantially annular shape. Other configurations of the cathode 202, the anode 205, and the gap 208, though, may be possible, and may be used in the sensor 102. For example, the positions of the cathode and anode may be reversed from that shown in FIG. 3A, so the anode configured as the tip and the cathode is configured as the ring. In another example, the cathode and/or the anode may be shaped differently. In yet another example, a cathode and anode may be configured as two parallel rectangular co-planar bars or strips separated by a rectangular gap. These examples and/or other shapes and configurations of the cathode 202 and anode 205 of a nanotip sensor 200 may be used in the sensor 102.

The nanotip sensor 200 may include electrical connections or contacts 210 and 212. The contacts 210 and 212 may be electrically connected to the voltage source 110 and to the current measuring device 112 of FIG. 1. When a low-level voltage is applied to the cathode 202 and the anode 205 using the contacts 210 and 212, a low-level bias may be created that may generate an electric field 215, as denoted by the dashed lines. The electric field 215 may cause a particulate 218 to orient based on a polarizability of the particulate 218, e.g., based on a charge displacement of the particulate 218. As commonly known, all particulates 218 of a same type of molecule or cell may exhibit substantially identical polarizabilities. Accordingly, particulates 218 of a same type may self-assemble as adsorbates onto one or more nanotips with identical orientations.

Figure 3B:
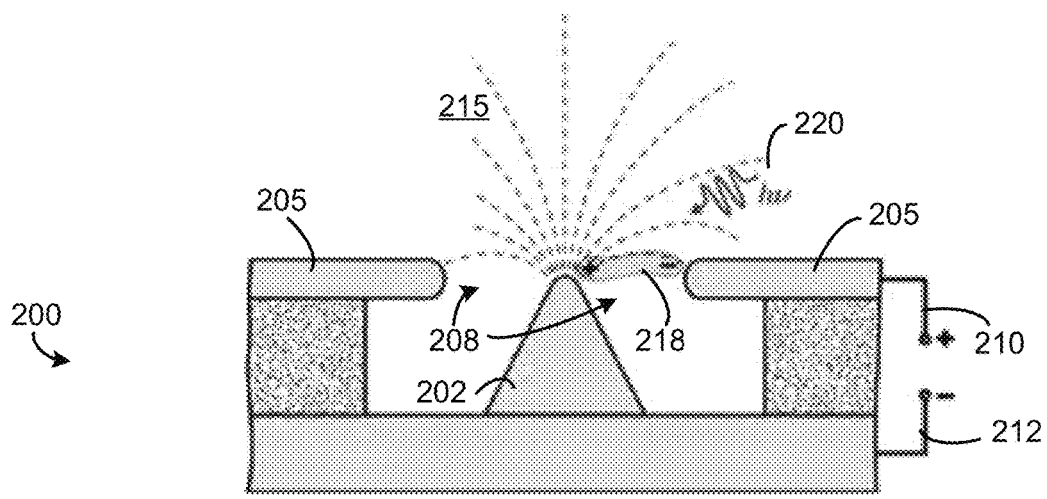
FIG. 3B is the block diagram of the nanotip of FIG. 3A with an adsorbed particulate bridging the gap of the nanotip.

FIG. 3B illustrates the nanotip sensor 200 of FIG. 3A with the particulate 218 adsorbed to the tip of the cathode 202. As the adsorbed particulate 218 is polarized, the end of the particulate opposite to the adsorbed end may be attracted to the anode 205, thus causing the adsorbed particulate 218 to span or bridge the gap 208 between the cathode 202 and the anode 205. An electrical circuit may include the cathode 202, the spanning or bridging particulate 218, the anode 205, and a voltage source that is electrically connected to the nanotip via contacts 210 and 212 (e.g., the variable voltage source 110) may be formed.

Figure 3C:
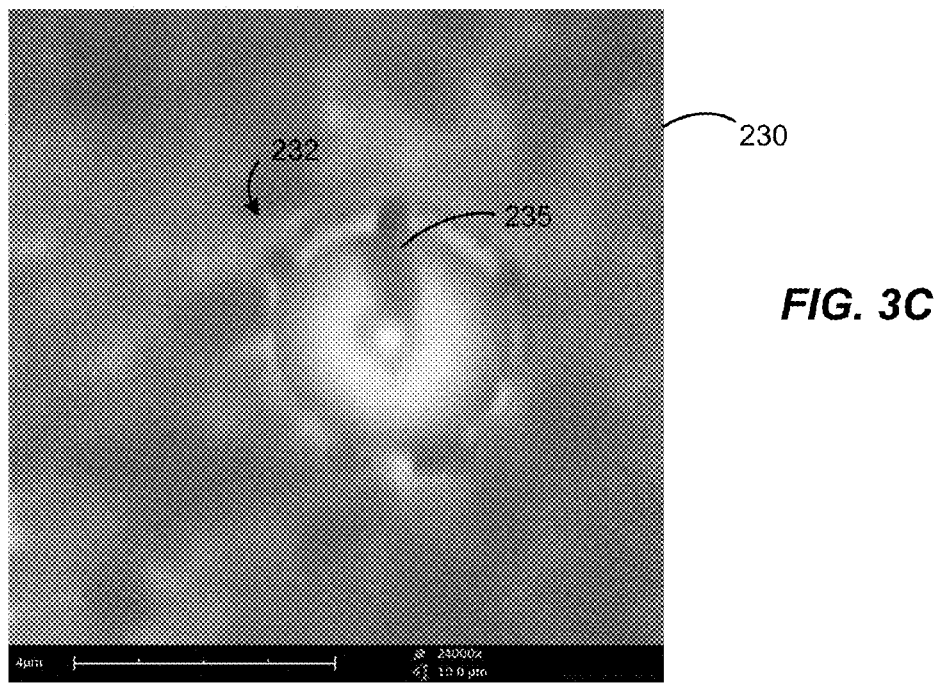
FIG. 3C is a reproduction of a scanning electron microscopy image ("SEM image") of a physical, prototyped nanotip being spanned by a single *E. coli* bacterium.

For some particulates, a single particulate (e.g., a single molecule, a single cell, a single virus, etc.) may be sufficient to bridge or span the gap between the cathode 202 and the anode 205 to form the electrical circuit. For example, *Escherichia coli* (commonly abbreviated *E. coli*), is a Gram negative rod-shaped bacterium that is commonly found in the lower intestine of warm-blooded organisms (endotherms). A physical size or length of a single *E. coli* bacteria typically varies from 1 to 3 μm, and may easily span a 2 μm gap 208 of a nanotip sensor 200 with a single cell. For example, FIG. 3C is a reproduction of a scanning electron microscopy image ("SEM image") 230 of a physical, prototyped nanotip 232 that has a diameter of approximately 4.23 μm and is being spanned by a single *E. coli* bacterium 235.

Figure 3D:
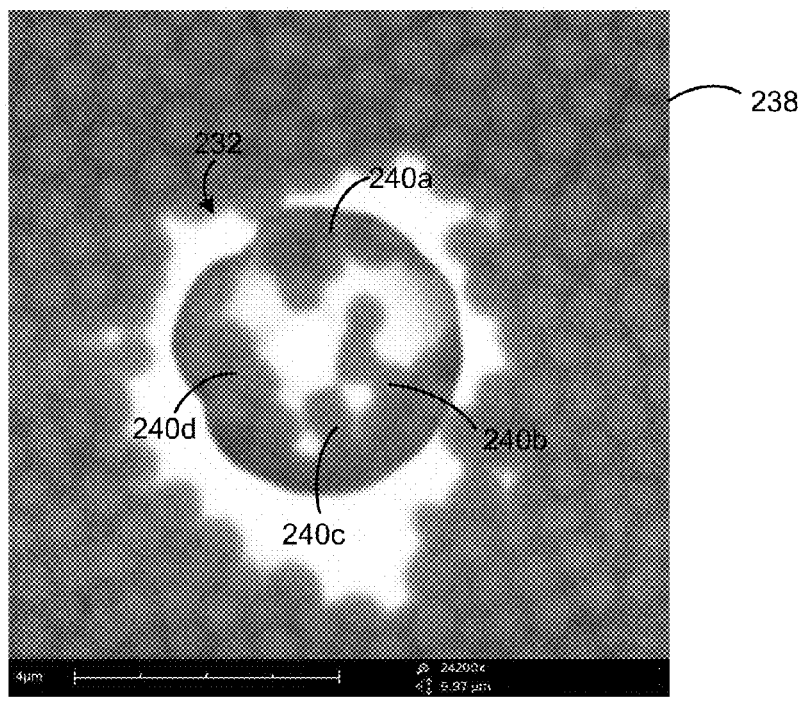
FIG. 3D is a reproduction of an SEM image of the physical, prototyped nanotip being spanned by a cluster of *S. aureus* bacteria.

Some species, however, exist in groups of cells. For example, diplococci bacteria (e.g., *Streptococcus penumonia, Moraxella catarrhalis, Neisseria gonorrhea, Neisseris meningitides*) are arranged in two-cell pairs, while bacteria in the Streptococci genus are arranged in chains. Bacteria in the *Sarcina* genus have a cuboidal cell arrangement. *Staphylococcus* is a genus of bacteria that contains cells arranged in large clusters of cocci. Similarly, bacilli shaped bacteria can form chains. For these and other grouping species, more than one particulate of a same species or type may group together to bridge or span the gap 208 between the cathode 202 and the anode 205. The grouping may include a two-cell pair, a cuboidal arrangement, a cluster, a chain, or any other form of grouping that is inherent to the species. For example, *Staphylococcus aureus* (commonly abbreviated *S. aureus*) typically has a length of less than 1 μm for each cell, but generally exists in clusters. Thus, while a single cell of *S. aureus* is not large enough to bridge a nanotip gap 208 to form an electrical circuit, a cluster of 5-20 *Staphylococcus aureus* bacteria may be able to span the 2 μm gap 208 of the nanotip sensor 200 to create the electrical circuit. For example, FIG. 3D is a reproduction of an SEM image 238 of the physical, prototyped nanotip 232 shown in FIG. 3C with its gap being spanned by clusters of *S. aureus* bacteria 240a, 240b, 240c and 240d.

After the particulate 218 has adsorbed to the nanotip, has spanned or bridged the gap 208 between the cathode 202 and the anode 205 (whether individually or via grouping), and has formed the electrical circuit, the connected voltage source 110 may generate a range or plurality of voltages, and a current response or "profile" of the electrical circuit may be determined and recorded. In an embodiment, the profile of the electrical circuit may be based on a current vs. voltage (I-V) characteristic of the electrical circuit. In one particular non-limiting example, the I-V characteristic may correspond to an I-V curve in the following manner. The current flowing through the electrical circuit for each of the plurality of voltages may be measured by a current measuring device that is electrically connected to the nanotip via the contacts 210 and 212 (e.g., the current measuring device 112), and a current vs. voltage (I-V) curve may be determined based on the measured currents. A conductive spectrum of the sample may be determined by taking a derivative of the I-V curve corresponding to the adsorbed particulate 218 over the range or plurality of voltages. The conductive spectrum of the particulate 218 may statistically differ from conductive spectrums of other particulates. Thus, by analyzing the conductive spectrum of the sample and comparing the conductive spectrum of the sample to conductive spectrums of known particulates, the adsorbed particulate 218 may be positively detected or identified. Accordingly, in this example, the profile of the particulate may correspond to its conductive spectrum.

Augmenting the Specificity of a Sensor

Several embodiments may augment the specificity of particulate detection or identification by the sensor 102. One or more of the embodiments for augmenting the specificity of the sensor 102 may be used in conjunction with the system 100, the sensor 102, and/or its nanotip sensors 200.

In some embodiments of augmenting the specificity of the sensor 102, a profile of a particulate may correspond to its conductive-photonic spectrum instead of to its conductive spectrum. In these embodiments, a range or plurality of wavelengths of light (e.g., from far-IR to far-UV) may be applied to the sensor 102 and its plurality of nanotips (e.g., to the nanotip sensor 200) while the range or plurality of voltages is applied. For example, while the variable voltage source 110 sweeps through the desired voltage range, the variable wavelength light source 113 may generate a range or plurality of photonic wavelengths, such as denoted by hu (reference 220) in FIG. 3B. The wavelengths may irradiate the sensor 102, its nanotips, and any particulates that are adsorbed to its nanotips. In these embodiments, the conductive-photonic current response or spectrum of the sample may be determined by taking a derivative of the I-V curve over the range or plurality of voltages and over the range or plurality of photonic wavelengths 220. The conductive-photonic spectrum of the particulate 218 may statistically differ from conductive-photonic spectrums of other particulates. Thus, by analyzing the conductive-photonic spectrum of the sample and comparing the conductive-photonic spectrum of the sample to conductive-photonic spectrums of known particulates, the adsorbed particulate 218 may be positively detected and/or identified. As conductive-photonic spectrum profiles are based on two input parameters (e.g., voltage level/magnitude and photonic wavelength) instead of only one input parameter (e.g., voltage level/magnitude), the specificity of particulate detection or identification by the sensor 102 may be increased.

Figure 4:
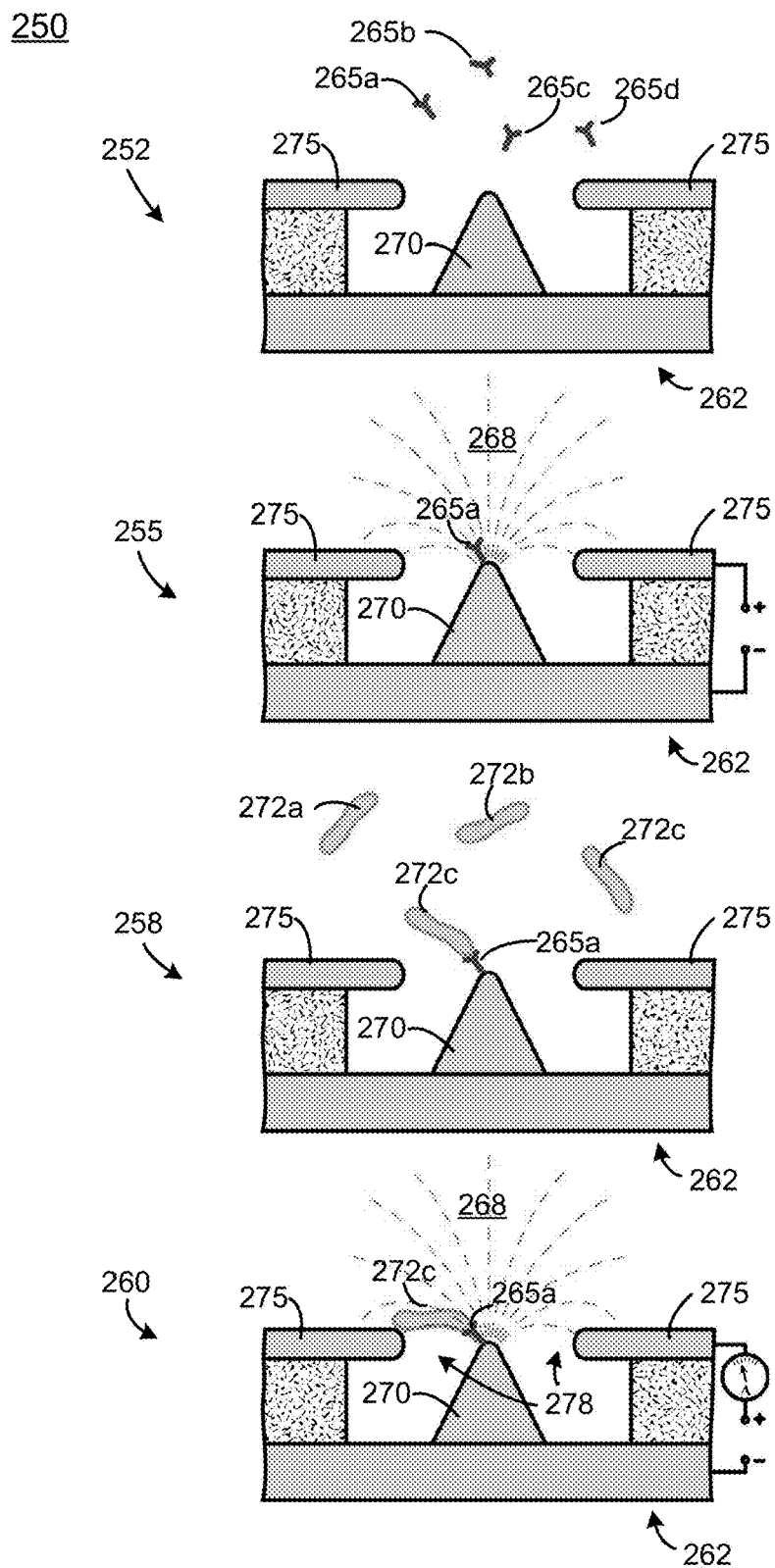
FIG. 4 depicts an embodiment of several stages of priming a nanotip.

In some embodiments, the specificity of particulate identification or detection may be increased by priming the nanotips of the sensor 102 before the sensor 102 is exposed to the sample. For example, the nanotips of the sensor 102 may be primed with a primer corresponding to a target particulate that is suspected to be present in the sample or that is otherwise desired to be detected. FIG. 4 illustrates an embodiment 250 of several stages 252, 255, 258, 260 of priming nanotip using antibodies or antibody fragments. Of course, priming nanotips is not limited to only the stages 252, 255, 258, 260. Some embodiments of priming nanotips may use fewer stages than are shown in FIG. 4, and some embodiments may use more stages than are shown in FIG. 4. For clarity purposes, instead of depicting an entire sensor with a plurality of nanotips, FIG. 4 illustrates only a single nanotip 262 of a sensor being primed by antibodies, although the stages 252, 255, 258, 260 are equally applicable to any or all of a multiplicity of nanotips on the sensor 102.

As used herein, the term "antibody" is used in the broadest sense and includes fully assembled antibodies, monoclonal antibodies, polyclonal antibodies, multispecific antibodies (including bispecific antibodies), antibody fragments that can bind an antigen (including, Fab', F'(ab)$_2$, Fv, single chain antibodies, diabodies), and recombinant peptides comprising the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated.

As used herein, the term "antibody fragments" comprises a portion of an intact immunoglobulin, preferably an antigen binding or variable region of the intact antibody, and may include multispecific (bispecific, trispecific, etc.) antibodies formed from antibody fragments. Fragments of immunoglobulins may be produced by recombinant DNA techniques or by enzymatic or chemical cleavage of intact antibodies.

Non-limiting examples of antibody fragments include Fab, Fab', F(ab')$_2$, Fv (variable region), domain antibodies (dAb, containing a VH domain) (Ward et al., Nature 341: 544-546, 1989), complementarity determining region (CDR) fragments, single-chain antibodies (scFv, containing VH and VL domains on a single polypeptide chain) (Bird et al., Science 242:423-426, 1988, and Huston et al., Proc. Natl. Acad. Sci. USA 85:5879-5883, 1988, optionally including a polypeptide linker; and optionally multispecific, Gruber et al., J. Immunol. 152: 5368 (1994)), single chain antibody fragments, diabodies (VH and VL domains on a single polypeptide chain that pair with complementary VL and VH domains of another chain) (EP 404,097; WO 93/11161; and Hollinger et al., Proc. Natl. Acad. Sci. USA, 90:6444-6448 (1993)), triabodies, tetrabodies, minibodies (scFv fused to CH3 via a peptide linker (hingeless) or via an IgG hinge) (Olafsen, et al., Protein Eng Des Sel. 2004 April; 17(4):315-23), linear antibodies (tandem Fd segments (VH-CH1-VH-CH1) (Zapata et al., Protein Eng., 8(10):1057-1062 (1995)); chelating recombinant antibodies (crAb, which can bind to two adjacent epitopes on the same antigen) (Neri et al., J Mol Biol. 246:367-73, 1995), bibodies (bispecific Fab-scFv) or tribodies (trispecific Fab-(scFv)(2)) (Schoonjans et al., J Immunol. 165:7050-57, 2000; Willems et al., J Chromatogr B Analyt Technol Biomed Life Sci. 786:161-76, 2003), intrabodies (Biocca, et al., EMBO J. 9:101-108, 1990; Colby et al., Proc Natl Acad Sci USA. 101:17616-21, 2004) which may also comprise cell signal sequences which retain or direct the antibody intracellularly (Mhashilkar et al, EMBO J 14:1542-51, 1995; Wheeler et al., FASEB J. 17:1733-5, 2003), transbodies (cell-permeable antibodies containing a protein transduction domain (PTD) fused to scFv (Heng et al., Med Hypotheses. 64:1105-8, 2005), nanobodies (approximately 15 kDa variable domain of the heavy chain) (Cortez-Retamozo et al., Cancer Research 64:2853-57, 2004), small modular immunopharmaceuticals (SMIPs) (WO03/041600, U.S. Patent publication 20030133939 and US Patent Publication 20030118592), an antigen-binding-domain immunoglobulin fusion protein, a camelized antibody (in which VH recombines with a constant region that contains hinge, CH1, CH2 and CH3 domains) (Desmyter et al., J. Biol. Chem. 276: 26285-90, 2001; Ewert et al., Biochemistry 41:3628-36, 2002; U.S. Patent Publication Nos. 20050136049 and 20050037421), a VHH containing antibody, heavy chain antibodies (HCAbs, homodimers of two heavy chains having the structure H2L2), or variants or derivatives thereof, and polypeptides that contain at least a portion of an immunoglobulin that is sufficient to confer specific antigen binding to the polypeptide, such as a CDR sequence, as long as the antibody retains the desired biological activity.

The term "epitope," as used herein, refers generally to a particular region of the particulate or target molecule. An epitope may consist of a small peptide derived from a larger polypeptide. An epitope may also be a two or three-dimensional surface or surface feature of a polypeptide, protein or macromolecular complex that comprises several non-contiguous peptide stretches or amino acid groups.

Interactions between antigen and antibody involve non-covalent binding of an antigenic determinant (epitope) to the variable region (complementarity determining region, CDR) of both the heavy and light immunoglobulin chains.

Turning back to FIG. 4, in a first stage 252 one or more corresponding antibodies or antibody fragments 265a-265d may be introduced into the chamber 105 that houses the sensor 102. In a subsequent stage 255, an application of a bias (e.g., by using the voltage source 110) may generate an electric field 268 that may polarize the antibodies or antibody fragments 265 and may cause one or more antibodies or antibody fragments 265a to be adsorbed to the cathode 270 of the nanotip 262, thus priming the nanotip 262.

After the nanotip 262 has been primed, the electric field 268 may be turned off, and the sample may be released into the chamber 105. Stage 258 illustrates that only particulates 272a-272d that match the adsorbed antibodies or antibody fragments 265 may be precipitated onto the cathodes 268 of the nanotip 262. In particular, an antigen of a particulate 272c may bind or otherwise physically connect to an adsorbed antibody or antibody fragment 265a, and thus may be attached to the adsorbed antibody or antibody fragment. Accordingly, the particulate 272c may be precipitated to the cathode 270 in conjunction with the respective antibody or antibody fragment 265a. After precipitation of at least some of the target particulates 272a-272d, a bias or electric field 268 may then be re-applied as shown by the stage 260. The precipitated particulate(s) (e.g., particulate 272c) may be attracted to the anode 275 of the nanotip 262, and may bridge the gap 278 of the nanotip 262 to form electrical circuits.

Upon formation of the electrical circuits, the applied voltage and (optionally) light wavelengths may be varied across respective ranges, and the sensor's response may be measured in a manner similar as to previously discussed. Accordingly, priming nanotips with antibodies or antibody fragments corresponding to a target particulate may lower the probability of a false positive to virtually zero, as only corresponding particulates are precipitated to the nanotips.

While FIG. 4 illustrates an embodiment 250 of several stages 252, 255, 258, 260 of priming nanotip using antibodies or antibody fragments, the stages 252, 255, 258, 260 are equally applicable to embodiments where nucleic acids are used for nanotip priming. In some embodiments, the nucleic acid may be a DNA (Deoxyribonucleic acid) or RNA (Ribonucleic acid) fragment of sufficient length that allows for the DNA or RNA to detect the presence of a target particulate DNA/RNA sequence that is complementary to the DNA or RNA fragment. In some embodiments, the DNA or RNA fragment comprises at least 50-1,000 nucleotides, such as about 50, about 60, about 70, about 80, about 90, about 100, about 110, about 120, about 130, about 150, about 160, about 170, about 180, about 190, about 200, about 250, about 300, about 350, about 400, about 500, about 550, about 600, about 650, about 700, about 800, about 900 or about 1,000 nucleotides in length. The DNA/RNA fragment hybridizes to single-stranded nucleic acid (DNA or RNA) whose base sequence allows probe-target base pairing due to complementarity between the fragment and target particulate DNA/RNA sequence. Hybridization is the process of establishing a non-covalent, sequence-specific interaction between two or more complementary strands of nucleic acids into a single hybrid, which in the case of two strands is referred to as a duplex. Oligonucleotides, DNA, or RNA will bind to their complement under normal conditions, so two perfectly complementary strands will bind or attach to each other readily. In order to reduce the diversity and obtain the most energetically preferred hybrids, a technique called annealing is used in laboratory practice. However, due to the different molecular geometries of the nucleotides, a single inconsistency between the two strands will make binding between them less energetically favorable. Measuring the effects of base incompatibility by quantifying the rate at which two strands anneal can provide information as to the similarity in base sequence between the two strands being annealed. The hybrids may be dissociated by thermal denaturation, also referred to as melting. Here, the solution of hybrids is heated to break the hydrogen bonds between nucleic bases, after which the two strands separate. In the absence of external negative factors, the processes of hybridization and melting may be repeated in succession indefinitely, which lays the ground for polymerase chain reaction. Most commonly, the pairs of nucleic bases A=T and G≡C are formed, of which the latter is more stable. With respect to nanotip priming, a target particulate may be precipitated to the cathode in conjunction with a bound, attached or otherwise physically connected respective nucleic acid fragment. After the target particulates are precipitated, a bias or electric field may then be re-applied, and the precipitated particulates may be attracted to the anode 275 of the nanotip 262, thus bridging the gap 278 of the nanotip 262 to form electrical circuits.

In yet another embodiment of augmenting the specificity of detection or identification by the sensor 102, a filter 118 may be incorporated between the sample source 108 and the chamber 105, as shown in FIG. 1. Typically, but not necessarily, particulates may be carried on particles such as pollen, molds, dust, yeast, etc., or on a liquid droplet such as water, oil, bodily fluids, etc. The filter 118 may be configured to separate particulates from their carriers, and to physically prevent particles and matter larger than a desired physical size from entering the chamber. Use of the filter 118 may result in an increase in the concentration of target particulates in the chamber, and thus may increase the probability of the target particulates being adsorbed to the nanotips on the sensor 102. Typically, but not necessarily, embodiments that include the filter 118 may also include the vacuum system 120.

Figure 5A:
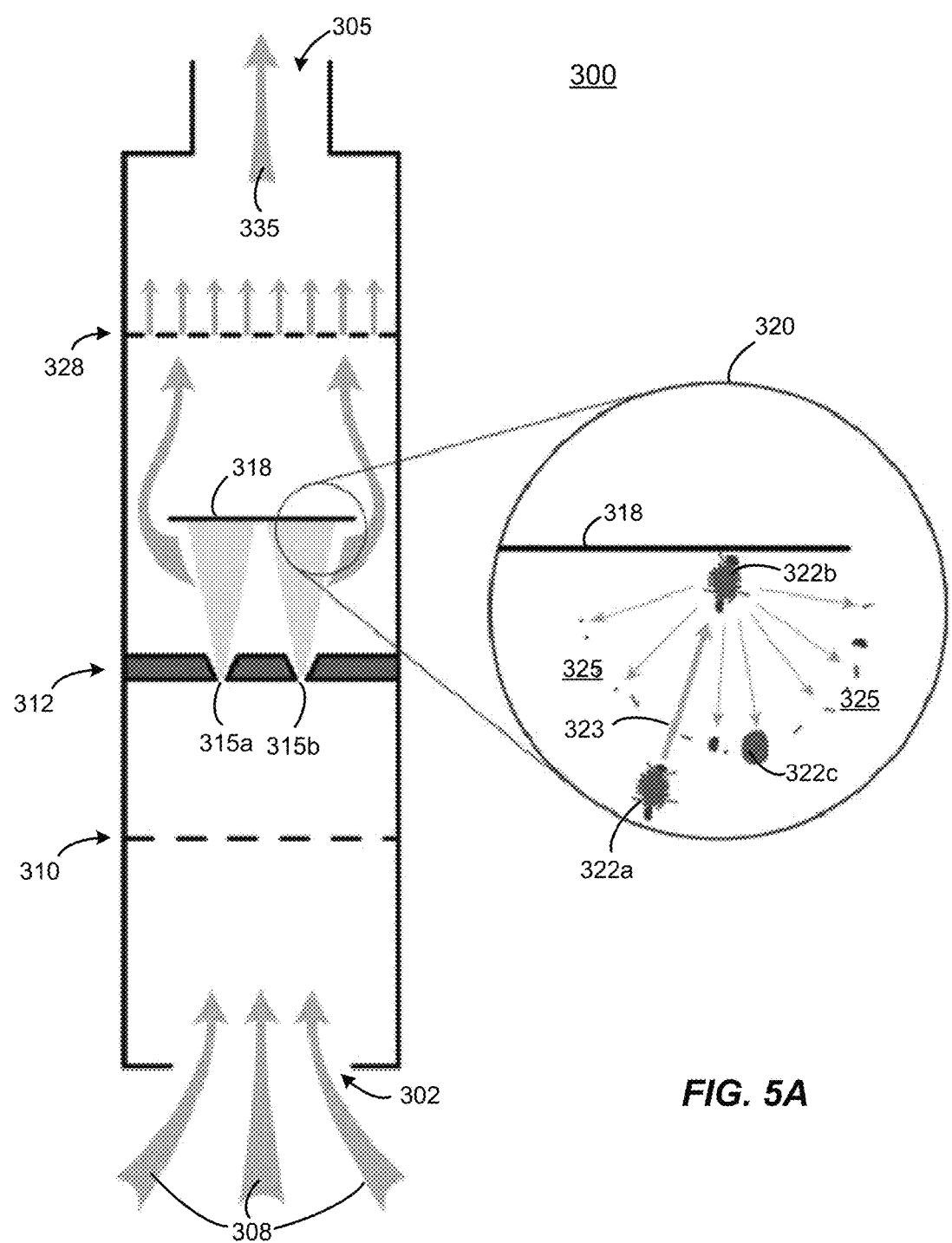
FIG. 5A is a block diagram of an embodiment of a filter that may be used in the system of FIG. 1 with an expanded view of a selected portion.
Figure 5B:
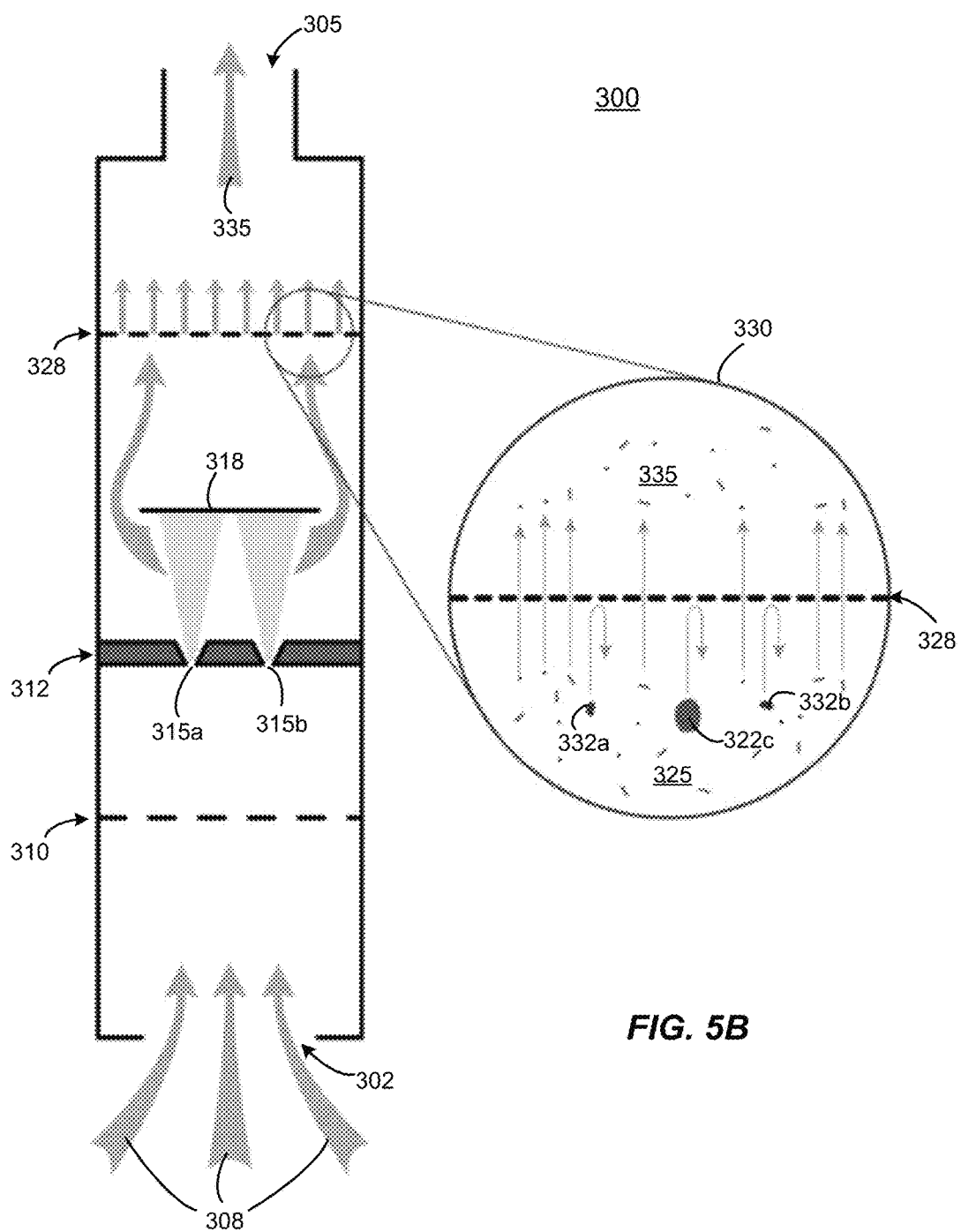
FIG. 5B is a block diagram of the filter shown in FIG. 5A with an expanded view of another selected portion.
Figure 6:
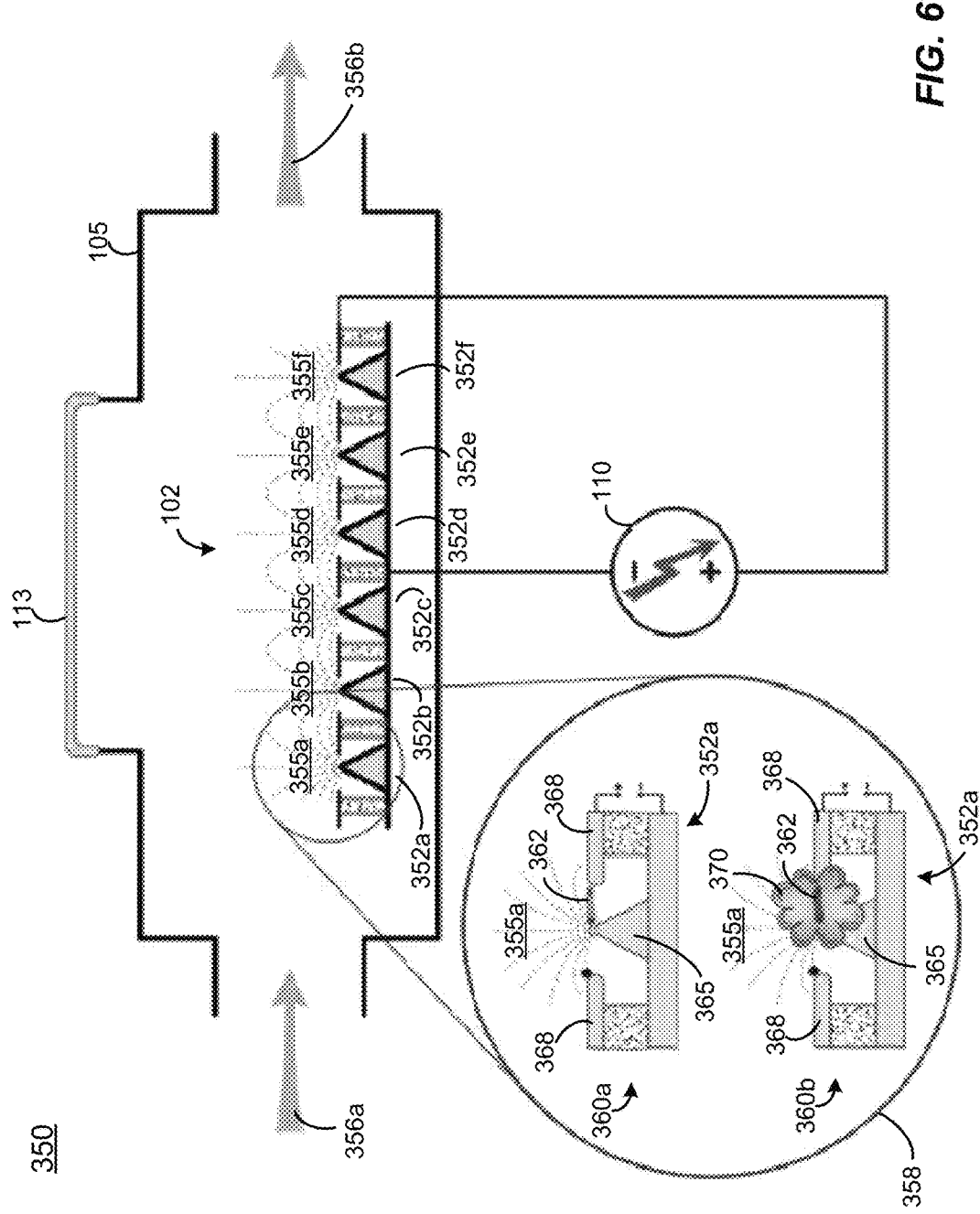
FIG. 6 depicts an embodiment of cleaning the sensor of FIG. 1.

FIGS. 5A and 5B illustrate an embodiment 300 of the filter 118 of FIG. 1. For clarity, FIGS. 5A and 5B are discussed in conjunction with FIG. 1. In FIG. 5A, the filter 300 may be in fluid communication with the sample source 108 via an entry port 302, and may be in fluid communication with the chamber 105 via an exit port 305. The sample flow or stream 308 may enter the filter 300 via the entry port 302. In an embodiment, by activating the vacuum system 120, the sample 308 may be drawn into and through the filter 300. One or more initial levels of filtration 310 may physically prevent larger particulates and particles that are undesired from entering the chamber 105.

A secondary level of filtration 312 may include one or more "pin hole" sized apertures 315a, 315b that are each smaller than the apertures of the initial filter 310. A deflector plate 318 may be situated directly behind the secondary filter 312. Particulates in the sample that pass through the pinholes 315a, 315b may impact the deflector plate 318. The secondary pinhole filter 312 and the deflector plate 318 may further filter incoming particulates by physical size, and may physically separate the target particulates from their respective carriers, as shown in the magnified view 320. The magnified view 320 illustrates a carrier 322*a-c* at different instances in time 322*a*-322*c*. Initially, the carrier 322*a*, with attached particulates, may approach the deflector plate 318 (as denoted by the incoming arrow 323), and may impact the deflector plate 318, as shown by 322*b*. After impact, as denoted by the outgoing arrows, the carrier 322*c* may be separated from its previously-attached particulates 325.

The disassociated carrier 322*c* and the disassociated particulates 325 may be drawn, e.g., by the activated vacuum system 120, towards a tertiary level of filtration 328. The tertiary level of filtration 328 may include one or more filters having apertures that are smaller than both the initial 310 and the secondary 312 levels of filtration. In FIG. 5B, a magnified view 330 illustrates the carrier 322*c* and the disassociated particulates 325 being drawn towards the tertiary level of filtration 328. As shown in the magnified view 330, the carrier 322*c* and some disassociated particulates 332*a*, 332*b* may be too large to pass through the filter 328, whereas some portion 335 of the disassociated particulates may be small enough to pass through the filter 328. Of course, the apertures of the tertiary level of filtration 328 may be sized to be large enough for potential target particulates to pass through. After the sample stream is filtered through the tertiary level of filtration 328, the remaining particulates 335 may flow through the exit port 305 and into the chamber 105 to surround the sensor 102. Thus, as shown in FIGS. 5A and 5B, the filter 300 may be a physical filter that filters an initial sample stream 308 into a filtered stream 335 that includes potential target particulates and smaller particulates or fragments thereof.

Cleaning the Sensor

FIG. 6 illustrates an embodiment of cleaning the sensor 102. FIG. 6 includes a more detailed, architectural side view 350 of the chamber 105 surrounding the sensor 102 of FIG. 1. The sensor 102 may include a plurality of nanotips 352*a*-352*f*, each with a corresponding electric field 355*a*-355*f* that is generated from an applied voltage produced by the voltage source 110. For reference, the voltage source 110 and the light source 113 of FIG. 1 are both shown in FIG. 6. A sample stream or flow through the chamber 105 is denoted by the arrows 356*a* and 356*b*.

FIG. 6 includes a magnified view 358 of the nanotip 352*a* at two instances in time 360*a*, 360*b*. The first instance 360*a* illustrates an instance in time during which an electrical circuit is formed by a particulate 362, the voltage source 110, and the cathode 365 and anode 368 of the nanotip 352*a*. During the first instance in time 360*a*, a current response of the electrical circuit may be collected, in a manner such as previously discussed.

The second instance 360*b* illustrates a later instance in time during which the nanotip 352*a* is being cleaned. During the second instance 360*b*, the voltage level applied to the electrical circuit may be increased (e.g., by the voltage source 110) to an ionizing voltage level or magnitude at which the adsorbed particulate 362 (and, indeed, any other adsorbed particulates on other nanotips 352*b*-352*f*) may be ionized 370. The ionized particulates may desorb from the nanotip 352*a* and from other nanotips 352*b*-352*f*, and may re-enter the sample stream 356*b* to be pumped, vacuumed, or otherwise removed or evacuated from the chamber 105. In this manner, the sensor 102 and its nanotips may be cleaned of precipitates and adsorbates, and furthermore, any desorbed precipitates that are evacuated from the chamber 105 may be of a non-hazardous, benign condition. In some embodiments, prior to increasing the voltage to an ionizing level, a desired amount of inert gas (e.g., argon, neon, or the like) may be released into the chamber 105 to physically bombard the nanotips for additional cleaning.

The cleaning technique of the sensor 102 allows the sensor 102 to be safely re-used multiple times without producing any hazardous waste. Indeed, under laboratory conditions, a prototype fabricated sensor was cleaned and re-used over 100 times.

Physical Nanotips and Arrays of Nanotips

Figure 7A:
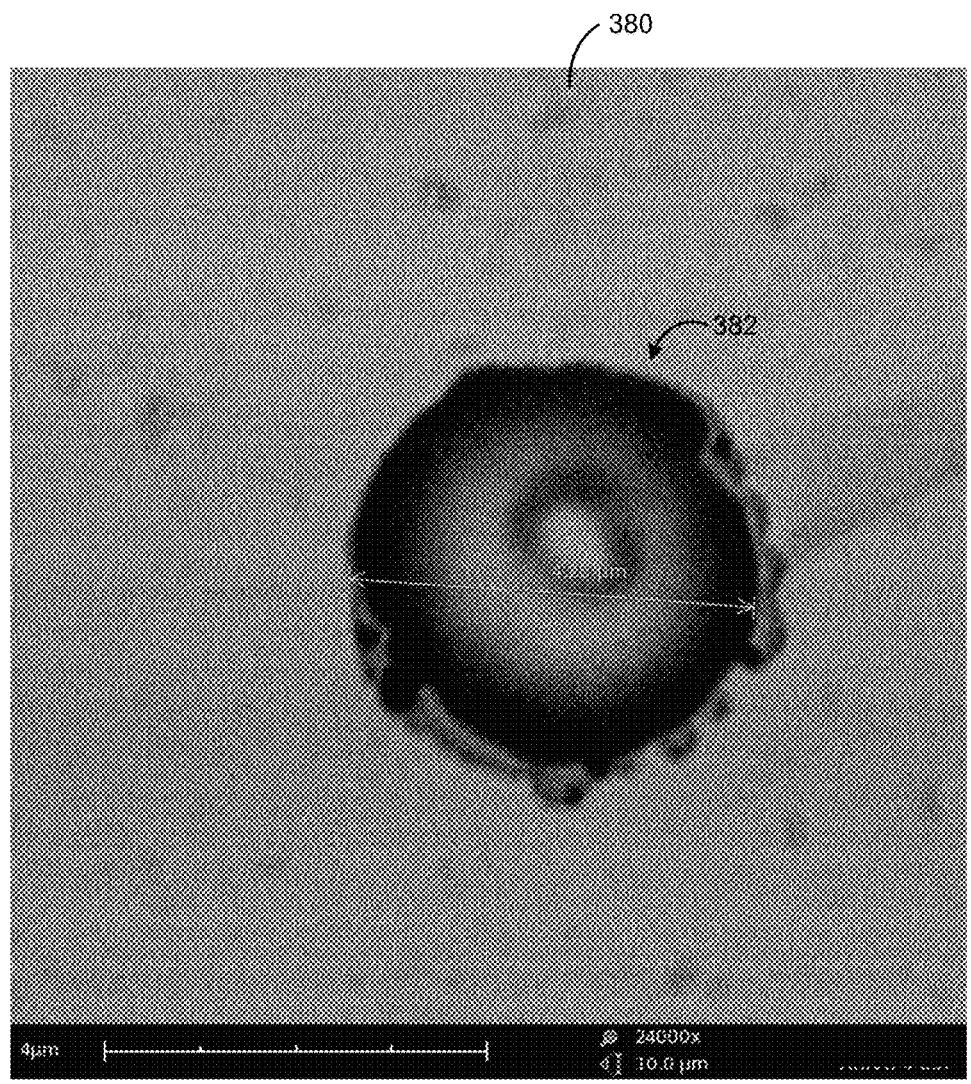
FIG. 7A is a reproduced scanning electron microscopy image of a fabricated nanotip.
Figure 7B:
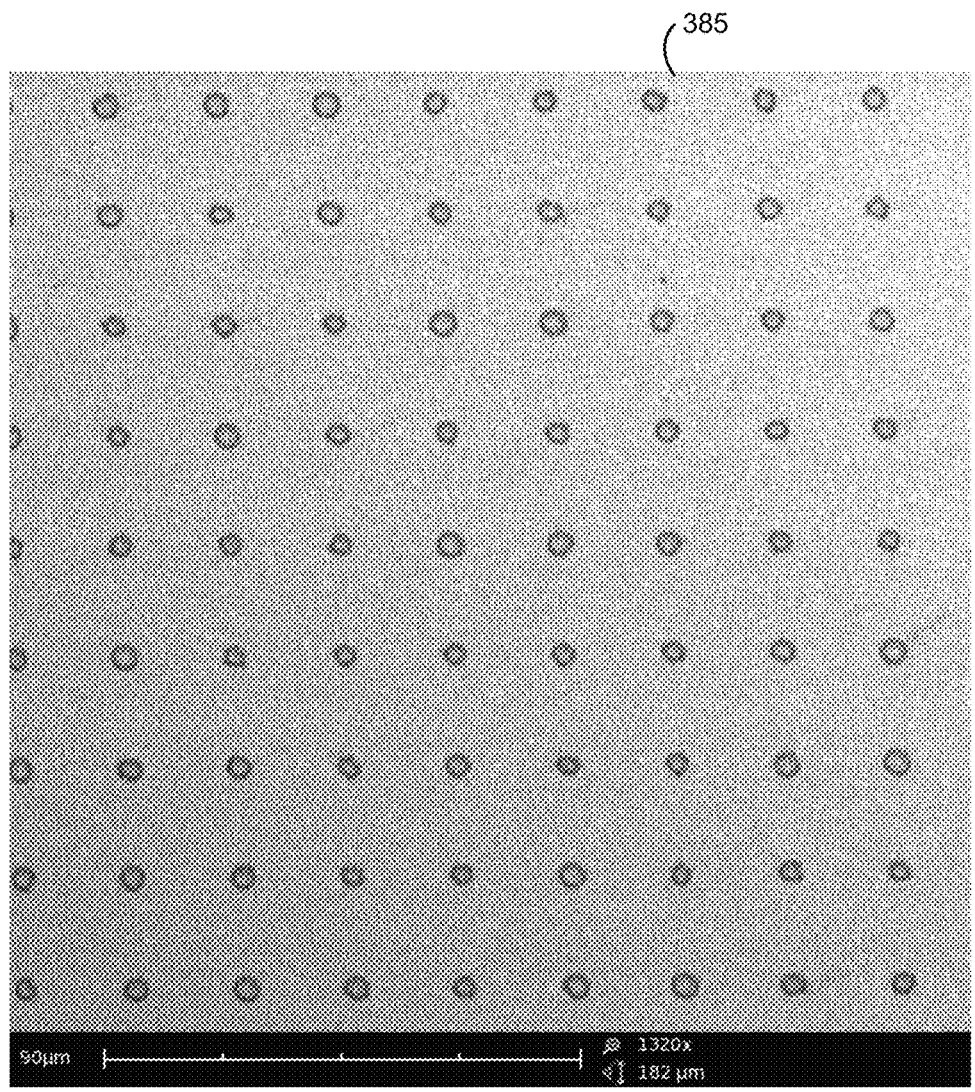
FIG. 7B is a reproduced scanning electron microscopy image of an area of a fabricated sensor.

FIG. 7A is a reproduction of a scanning electron microscopy image ("SEM image") 380 of a prototype fabricated embodiment 382 of the nanotip sensor 200 of FIG. 1. In this embodiment, the diameter of the physical nanotip 382 is about 4.23 μm, and the magnification of the image 380 is 24,000×. The fabricated nanotip 382 is one of a plurality of fabricated nanotips of a physical, fabricated embodiment of the sensor 102, a portion of which is shown in a reproduction of an SEM image 385 in FIG. 7B. In FIG. 7B, the sensor is a nanofabricated chip including 250,000 individual nanotips arranged in an array, with a length of each side of the chip measuring between 0.5 to 1.0 cm. The magnification of the image 385 is 1320×.

As the sensor 102 may include a multiplicity of nanotips, each of which may attract one or more of a multiplicity adsorbed particulates, the resulting multiplicity of formed electrical circuits may provide a multiplicity of parallel conduction paths within the sensor 102. Accordingly, for a given type or species of particulate, the response generated by the multiplicity of nanotips to the range or plurality of voltages may be amplified over a response generated by a single nanotip, and thus, the signal-to-noise ratio of the array for the given particulate may be significantly increased over that of a single nanotip. For example, if a probability of a single given particulate being adsorbed to a single nanotip is X % and the array includes $10^6$ nanotips, then a signal generated by the array (e.g., measured current) may be $X*10^4$ times greater than a signal generated by a single nanotip with unity probability. Accordingly, exposing the plurality of nanotips to a sample may result in a statistically complete loading of the multiplicity of nanotips with adsorbed disassociated particles that produces, in turn, a strong signal-to-noise ratio.

Of course, FIG. 7B shows only one of many possible embodiments of nanotip arrangement on a sensor 102. Other embodiments are possible. For example, the plurality of nanotips need not be limited to being arranged in an array. Other arrangements, such as concentric circles, rows that are alternately shifted, or even a random configuration may be contemplated with embodiments of the present disclosure. For clarity of discussion herein, however, the present disclosure uses the term "array" to refer to the arrangement of nanotips on a sensor, although it is understood that any techniques or principles using an array may be easily applied to other arrangements of nanotips on a sensor 102.

A sensor 102 may be fabricated with any technique utilized in the semiconductor industry, and in particular, may be manufactured using nanofabrication in order to size the gaps of the nanotips to correspond to a range of potential particulate physical size(s). In some embodiments, each of the nanotips may have a substantially uniform configuration. The term "substantially uniform," as used herein, refers to being as uniform as possible within the limits of manufacturing. For example, with a tip and ring nanotip configuration, each tip of each nanotip on an array may have a same height, diameter and shape as any other tip, and each gap of each nanotip may have a same width, so far as is possible within manufacturing or fabrication limitations and/or tolerances.

In some embodiments, rather than all nanotips of an array being substantially uniform, one or more of the plurality of nanotips on a sensor 102 may be configured differently from other nanotips. For example, a first subset of the plurality of nanotips may have gaps each sized corresponding to a first type of particulate, and a second subset of the plurality of nanotips may have gaps that are each sized corresponding to a second type of particulate. As such, each of the nanotips in the first subset may be substantially uniform, and each of the nanotips in the second subset may be substantially uniform but with a different gap size than nanotips in the first subset. In this example, portions of a same array of nanotips may be configured differently to effect the bridging and detection of differently sized particulates.

Figure 8:
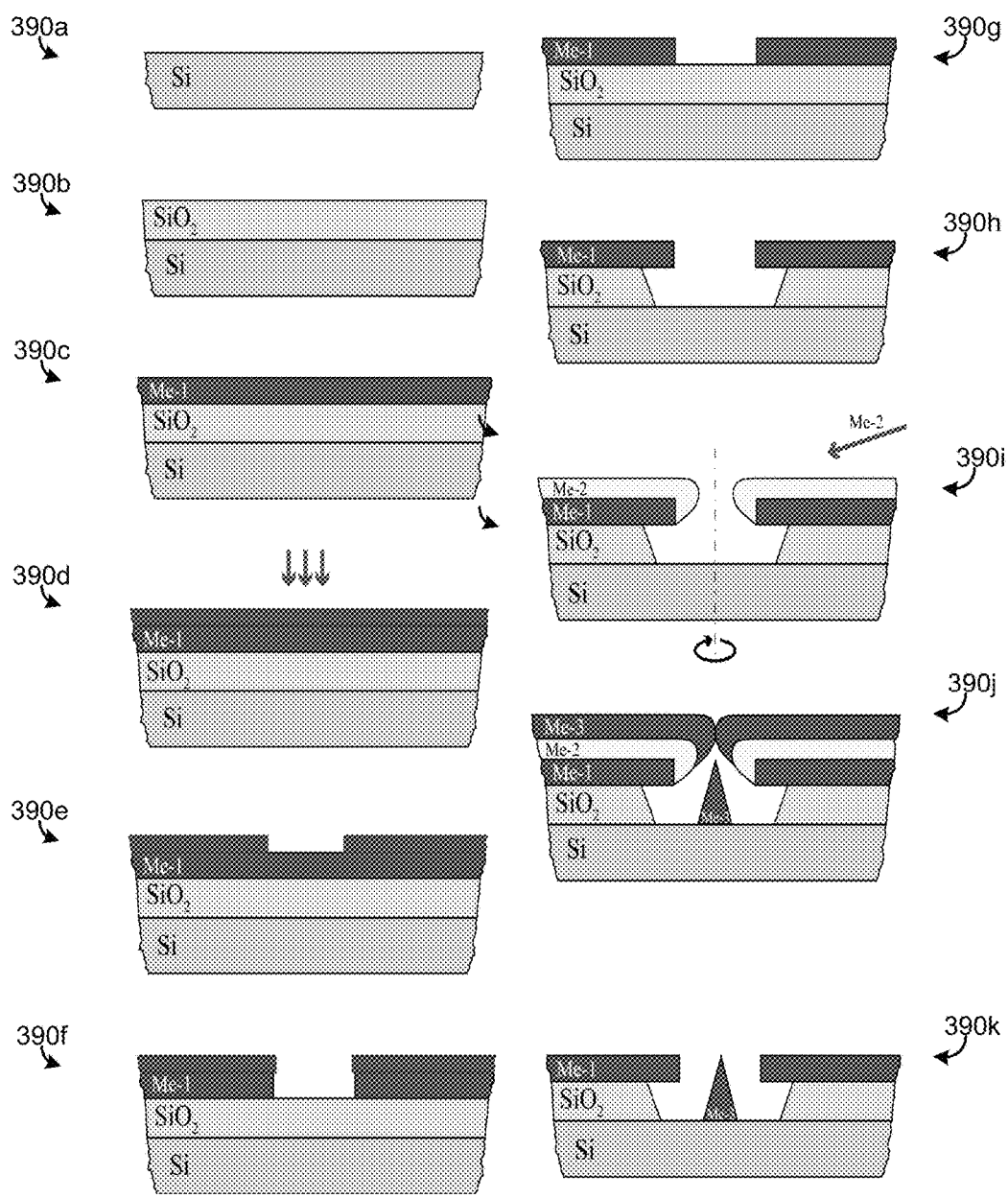
FIG. 8 illustrates a set of stages that may be used in nanotip fabrication.

FIG. 8 illustrates a set of stages 390a-390k that may be used in the fabrication of the nanotip sensor 200 and/or the sensor 102. For clarity, FIG. 8 depicts only one nanotip being fabricated throughout the stages 390a-390k, such as the nanotip sensor 200, although the principles and techniques described with respect to FIG. 8 may easily applied to multiple nanotips. The stages 390a-390k illustrated in FIG. 8 were used to manufacture the nanotip 352 of FIG. 7A and the array of nanotips 360 of FIG. 7B. Although FIG. 8 illustrates a limited number of fabrication stages, other stages may additionally or alternatively used for nanotip and/or sensor fabrication. In FIG. 8, the abbreviation "Me" generically refers to a metal that may be used in the fabrication process, such as aluminum (Al), molybedenum (Mo), etc. Different metals shown in FIG. 8 are distinguished by different numeral suffixes appended to the "Me" abbreviation, e.g., "Me-1," "Me-2," etc.

In a first stage 390a, a silicon (Si) wafer may be cleaned. In a second stage 390b, the Si wafer may be oxidized (e.g., to form a layer of $SiO_2$), and in a subsequent stage 390c, a molybdenum (Mo) thin film may be deposited on the Si wafer, for example, by using an electron beam evaporator. In a stage 390d, a photoresist spin coat may be applied, and in a stage 390e, direct patterning may be applied, for example, by using direct write laser lithography.

During a stage 390f, the photoresist may be developed and inspected. In stages 390g and 390h, Mo and $SiO_2$ etching respectively may be performed. Next, aluminum (Al) thin film deposition at a grazing angle 390i and Mo thin film deposition at a normal angle may be performed 390j, such as by the electron beam evaporator. Finally, lift-off may be performed by aluminum etch 390k.

Use of Nanotip Sensor

Figure 9:
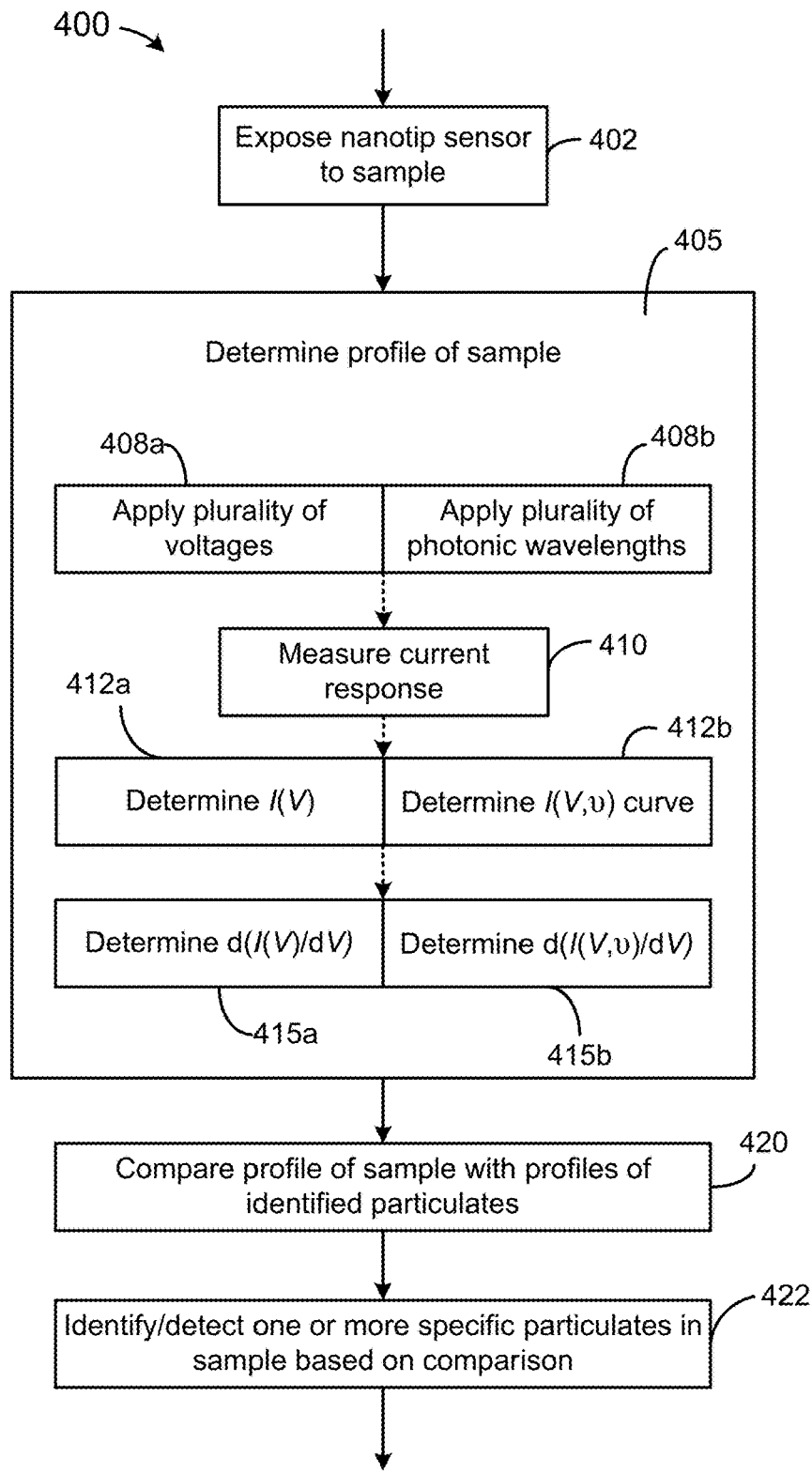
FIG. 9 depicts an example method of using a nanotip sensor to detect or identify particulates in a sample.

FIG. 9 illustrates an example method 400 of using a nanotip sensor to detect and/or identify particulates in a sample. The method 400 may be performed, for example, in conjunction with the system 100, the nanotip sensor 200, and/or other apparatuses and techniques discussed herein. In some embodiments, at least a portion of the method 400 may be performed by executing the computer-executable instructions 157 of FIG. 2. For clarity, the method 400 is described with respect to the system 100 and the nanotip sensor 200.

At a block 402, the sensor 102 may be exposed to a sample. The sensor 102 may include thereon a plurality of nanotips, each with a cathode, an anode, and a gap that is sized commensurate with sizes of particulates that are possible targets for detection. The sample may be a liquid sample, or the sample may be an aerosol sample. In an embodiment, the sensor 102 is enclosed in a chamber 105, and an amount of sample is released into the chamber 105 from a sample source 108. In another embodiment, the sensor 102 need not be enclosed in a chamber 105 in order to be exposed to the sample (block 402), e.g., in embodiments where the sample is environmental or ambient air.

In some embodiments of the method 400, an electrical bias may be applied to the sensor 102 while the sensor 102 is exposed to the sample (block 402). The bias may cause particulates in the sample to adsorb to nanotips of the sensor 102, in a manner such as described with respect to FIG. 2. In some embodiments of the method 400, an electrical bias may not be required to effect adsorption of particulates included in the sample (e.g., when the nanotips are primed), and, therefore, the electrical bias is not applied to the sensor 102 while it is exposed to the sample (block 402).

At a block 405, a profile of the sample may be determined. The profile of the sample may be a conductive spectrum of the sample, in an embodiment. In an embodiment, determining the conductive spectrum of the sample may include applying a plurality or range of voltages may be applied to the sensor 102 (block 408a), and accordingly, to the nanotips included in the sensor 102 and to respective particulates that are adsorbed to the nanotips. At a block 410, a current response may be measured. Data corresponding to the swept voltages at the block 408a and data corresponding to the measured currents the block 410 may be used to determine a I-V characteristic of the sample. For example, the data from blocks 408a and 410 may be fit to determine a current-voltage (I-V) curve of the sample (block 412a). In some embodiments, the I-V curve may be smoothed using a moving average of a numerical difference. At the block 415a, a derivative of the I-V curve of the sample (e.g., d(I(V)/d V)) may be determined. The derivative of the I-V curve of the sample may correspond to the conductive spectrum of the sample, and thus may correspond to the profile of the sample. In some embodiments, the profile or derivative of the I-V curve of the sample may be stored, for example, in the database 115.

In some embodiments, the profile of the may be a conductive-photonic spectrum of the sample. In these embodiments, in addition to sweeping the sensor 102 with a range of voltages (block 408a), a range or plurality of photonic wavelengths may also be irradiated onto the sensor (block 408b), and accordingly, onto the nanotips included in the sensor 102 and onto their respective adsorbed particulates. The swept photonic wavelengths may be irradiated 408b concurrently with the sweeping of the voltages 408a, or the swept photonic wavelengths may be irradiated 408b sequentially with the sweeping of the voltages 408a. The response current may be measured (block 410), and an I-V characteristic of the sample may be determined. For example, an I(V, u) curve may be determined (block 412b) using curve fitting techniques as previously discussed. At the block 415b, a derivative of the I(V, u) curve may be determined. The derivative of the I-V-u curve of the sample may correspond to the conductive-photonic spectrum of the sample, and thus may correspond to the profile of the sample. In some embodiments, the profile or derivative of the I(V, u) curve of the sample may be stored, for example, in the database 115.

At a block 420, the profile of the sample determined at the block 405 may be compared with one or more profiles of identified, known particulates. The profiles of the identified, known particulates may be retrieved from the database 115, for example, and various aspects of the known profiles and the profile of the sample may be compared. For example, inflection points in the data, the smoothed data, and/or the derivatives and numerical differences in the data may be compared with those included in the one or more profiles of the identified, known particulates. Additionally, magnitudes of signals in the data, the smoothed data and the derivatives and numerical differences in the data may be compared and considered. For example, a very small or no signal may indicate no bridging, whereas a larger signal with few features may indicate aggregate bridging of a same type of particulate. Still further, peak sizes in the data, the smoothed data and the derivatives and numerical differences in the data may be compared to those of the one or more profiles of the identified, known particulates.

At a block 422, one or more types of specific particulates that have been adsorbed to the nanotips of the sensor 102 may be determined based on the comparison performed at the block 420, and thus be detected or identified as being present in the sample. The determination of the one or more types of specific particulates (blocks 420 and 422, respectively) may be performed using any known statistical analysis technique or combinations thereof. For example, statistical analysis may be used on a signal obtained from a sensor 102 to distinguish and separate out individual profiles of multiple adsorbates.

Figure 10:
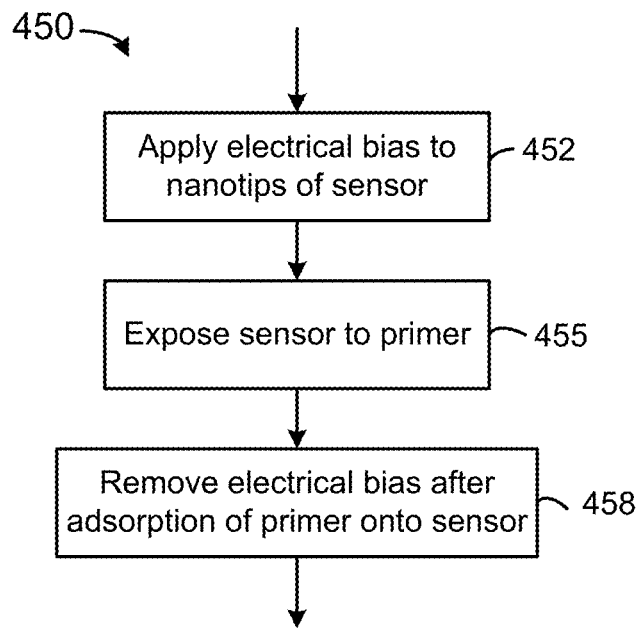
FIG. 10 depicts an example method of priming nanotips of a sensor.

FIG. 10 illustrates an embodiment of a method 450 of priming nanotips of a sensor 102. The method 450 may be performed, for example, in conjunction with the system 100, the nanotip sensor 200, and/or other apparatuses and techniques discussed herein. In an exemplary embodiment, the method 450 is performed prior to execution of the method 400 of FIG. 9. In some embodiments, at least a portion of the method 450 may be performed by executing the computer-executable instructions 157 of FIG. 2. For clarity, the method 450 is described with respect to the system 100 and the nanotip sensor 200.

At a block 452, an electrical bias may be applied to the nanotips of the sensor 102. For example, the voltage source 110 may generate a low-level voltage to generate the bias. At a block 455, the sensor 102 may be exposed to a stream or flow of primer suspended in a liquid or in aerosol form. The primer may include, in an embodiment, one or more types of antibodies corresponding to one or more types of target particulates for detection or identification. In another embodiment, the primer may include one or more types of nucleic acid fragments (e.g., DNA fragments or RNA fragments) that correspond to the one or more target particulates. In an embodiment, the sensor 102 is enclosed in a chamber 105, and an amount of primer is released into the chamber 105. The bias applied at the block 452 may cause the primer to adsorb to at least a portion of the plurality of nanotips of the sensor 102. After adsorption of the primer, the electrical bias may be removed (block 458). The method 450 may then proceed to block 402 of the method 400, where the primed sensor 102 is exposed to the sample.

Figure 11:
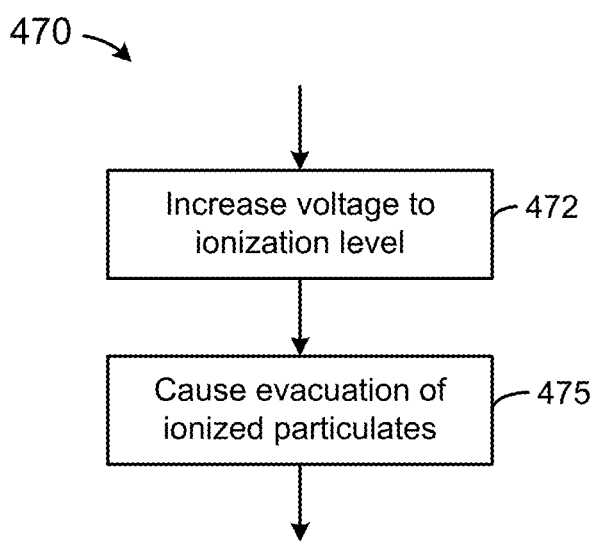
FIG. 11 depicts an example method of cleaning a sensor.

FIG. 11 illustrates an embodiment of a method 470 of cleaning the nanotips of a sensor 102. The method 470 may be performed, for example, in conjunction with the system 100, the nanotip sensor 200, and/or other apparatuses and techniques discussed herein. In an exemplary embodiment, the method 470 may be performed after execution of the method 400 of FIG. 9. In some embodiments, at least a portion of the method 470 may be performed by executing the computer-executable instructions 157 of FIG. 2. For clarity, the method 470 is described with respect to the system 100 and the nanotip sensor 200.

At a block 472, a voltage may be applied to the sensor 102 (and, accordingly, to the nanotips of the sensor 102 and any particulates that are adsorbed thereon). The applied voltage may be greater than the voltage used for an electrical bias (e.g., as discussed with respect to the block 452 of FIG. 10 or the block 402 of FIG. 9). In fact, the applied voltage may be increased to a level that causes any adsorbed particulates to be ionized (e.g., an ionization level or ionization voltage).

The ionized particulates may be repelled or desorbed from the nanotips and may be released into the stream or into chamber 105. At a block 475, the desorbed particulates may be caused to evacuate from the chamber 105. For example, an activation of the vacuum system 120 may cause the stream or flow (including any desorbed particulates) to be evacuated from the chamber 105.

Population of Database and Blind Testing

An embodiment of a prototype nanotip sensor for detecting and identifying particulates in a sample was fabricated using the techniques of FIG. 8. An image 382 of a single nanotip of the fabricated sensor and an image 385 of a portion of the nanotip array of the fabricated sensor are provided in FIGS. 7A and 7B, respectively. The fabricated nanotip sensor included 250,000 nanotips on a chip whose sides each measured 1.0 cm in length or less.

The fabricated sensor was included in an embodiment of a prototype system for detecting and identifying particulates in a sample. The prototype system included a chamber that enclosed the nanotip sensor. The chamber was in fluid communication with a small vacuum system capable of pulling a pressure of several Torr on a volume of a few cubic centimeters of the sensor chamber. A variable voltage source with a range of 0V to 10V and a picoammeter were electrically connected with the nanotip sensor. A sweepable monochromatic light source with a range of far-IR to far-UV was directed to irradiate upon the nanotip sensor, and a computer/microcontroller was electrically connected with the voltage source, the picoammeter and the light source. A computer program to control the variable voltage source and the picoammeter was stored in the memory of the computer. The system was powered by a standard 110V connection, however, the system may be powered by a 220V connection, by a battery, or by some other type of electrical storage device. The entire system 100 may fit into a space approximately the size of a briefcase, thus having a size suitable for field use.

Figure 12A:
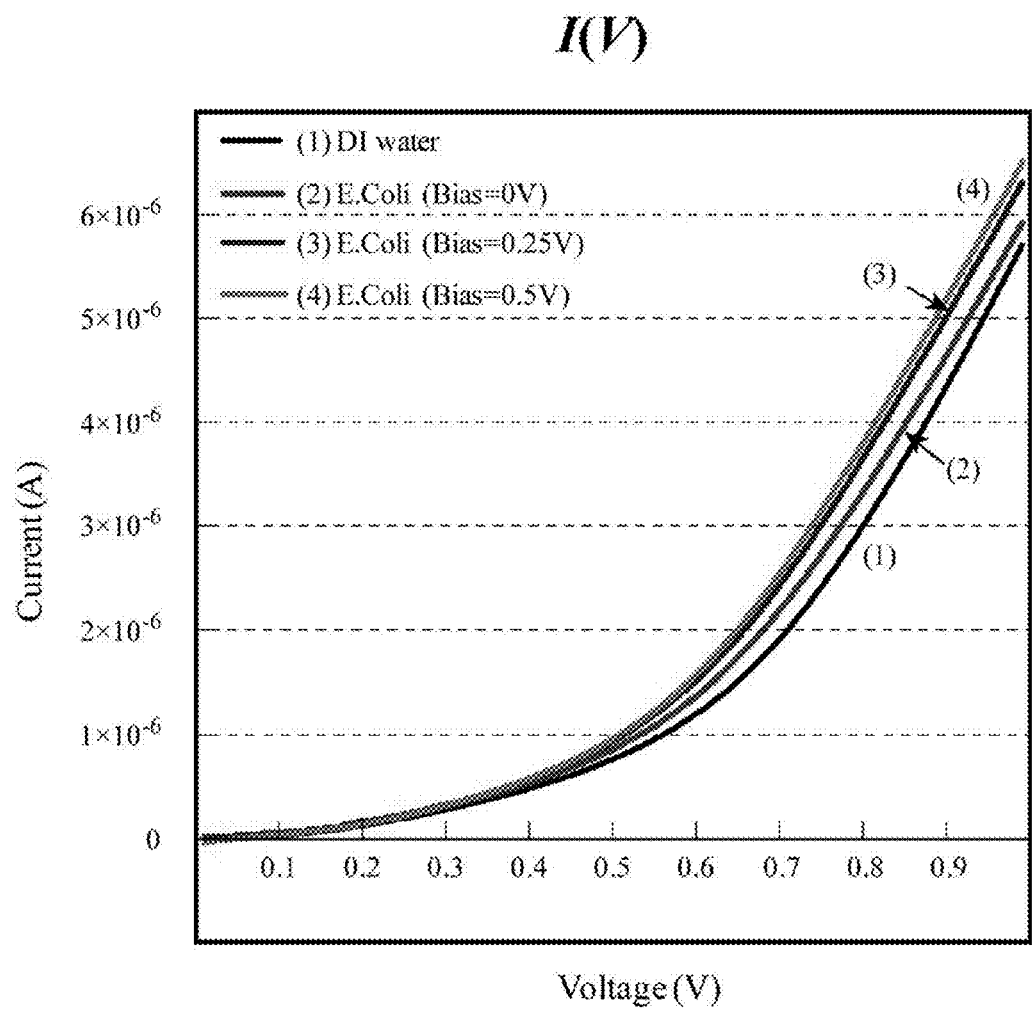
FIGS. 12A-12D shows measured current-voltage (I-V) characteristics of four different live bacteria as detected by a prototype fabricated nanotip sensor.
Figure 12B:
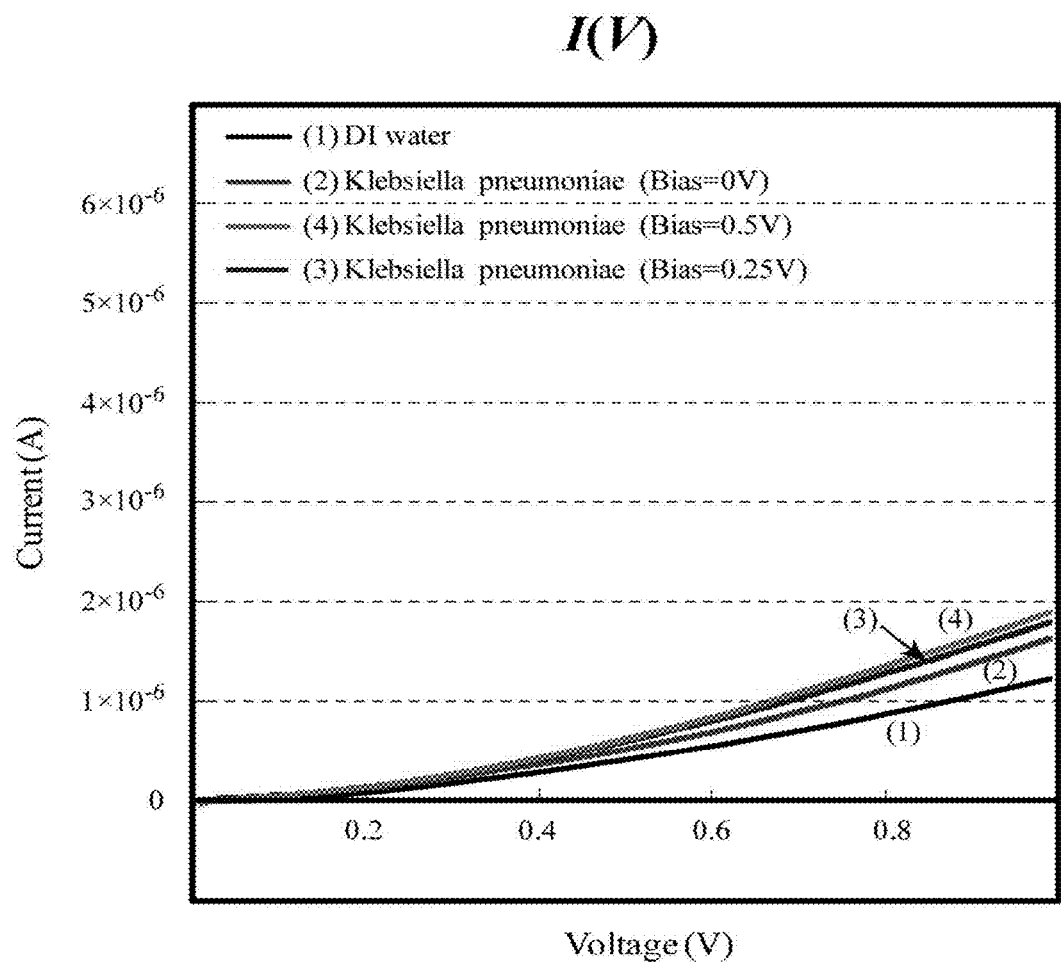
Figure 12C:
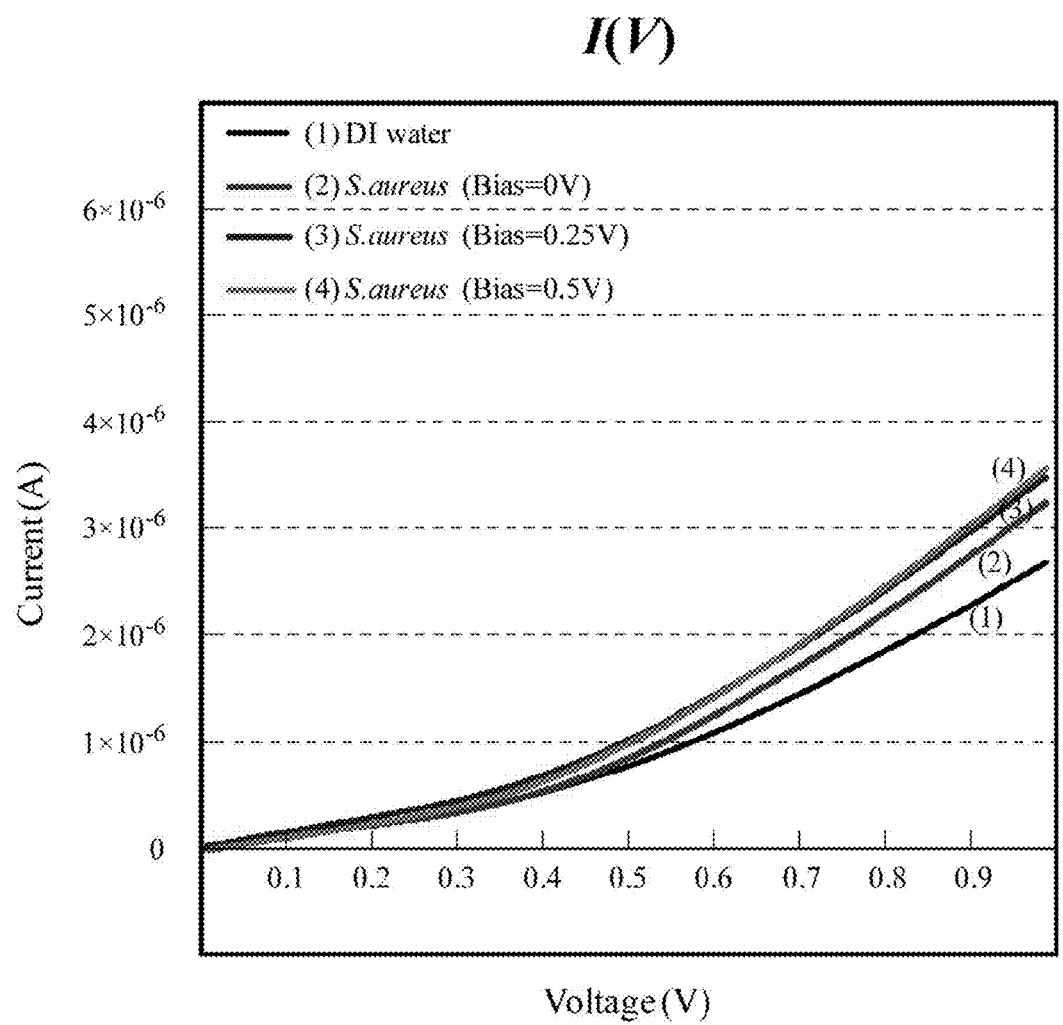
Figure 12D:
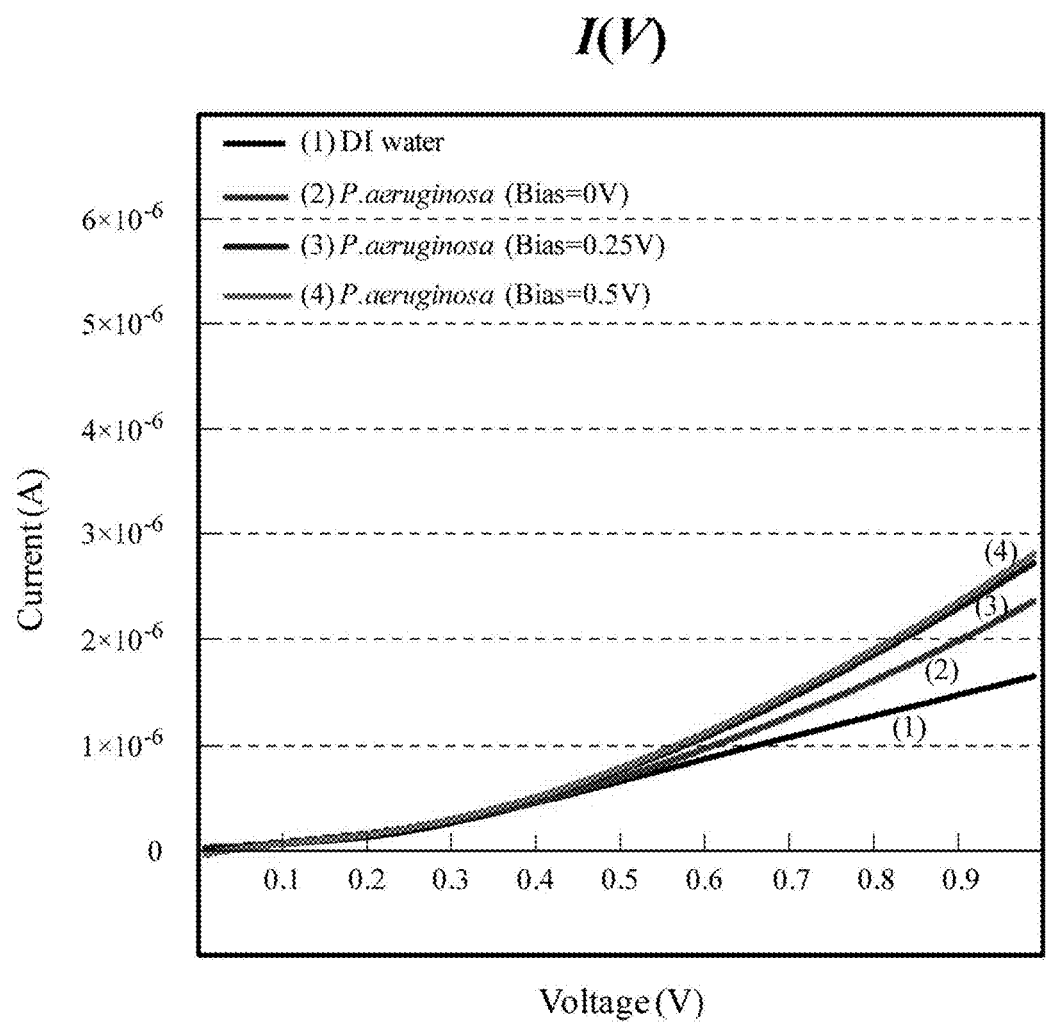
Figure 13A:
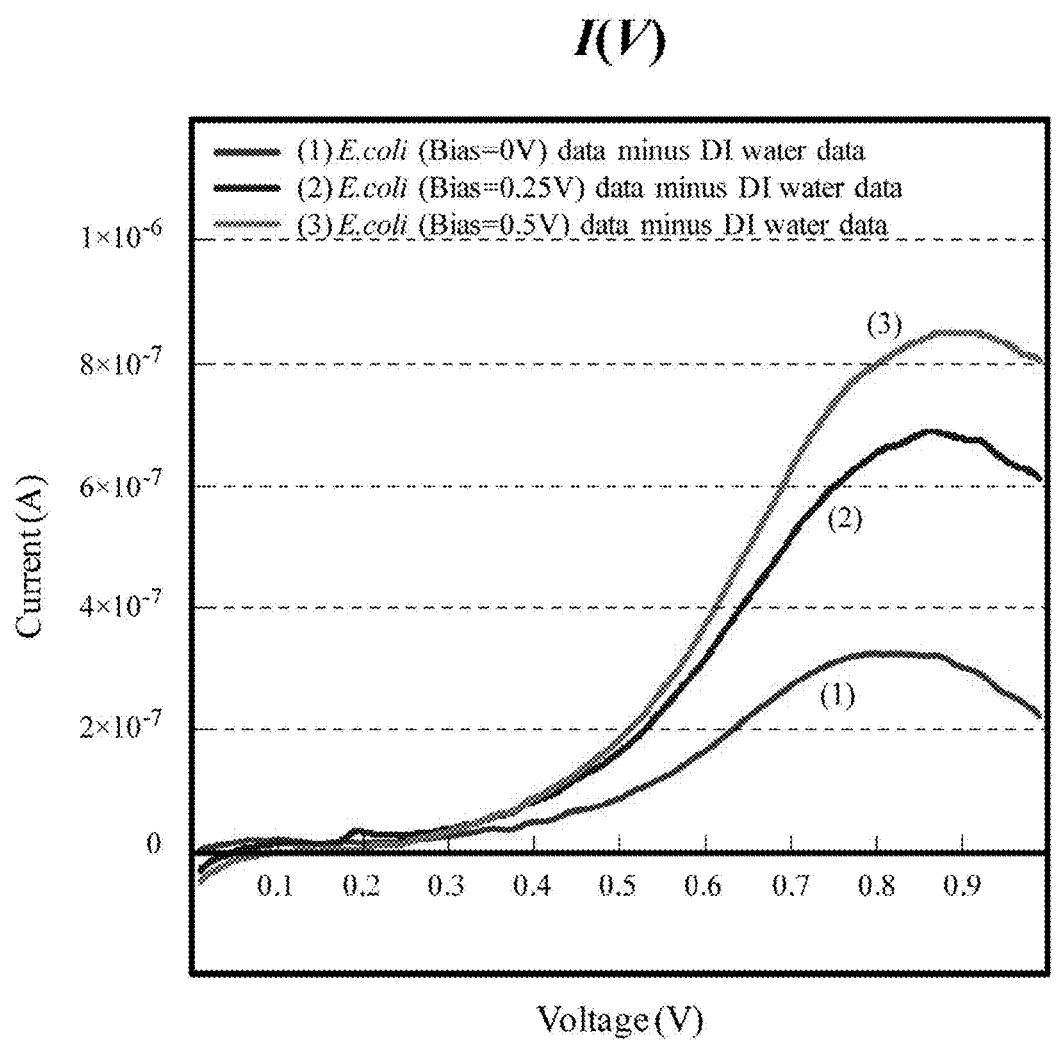
FIGS. 13A-13D illustrate the I-V characteristic curves of FIGS. 12A-12D with a base curve corresponding to de-ionized (DI) water subtracted.
Figure 13B:
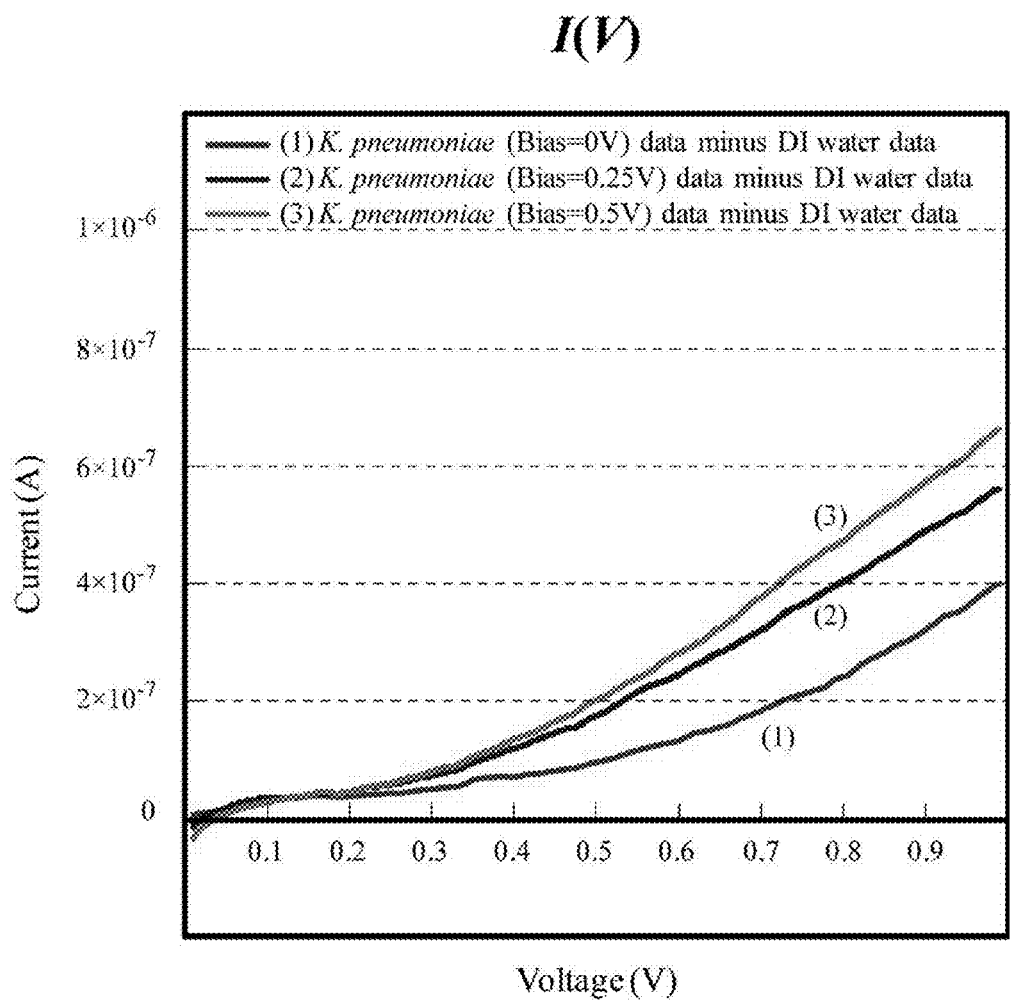
Figure 13C:
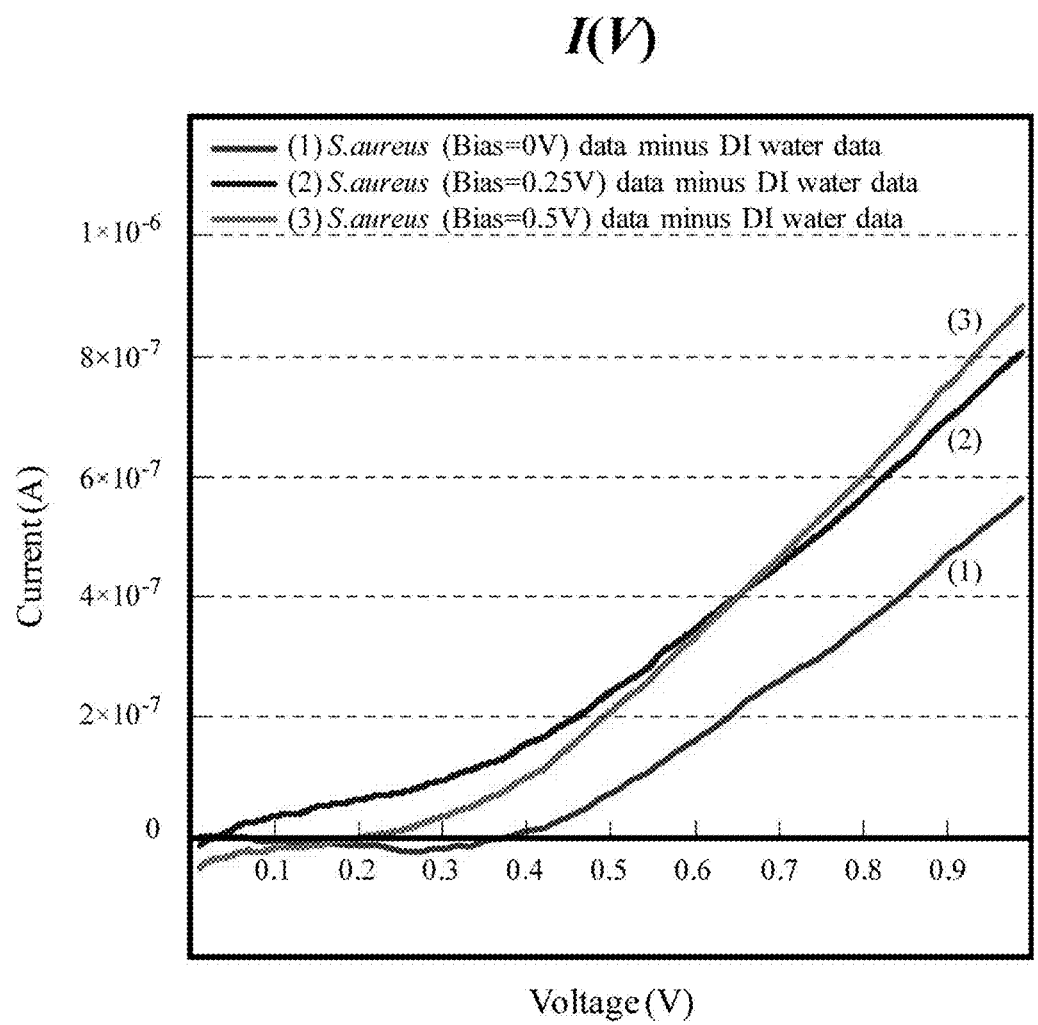
Figure 13D:
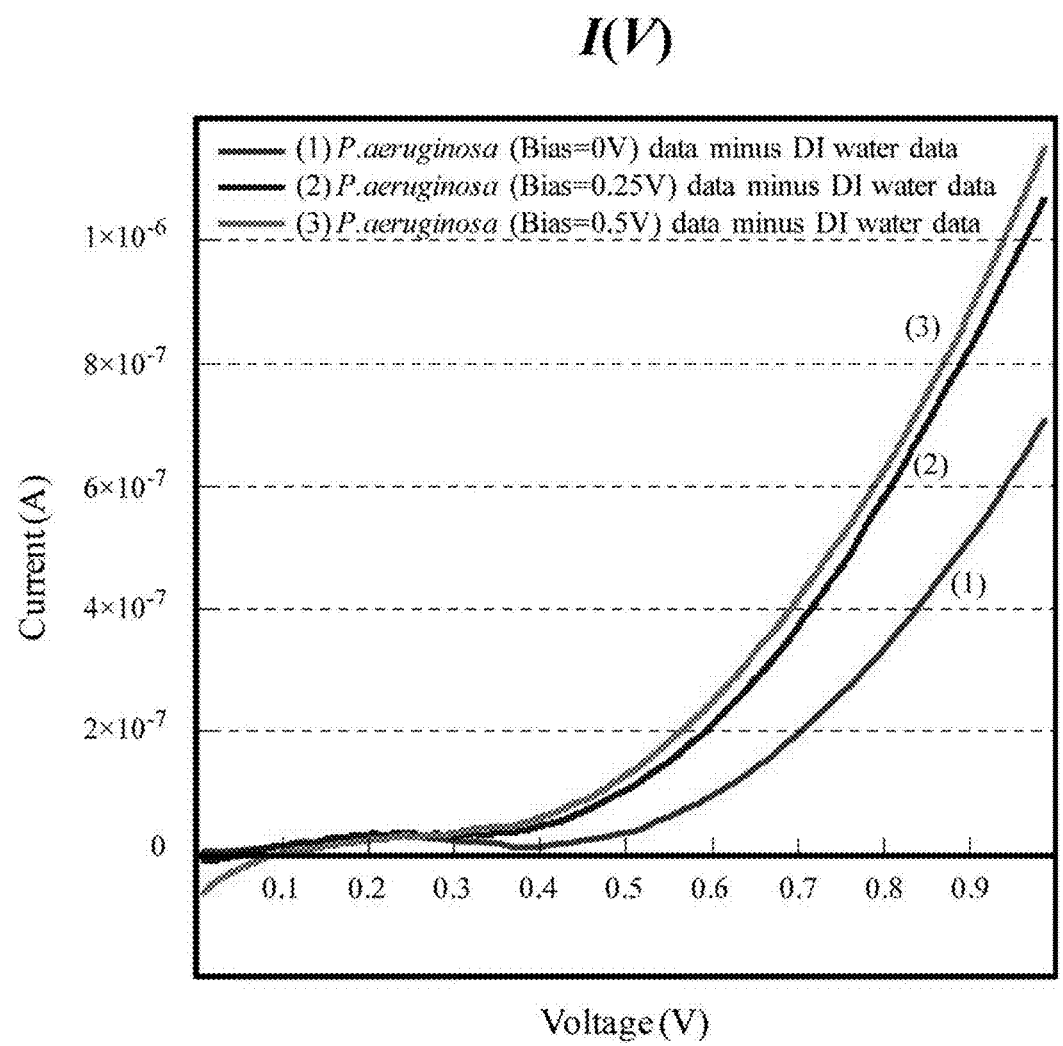
Figure 14A:
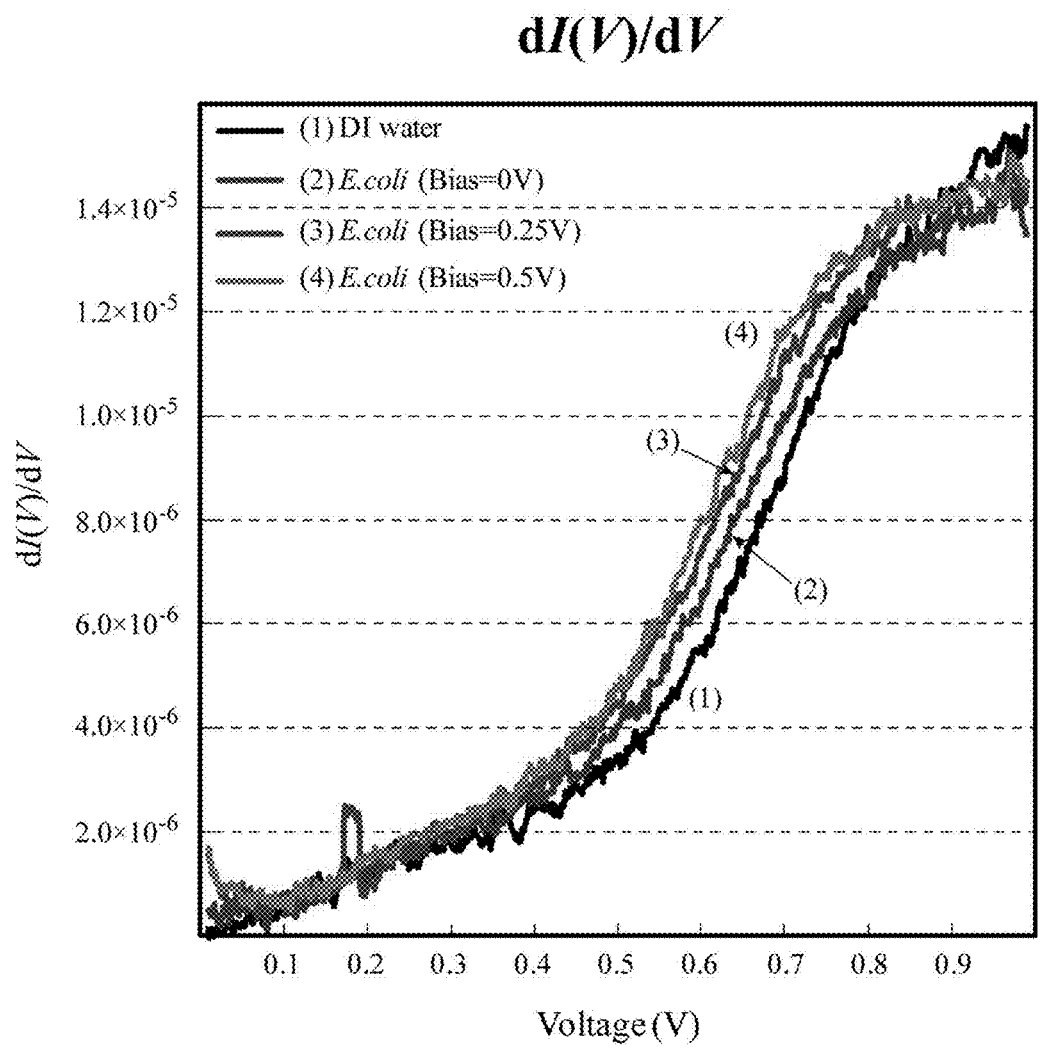
FIGS. 14A-14D illustrate the respective derivatives of the measured I-V characteristic curves of FIGS. 12A-12D.
Figure 14B:
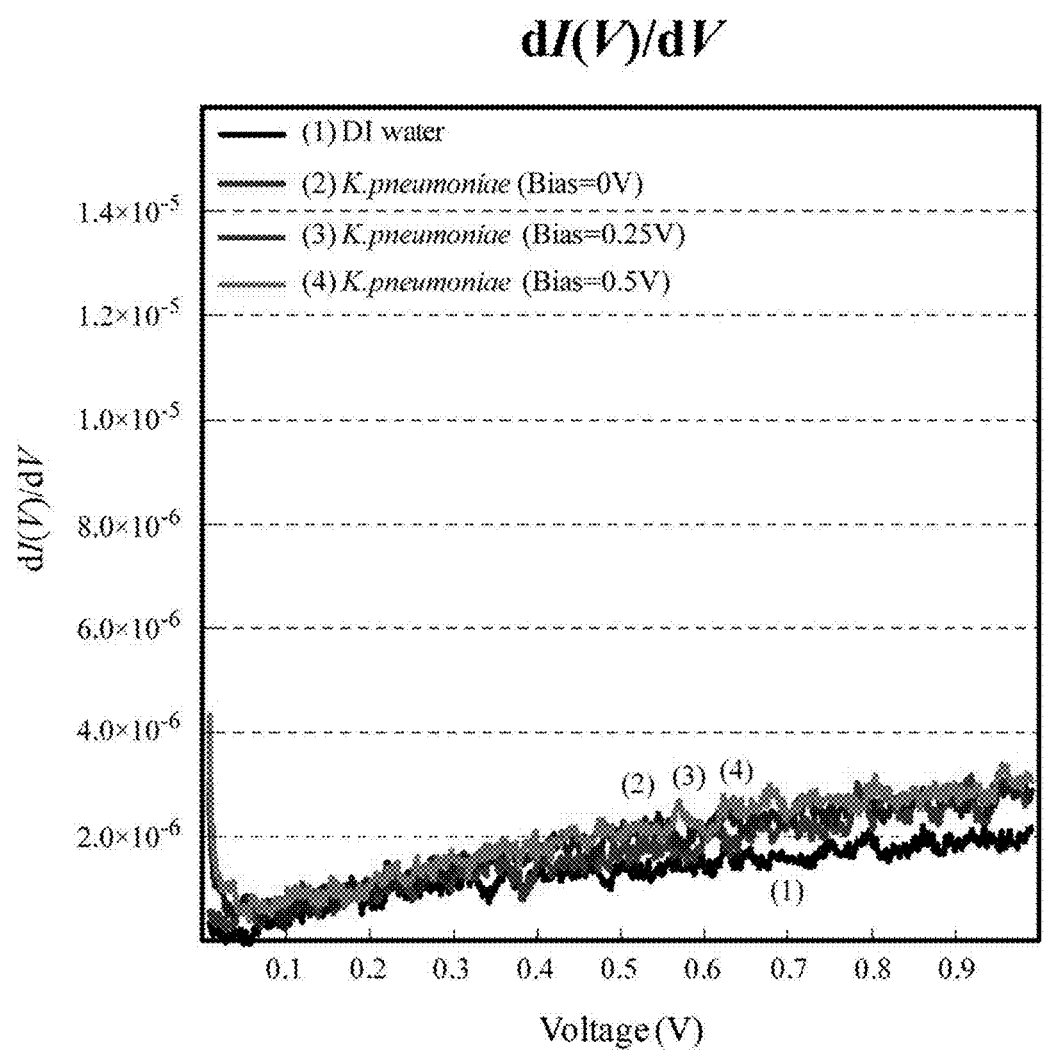
Figure 14C:
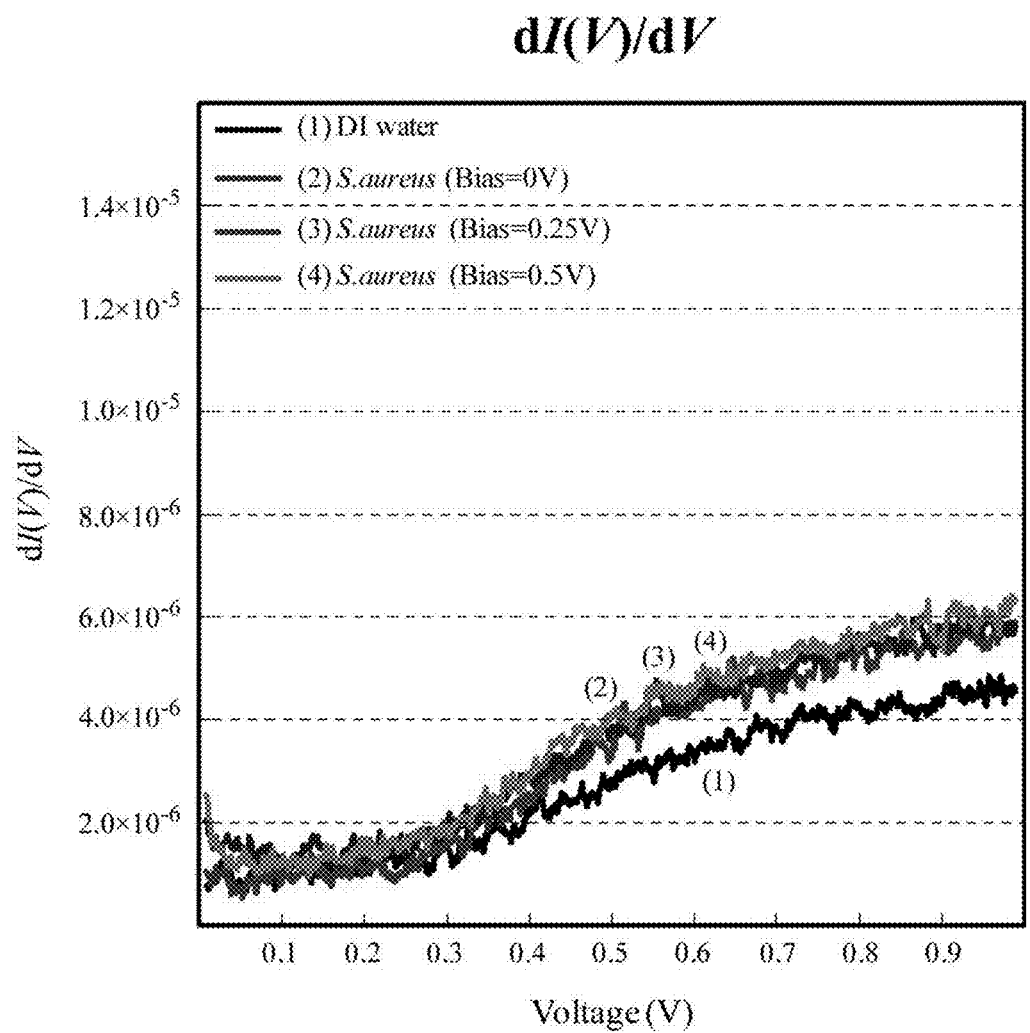
Figure 14D:
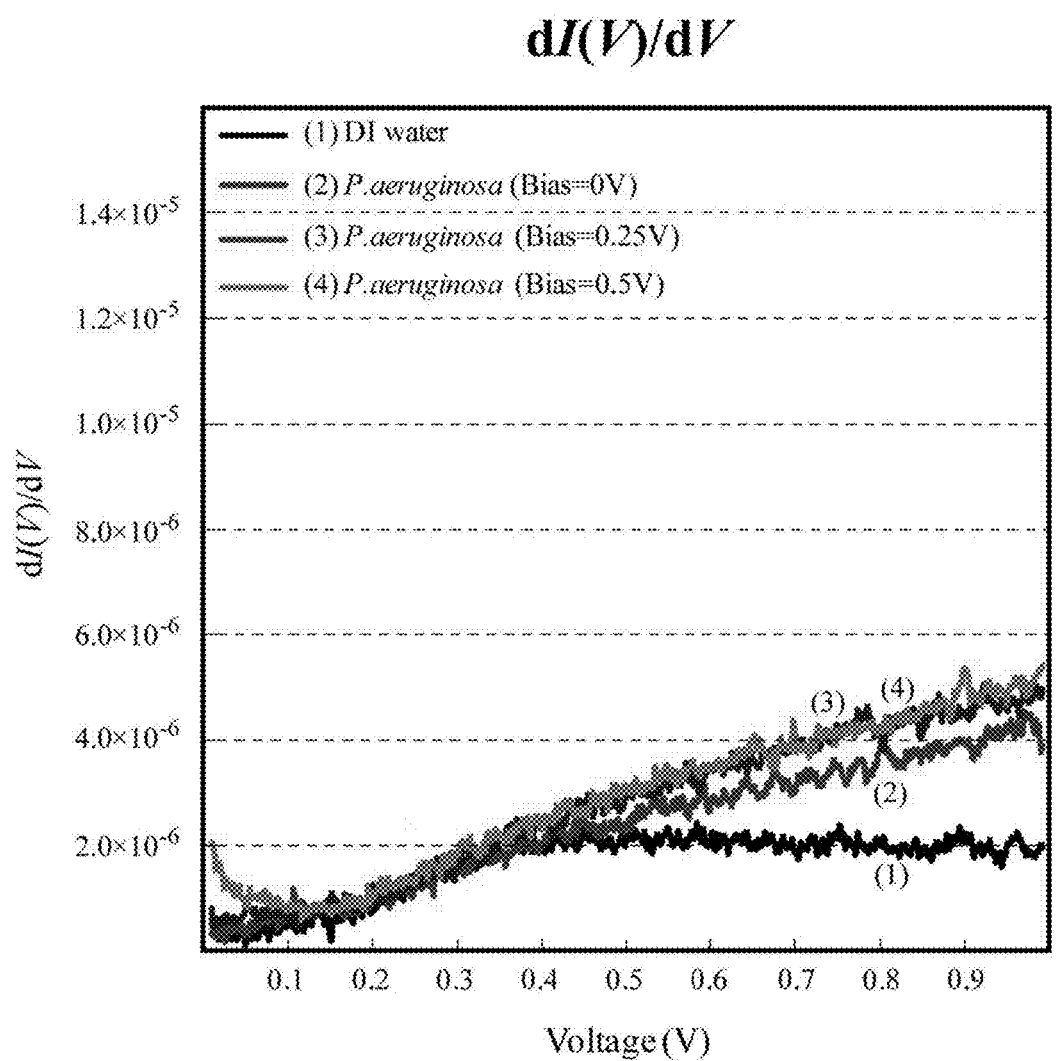
Figure 15A:
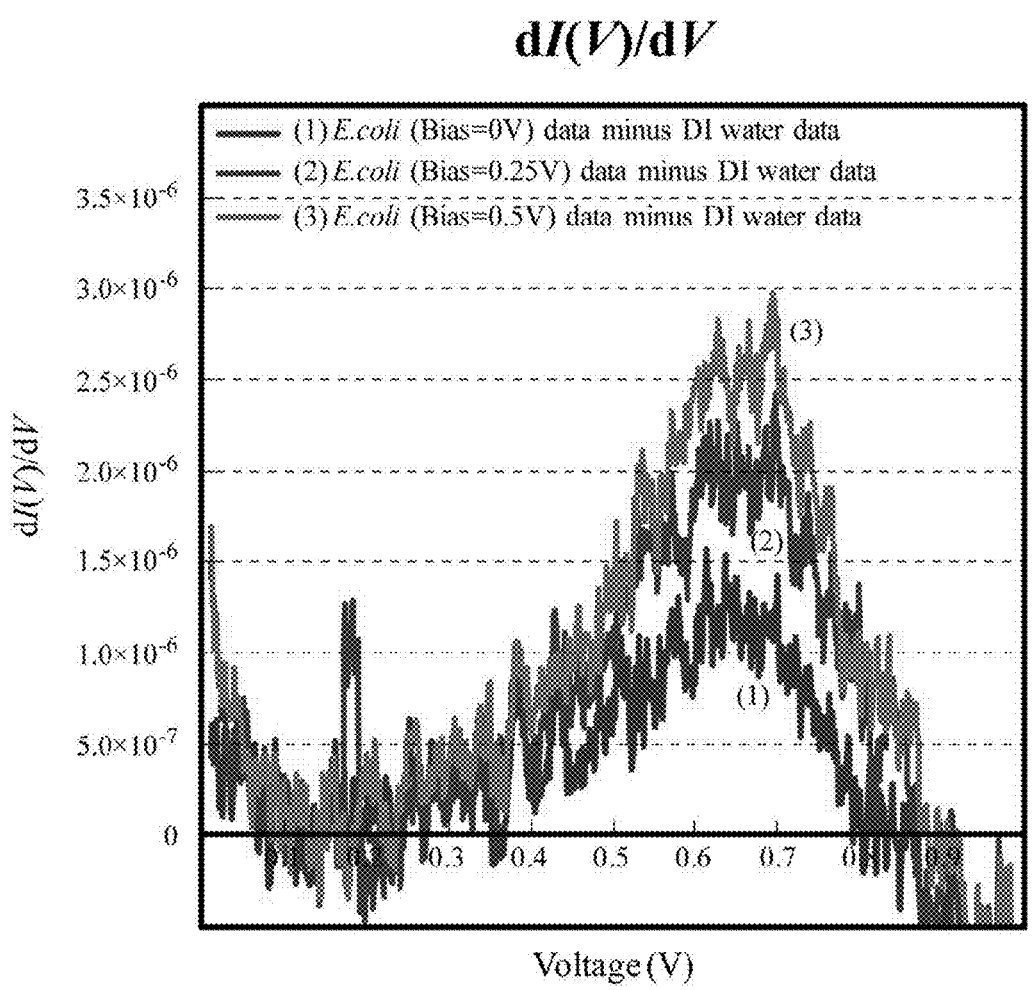
FIGS. 15A-15D illustrate the respective derivatives of the curves shown in FIGS. 13A-13D)
Figure 15B:
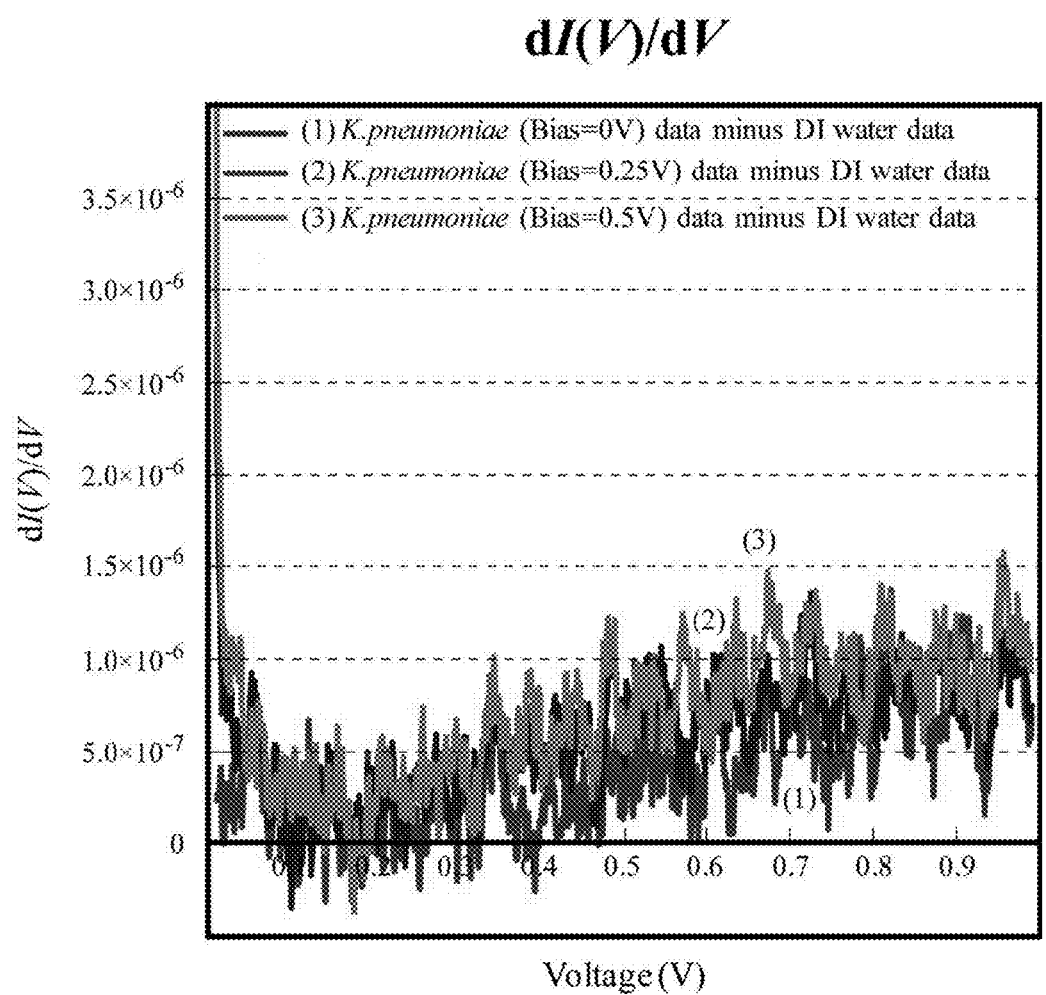
Figure 15C:
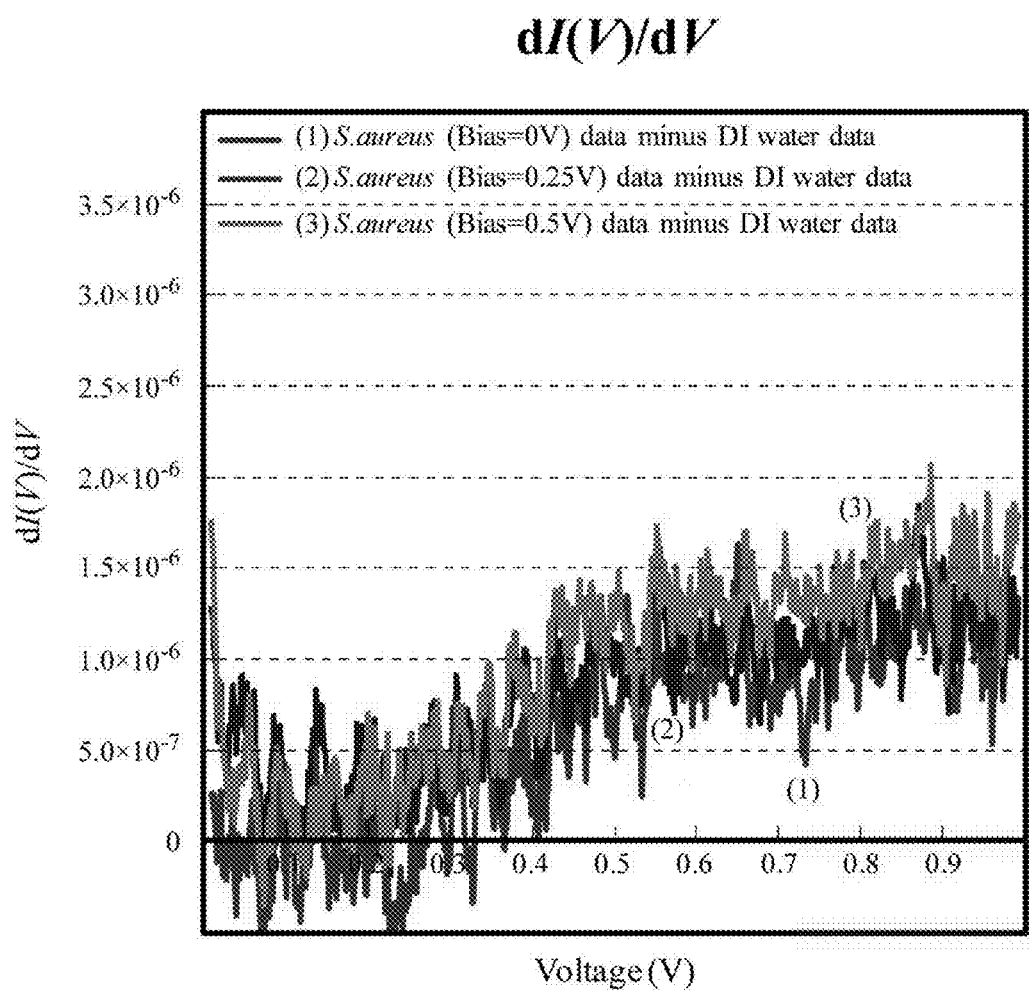
Figure 15D:
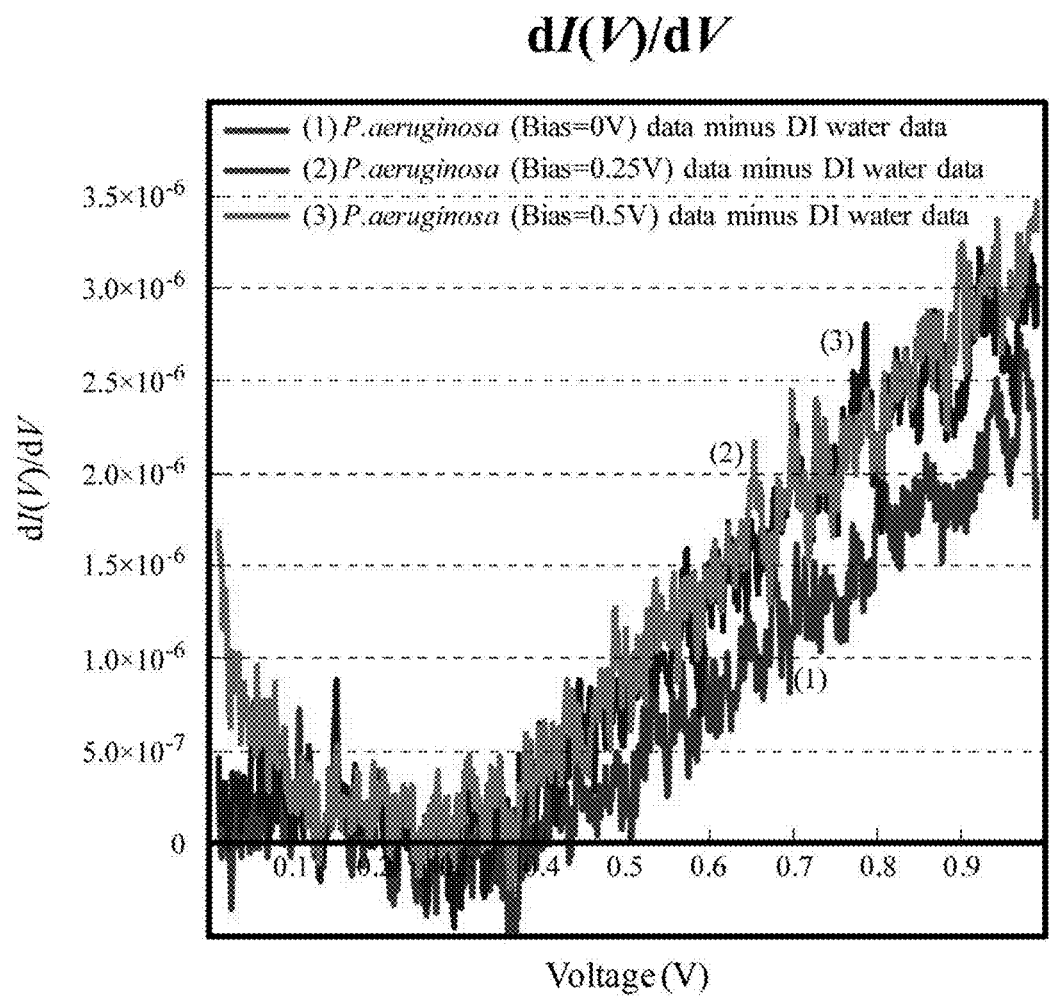

FIGS. 12A-12D shows I-V characteristics (e.g., I(V)) of four different live bacteria as detected by the fabricated nanotip sensor. FIG. 12A shows the I-V characteristic of *E. coli* bacteria; FIG. 12B shows the I-V characteristic of *K. pneumoniae*; FIG. 12C shows the I-V characteristic of *S. aureus*; and FIG. 12D shows the I-V characteristic of *P. aeruginosa*. The current and voltage axis scales are the same on all plots. Curves marked as (1) correspond to I-V characteristics of a clean nanotip sensor array with only DI water (30 μl) applied. Curves marked as (2) correspond to I-V characteristics that were taken with 10 μl of bacteria solution, with no applied voltage bias prior to the measurement. Curves marked as (3) correspond to I-V characteristics that were taken after a 0.25 V bias was applied to the nanotip sensor for 3 minutes, and curves marked as (4) correspond to I-V characteristics that were measured after a 0.5 V bias was applied for 3 minutes. Additional measurements were taken after biases of 0.75 V and 1 V were each applied to the nanotip sensor array (respectively) for 3 minutes, although this data is not shown.

FIGS. 13A-13D illustrate the I-V characteristic curves of FIGS. 12A-12D with the base curve (e.g., the curve corresponding to DI water) subtracted. FIGS. 14A-14D illustrate the respective derivatives of the I-V characteristic curves of FIGS. 12A-12D (e.g., d(I(V)/d V), and FIGS. 15A-15D illustrate the respective derivatives of the I-V characteristic curves with the base curve for DI water subtracted (e.g., the derivatives of the curves shown in FIGS. 13A-13D). A database such as the database 115 was populated with the data shown in FIGS. 12A-12D, 13A-13D, 14A-14D and 15A-15D.

Figure 16:
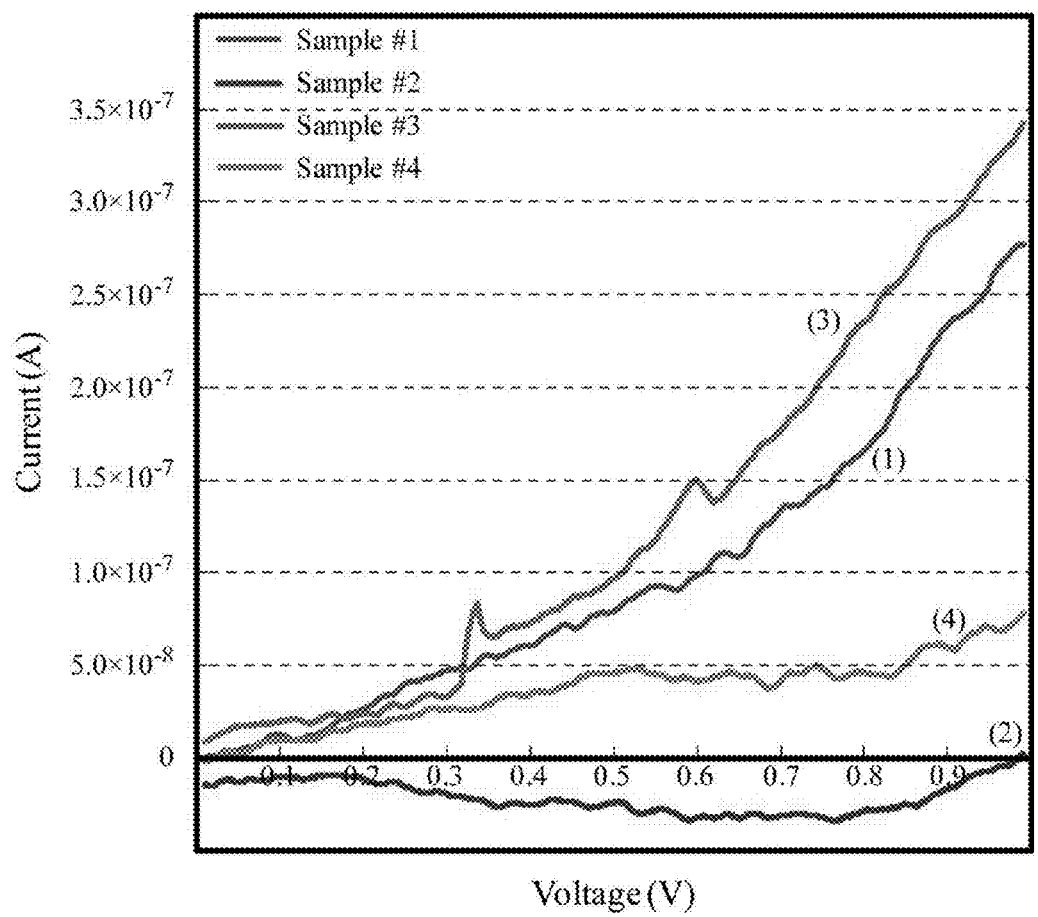
FIG. 16 illustrates the I-V characteristic curves of four unlabeled, unknown samples with the base curve for DI water subtracted.
Figure 17A:
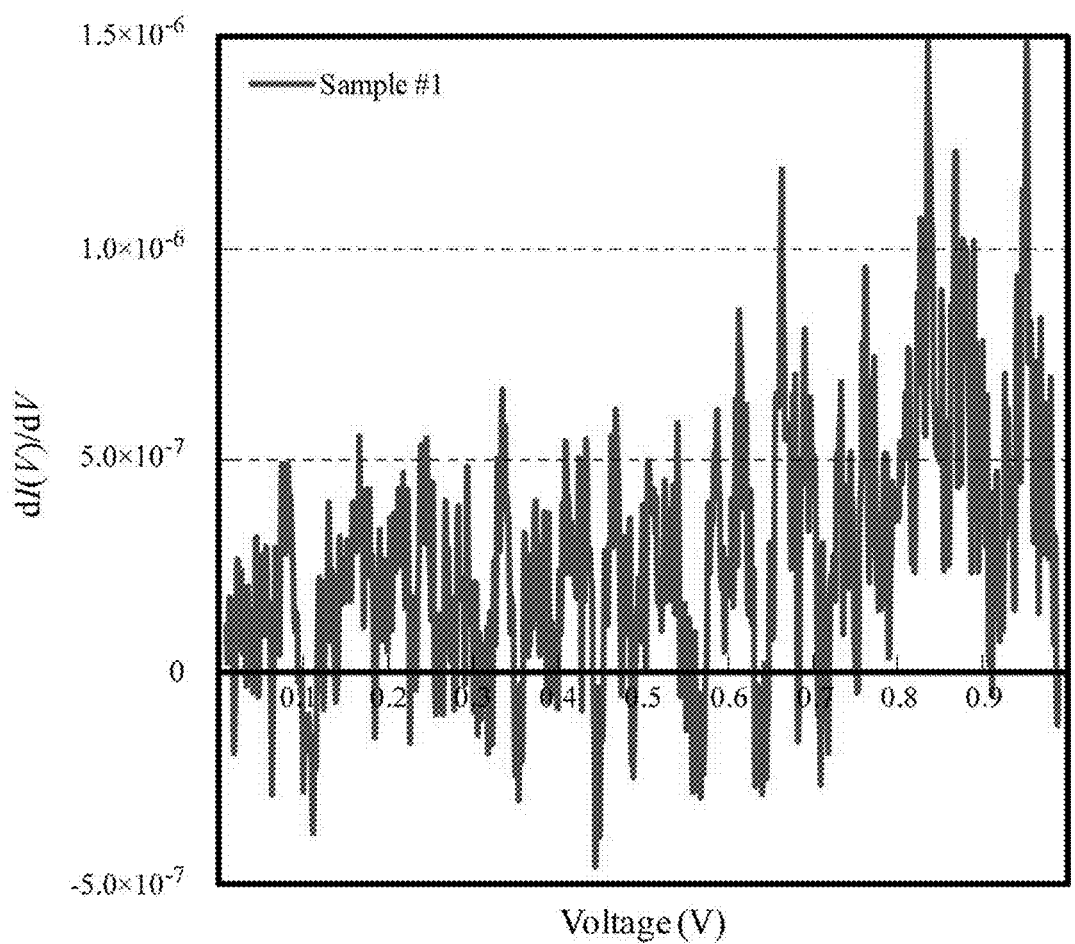
FIGS. 17A-17D illustrate the derivatives of the curves shown in FIG. 16.
Figure 17B:
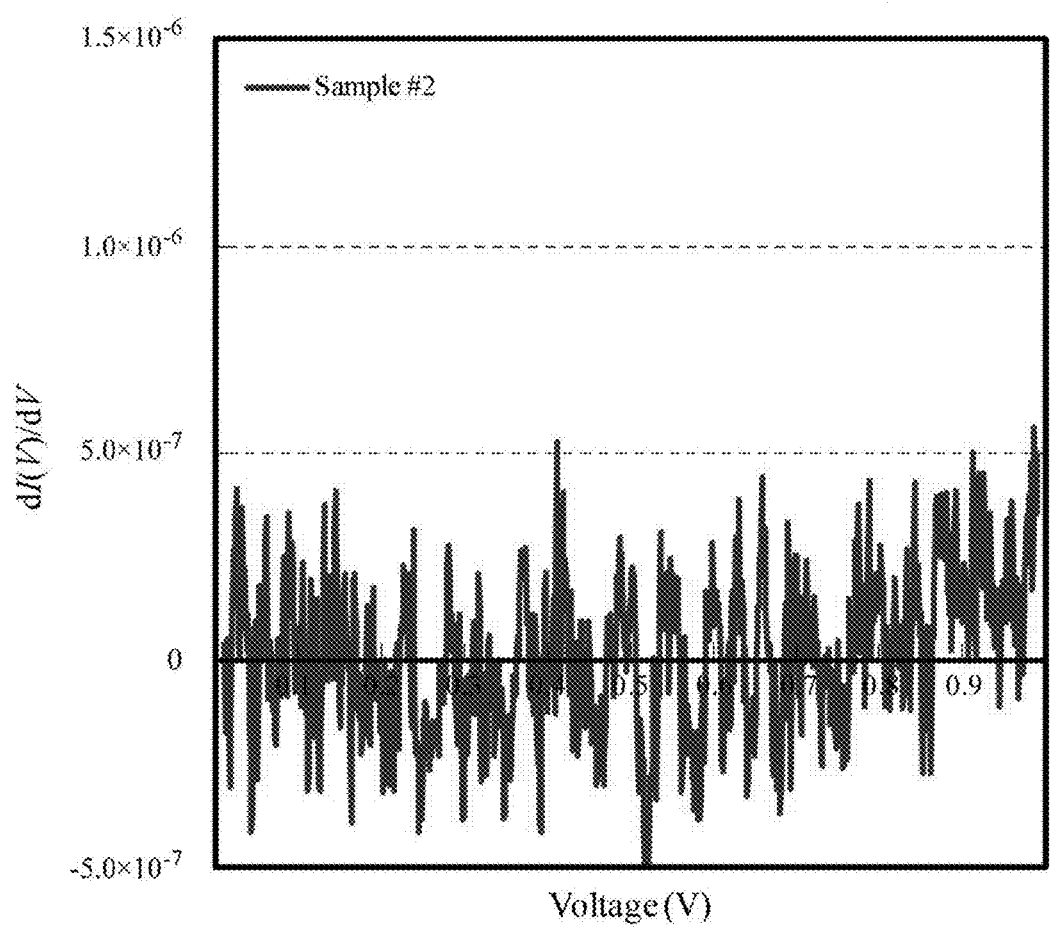
Figure 17C:
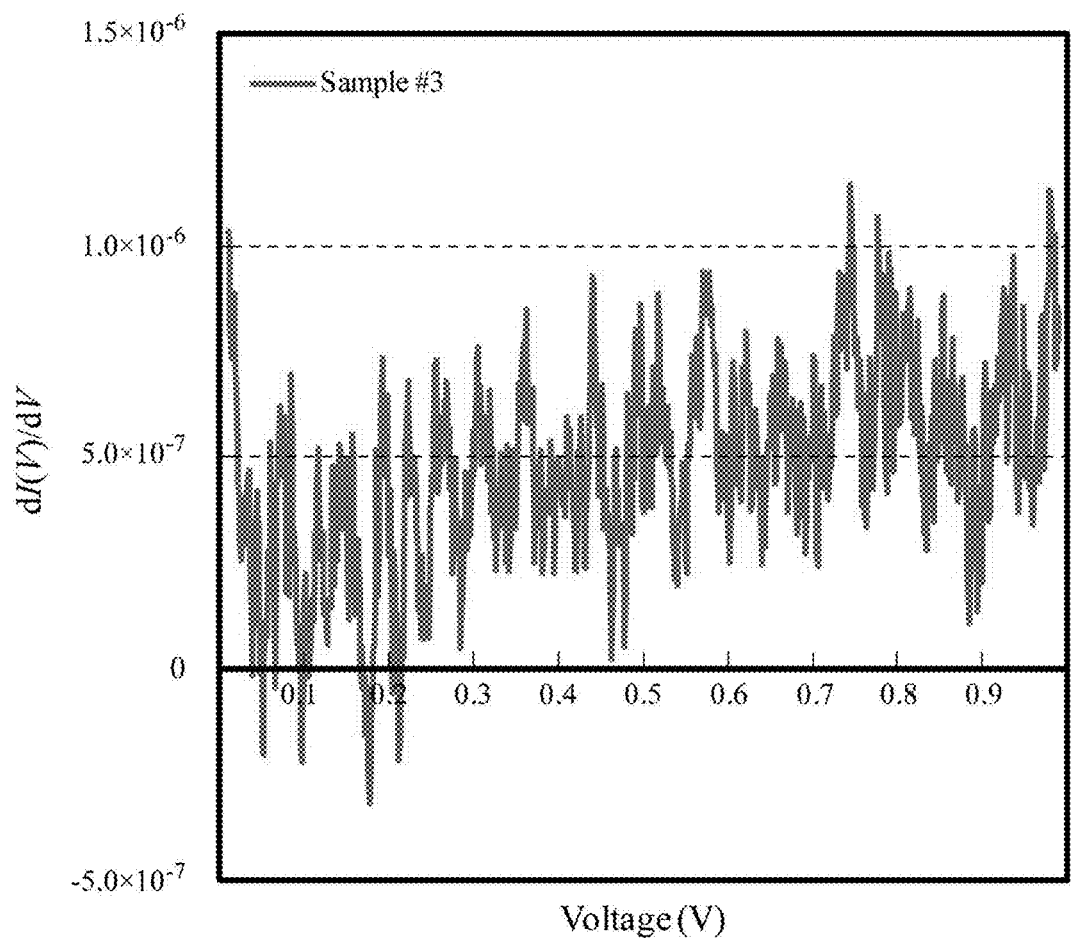
Figure 17D:
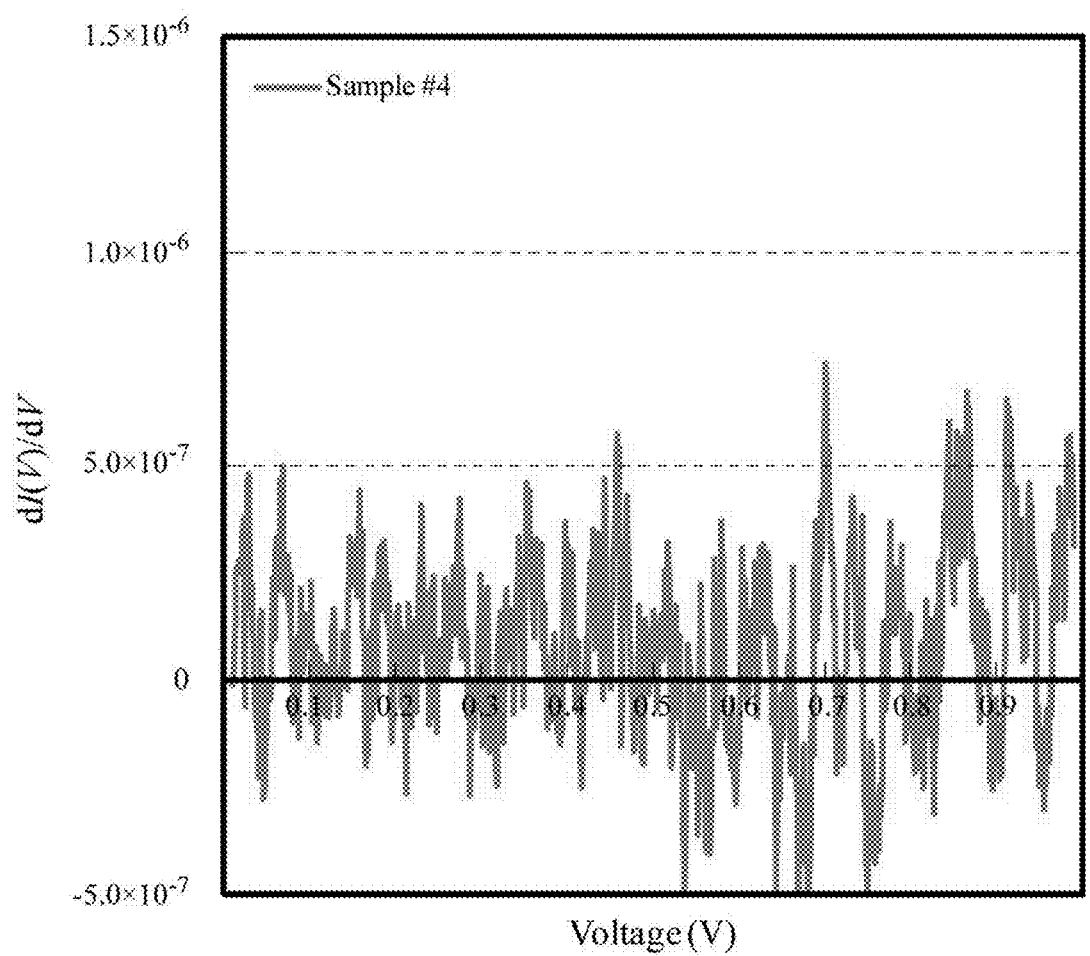

Blind testing was performed on four unlabeled samples. The same nanotip sensor was used to test all four unlabeled samples. Between each test, the fabricated nanotip sensor was cleaned using a method such as described in FIG. 11. For each of the four unlabeled samples, the resulting I-V characteristic curve with the base DI-water curve subtracted is shown in FIG. 16. Each curve in FIG. 16 is labeled with the sample number to which it corresponds, e.g., "(1)" identifies the curve corresponding to unknown sample #1. FIGS. 17A-17D show the derivatives of the I-V characteristic curves of the four unlabeled samples with base curve for DI water subtracted. When the sample curves were compared with the data stored in the database, all four unlabeled samples were correctly identified. In particular, Sample 1 was identified as *E. coli*, Sample 2 was identified as *K. pneumonia*, Sample 3 was identified as *P. aeruginosa*, and Sample 4 was identified as *S. aureus*. Of note, even differing bacteria of a similar size (e.g., *E. coli* and *P. aeruginosa*) were positively identified by their differing I-V characteristics and their differing d(I(V)/d V) characteristics.

The database population and blind tests were performed using a particular system prototype configuration for detecting or identifying particulates in a sample. However, the system 100 is not limited to only the prototype configuration. The system may be easily adapted to efficiently detect other types or species of particulates.

For example, although the fabricated, prototype nanotip sensor included 250,000 nanotips on a chip whose sides each measured 1.0 cm in length or less, the number of nanotips on a chip may be of a smaller or a greater number. For example, the chip may include 160,000 or more nanotips. In another example, the number of nanotips may easily be increased above 250,000 using readily known commercial techniques to further increase signal strength. The footprint of the chip may be enlarged or may be decreased. In some embodiments, single chip may include nanotips of differing gap sizes to detect differently-sized particulates.

In another example, during the blind testing, the levels of low bias applied to the sensor to effect adsorption of particulates in the sample were 0.25V, 0.5 V, 0.75V and 1.0 V. However, other levels of low bias voltage may be used to effect adsorption, and furthermore, either positive or negative biases may be used to effect adsorption. In some cases, instead of selecting a discrete voltage level for low-level bias, a range may be selected (e.g., bias voltage ranging between 0.25 V and 0.5 V, between 0.75V and 1.5V, etc.). The level or range of low bias voltage that is selected may depend, in part, on a geometry of the nanotip (e.g., size and/or shape), the potential target particulate(s), the medium in which the sample is suspended, the carrier(s) to which potential target particulate(s) are attached, and other factors.

Similarly, the time interval over which the low bias voltage is applied need not be limited to three minutes, as used in the database population and blind tests. Any desirable time interval may be used to effect adsorption. The selected time interval may depend on factors such as a geometry of the nanotip (e.g., size and/or shape), the potential target particulate(s) and its polarizability, the medium in which the sample is suspended, the carrier(s) to which potential target particulate(s) are attached, as well as other factors. In fact, in some embodiments, the low bias voltage to effect adsorption may be increased into the voltage sweep range, and then still further into the ionization range without demarcation between the voltage ranges, so that the level of low bias voltage and the time interval length of its application to the nanotip sensor is of less importance.

Furthermore, although the plurality of swept voltages in the blind testing ranged from 0 to 1.0 V, other voltage ranges may be selected for use with the techniques of the present disclosure. For example, a subset of the range from 0 to 1.0 V may be selected. In another example, a voltage range including at least a portion of the range from 0 to 1.0 V and additional higher voltages may be selected. In yet another example, a range of voltages greater than 0 to 1.0 V may be selected. The range of swept voltages that is selected may depend, in part, on a geometry of the nanotip (e.g., size and/or shape), the potential target particulate(s) and a respective sensitivity of its I-V characteristic to a particular voltage or voltage range, the medium in which the sample is suspended, the carrier(s) to which potential target particulate(s) are attached, whether or not photonic wavelengths are simultaneously swept or not, and other factors. For example, if a first particulate is known to have a more distinguishable I-V characteristic in a first voltage range and the first particulate is a target particulate, the voltage range may be swept over the first voltage range. If a second particulate is known to have a more distinguishable I-V characteristic in a second voltage range different from the first voltage range, and the second particulate is a target particulate, the voltage range may be swept over the second voltage range. In an embodiment, the system 100 may be configured with a first voltage source that is electrically connected to a first subset of nanotips and a second voltage source that is electrically connected to a second subset of nanotips, with each voltage source sweeping a different voltage range to simultaneously target both the first and second target particulates.

Still further, the plurality of swept photonic wavelengths may be include at least a portion of a range of the electromagnetic spectrum from far-infrared wavelengths to far-ultraviolet wavelengths. The selected range of swept photonic wavelengths may be based on a geometry of the nanotip (e.g., size and/or shape), the potential target particulate(s) and a respective sensitivity of its I-V characteristic to a particular photonic wavelength or range of photonic wavelengths, the medium in which the sample is suspended, the carrier(s) to which potential target particulate(s) are attached, and/or other factors. In an embodiment, the entire infrared spectrum may be selected to be swept (e.g., 300 GHz (1 mm) to 400 Thz (750 nm)). In some embodiments, only a portion of the infrared spectrum may be selected to be swept, e.g., a far-infrared portion ranging from 300 Ghz (1 mm) to 30 THz (10 µm); a mid-infrared portion ranging from 30 to 120 Thz (10 to 2.5 µm); or a near-infrared portion ranging from 120 to 400 Thz (2500 to 760 nm). In some embodiments, a portion of the electromagnetic spectrum generally corresponding to visible light (e.g., around 790 Thz (380 nm) to 400 Thz (760 nm)) or a subset thereof may be swept. In some embodiments, at least a portion of the ultraviolet light spectrum (e.g., from about 10 nm to about 380 nm) may be swept. Typically, UV wavelengths shorter than 150 nm may be ionizing, and thus the portion of the UV spectrum above 150 nm may not be used to determine conductive-photonic spectrums. In some embodiments, two or more non-consecutive ranges of photonic wavelengths may be swept.

In some embodiments, multiple sensors may be contained within a chamber. In some embodiments, a milliampere-range ammeter may be used. In some embodiments, more than one ammeter may be used, for example, for different subsets of nanotips. In some embodiments, a single computing device 122 may control and receive data from multiple systems 100 or from multiple sensors 102.

Application of Nanotip Sensor System

The embodiments of the system 100, the nanotip sensor 200, and the methods 400, 450 and 470 of using the nanotip sensor for detecting and identifying particulates as described herein not only provide a high degree of sensitivity and responsiveness to different compounds and particulates, but also provide a high degree of stability and reproducibility, a short recovery time, and require only simple calibration. Furthermore, the system 100 is highly portable and is easily cleaned without hazardous waste by-products.

As such, the nanotip sensor 200 and the system 100 may be advantageously and easily used in a variety of settings to rapidly detect chemical, biological and other threat agents. Moreover, the threat agents may be quickly detected at an early stage without requiring incubation in a host, thus allowing action to be taken before a public mass infection occurs.

For example, one or more nanotip sensors 200 and/or systems 100 may be situated in public spaces such as airports, train stations, schools, post offices, and the like to sample ambient air for airborne biological or chemical threats, such as from bioterrorism or from leaks or accidents. One or more nanotip sensors 200 may even be situated within an airplane cabin space to sample the cabin air. Other possible locations for a nanotip sensor 200 or system 100 may include water filtration, treatment or reclamation plants, water towers, or bodies of water, where environmental water may be tested by the nanotip sensor. Still other possible locations for the nanotip sensor 200 or the system 100 include laboratories, hospitals, industrial plants, or other plant or campus settings.

In addition to general environmental sampling, target sampling may be performed using the nanotip sensor 200 or system 100. For example, a portable system may be used for opening suspicious mail, packages or envelopes. In particular, the suspicious item may be placed into the sealed chamber 105 of the system 100, and then may be opened to expose its contents to the sensor 200. In another example, as the system 100 may be relatively small in size, an instance of the system 100 may be built into shipping containers or other types of containers. Upon detection and identification of a dangerous or illegal substance by the sensor 102, the system 100 may generate a signal including an identification of the container and/or a geographical location so that officials may be notified.

Additionally, geographic migration of particulates may be determined and tracked using nanotip sensors 200 and/or systems 100. For example, if nanotip sensors 200 are situated at known locations of a chemical plant, and an accident that disperses dangerous chemicals occurs, various parts of the plant may be sealed off based on the data received at the geographically positioned sensors 200. In another example, if a new "superbug" or virus is identified, its path of entry into a country may be traced backwards through data collected via a chain of nanotip sensors, e.g., from a hospital to an airport to an airplane. Other applications and uses of detecting or identifying particulates using a nanotip sensor 200 may be possible.

The foregoing describes and exemplifies the invention but is not intended to limit the invention defined by the claims that follow. All of the methods disclosed and claimed herein can be made and executed without undue experimentation in light of the present disclosure. While the systems, apparatuses and methods of this invention have been described in terms of specific embodiments, it will be apparent to those of skill in the art that variations may be applied to the systems, apparatuses and/or methods and in the steps or in the sequence of steps of the methods described herein, without departing from the concept, spirit, and scope of the invention. More specifically, it will be apparent that certain agents which are both chemically and physiologically related may be substituted for the agents described herein while the same or similar results would be achieved. The scope of the invention is not limited to the specific embodiments described hereinabove, but rather, is intended to be defined by the spirit and scope of the claims and all equivalents thereof.

What is claimed is:

1. A sensor system for detecting particulates in a sample, comprising:
    a nanotip sensor array comprising a plurality of nanotip sensors, each nanotip sensor in the nanotip sensor array electrically coupled to a variable voltage source and a current measuring device, and comprising:
    a semiconductor layer;
    an electrically conductive nanotip formed on, and electrically coupled to, the semiconductor layer and configured as one of an anode or a cathode;
    an insulating layer formed on the semiconductor layer and having a gap surrounding the metallic nanotip; and
    an electrically conductive surface formed on the insulating layer and having a gap surrounding the metallic nanotip, and configured as the other of the anode or the cathode;
    a computing device configured to:
    control the variable voltage source, causing the variable voltage source to apply a plurality of voltages across the anode and the cathode;
    receive from the current measuring device a measured current value at each of the plurality of voltages to create a current versus voltage (I-V) characteristic for an unidentified particulate bridging the gap between the anode and the cathode; and
    compare the I-V characteristic for the unidentified particulate to a plurality of identified particulate I-V profiles stored in a database to determine the identity of the unidentified particulate.

2. The sensor system of claim 1, further comprising a filter configured to separate the sample from a carrier.

3. The sensor system of claim 1, further comprising a filter configured to prevent non-targeted particulates from reaching the nanotip sensor array.

4. The sensor system of claim 1, wherein the nanotip sensor array is self-cleaning.

5. The sensor system of claim 4, wherein the computing device is configured to control the variable voltage source to increase a magnitude of a voltage applied to the sensor to an ionizing voltage so that any particulates adsorbed to the plurality of nanotip sensors are ionized and desorbed.

6. The sensor system of claim 1, wherein the sensor system is reusable to analyze more than one sample.

7. The sensor system of claim 1, wherein each of one or more of the plurality of nanotip sensors is primed with a primer corresponding to a target particulate.

8. The sensor system of claim 7, wherein the primer is an antibody.

9. The sensor system of claim 1, further comprising a variable frequency light source arranged to shine light on the sensor, and wherein the computing device is further configured to generate a conductive-photonic response curve by creating a current versus voltage (I-V) characteristic at each of a plurality of different wavelengths of the variable frequency light source.

10. The sensor system of claim 9, wherein comparing the I-V characteristic for the unidentified particulate to a plurality of identified particulate I-V profiles to determine the identity of the unidentified particulate comprises comparing the conductive-photonic response curves for the unidentified particulate to a plurality of identified particulate conductive-photonic response curves to determine the identity of the unidentified particulate.

* * * * *